(12) United States Patent
Truesdale et al.

(10) Patent No.: US 6,469,021 B1
(45) Date of Patent: Oct. 22, 2002

(54) NON-PEPTIDE ANTAGONISTS OF GLP-1 RECEPTOR AND METHODS OF USE

(75) Inventors: Larry Kenneth Truesdale, San Diego; Richard A. Bychowski, Cardiff; Javier Gonzalez, Oceanside; Atsuo Kuki, Encinitas; Ranjan Jagath Rajapakse, San Diego; Min Teng, San Diego; Dan Kiel, San Diego, all of CA (US); Daljit S. Dhanoa, West Chester, PA (US); Yufeng Hong, San Diego, CA (US); Tso-sheng Chou, San Diego, CA (US); Anthony L. Ling, San Diego, CA (US); Michael David Johnson, Cardiff, CA (US); Vlad Edward Gregor, San Diego, CA (US)

(73) Assignee: Agouron Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 09/831,572

(22) PCT Filed: Dec. 8, 1999

(86) PCT No.: PCT/US99/09065

§ 371 (c)(1),
(2), (4) Date: Oct. 26, 2001

(87) PCT Pub. No.: WO99/58201

PCT Pub. Date: Nov. 18, 1999

Related U.S. Application Data

(60) Provisional application No. 60/111,736, filed on Dec. 10, 1998.

(51) Int. Cl.$^7$ ..................... A61K 31/437; C07D 471/04
(52) U.S. Cl. ..................... 514/292; 546/85; 546/87; 546/64; 544/126; 544/233; 544/361; 514/232.8; 514/248; 514/253; 514/287
(58) Field of Search ................. 514/292, 287, 514/253, 232.8, 248; 546/85, 87, 64; 544/126, 233, 361

(56) References Cited

U.S. PATENT DOCUMENTS 5,834,482 A 11/1998 Lundbeck et al.

OTHER PUBLICATIONS

Collins J. L. et al., "CP–99, 711: A non–peptide glucagon receptor antagonist", *Bioorganic& Medicinal Chemistry Letters*, Oxford, GB, vol. 2, No. 9, 1992, 915–918, XP000940891.

Supplementary Partial European Search Report, EP 99 96 0663, May 2, 2002.

Voelker, T., et al, "o–Nitrobenzyl as a Photocleavable Nitrogen Protecting Group for Indoles, Benzimidazole, and 6–Chlorouracil.", Tetrahedron Letters 39,1998; 359–362.

Lippke, K.P., et al., "β–Carbolines as Benzodiazepine Receptor Ligands II: Synthesis and Benzodiazepine Receptor Affinity of β–Carboline–3–carboxylic Acid Amides", Journal of Pharm. Science, vol. 74(6), 1985, 676–680.

Kelly, T.R., et al., "Maxonine: Structure Correction and Synthesis", Tetrahedron Letters, vol. 34(39), 1993, 6173–6176.

Huth, A., et al., "Carbonylation in Benzyl Alcohol. A New and Easy Method for the Preparation of Aromatic Benzyl Esters", Tetrahedron Letters, vol. 43(6), 1987, 1071–1074.

Moody, C.J. et al., "[2,3] Fused Indoles. Synthesis of β–Carbolines and Azepino [4,5–b] Indoles from 3–(2–Alkylindol–3–yl)–2–azidoacrylates", J. Chem. Soc. Perkin Trans, 1984, vol. 1, 2985–2901.

Cain, M. et al, "β–Carbolines: Synthesis and Neurochemical and Pharmacological Actions on Brain Benzodiazepine Receptors", J. Med. Chem.,25, 1982, 1081–1091.

Fehman et al., 1995, Endocr.Rev. 16:390–410.

Thorens et al., 1995, Diabetes Metab. (Paris) 21:311–318.

Larsson et al., 1997, Acta Physiol. Scand. 160:413–422.

Ore et al., 1997, Journal of Gerontology: Biological Sciences 52A(5): B245–B249.

Montrose–Rafizadeh et al., 1997, J. Biol. Chem. 272(34): 21201–21206.

Larsen et al., 1997, Ebdicrinology 138(10): 4445–4455.

Navarro et al., 1996, J. Neurochem. 67(5): 1982–1991.

Tang–Christensen, 1996, Amer. J. Physiol. 271(4 Part 2): R848–R856.

Turton et al., 1996. Nature 379(6560): 69–72.

Vecht, 1997, Scand. J. Gastroenterol. Suppl. 223:21–27.

Montrose–Rafizadeh et al., 1997, J. Cell Phys. 172(3): 275–283.

Staab, H.A., ACIEE 1962, 1:351.

Couts et al., Heterocycles 1984, 22:131.

Swain et al., J. Med. Chem., 1991, 34:140.

Dodd et al., J. Org. Chem., 1993, 58:7587.

Narashimhan et al., Synthesis, 1975, 797.

Abdel–Magid et al., J. Org. Chem., 1996, 61:3849.

Mylari et al., J. Org. Chem. 1991, 56:2587.

PCT International Search Report, PCT/US99/29065.

*Primary Examiner*—Charanjit S. Aulakh
(74) *Attorney, Agent, or Firm*—Shanks & Herbert

(57) ABSTRACT

Non-peptide compounds that act as antagonists of the intestinal hormone glucagons-like peptide 1 (GLP-1) have a 9H-b-carboline central motif. The compounds exhibit advantageous physical, chemical and biological properties and inhibit GLP-1 peptide binding to the GLP-1 receptor and/or prevent activation of the receptor by bound GLP-1. The invention further relates to a method of inhibiting the binding of GLP-1 to the GLP-1 receptor and a method of inhibiting the activation of the GLP-1 receptor. Intermediate compounds useful for making non-peptide GLP-1 receptor antagonists are also described.

18 Claims, No Drawings

US 6,469,021 B1

NON-PEPTIDE ANTAGONISTS OF GLP-1 RECEPTOR AND METHODS OF USE

This application is a 371 of PCT/US99/09065 filed Dec. 8, 1999 which claims benefit of provisional application No. 60/111736 filed Dec. 10, 1998.

TECHNICAL FIELD AND INDUSTRIAL APPLICABILITY OF THE INVENTION

The present invention relates generally to compounds that act as antagonists to the intestinal hormone glucagon-like peptide 1 (GLP-1). More particularly, the invention relates to non-peptide GLP-1 antagonists which have advantageous physical, chemical and biological properties. The GLP-1 antagonists of the present invention inhibit binding of GLP-1 peptide to the GLP-1 receptor and/or prevent the activation of the receptor by bound GLP-1. The invention further relates to a method of inhibiting the binding of GLP-1 to the GLP-1 receptor and a method of inhibiting the activation of the GLP-1 receptor.

BACKGROUND OF THE INVENTION

GLP-1 is an intestinal hormone released within minutes of food ingestion which potentiates insulin release and aids in the regulation of glucose uptake and metabolism. GLP-1 is derived by post-translational processing of proglucagon and is secreted by the intestinal endocrine L-cells (Fehman et al., 1995, *Endocr. Rev.* 16:390–410; Thorens et al., 1995, *Diabetes Metab.* (Paris) 21:311–318). The insulin-trophic effects of GLP-1 make it a useful target in the management of diabetes and other glucose intolerance management problems during critical illness.

Results of recent studies conducted in non-diabetic women aged 59 years suggest that GLP-1 reduces plasma glucose levels primarily by reducing hepatic glucose production and increasing the metabolic clearance rate of glucose through indirectly increasing the insulin-to-glucagon ratio in healthy individuals (Larsson et al., 1997, *Acta Physiol. Scand.* 160:413–422). Glucose intolerance is a common feature of the aging process; aging has been identified as an etiologic factor for Type II diabetes mellitus.

In a study designed to characterize the abnormalities in beta cells that occur in the aging process, insulin responses were found to be similar in both age groups studied. GLP-1 in conjunction with IVGTT was found to restore the acute insulin response to glucose while increasing the clearance of glucose in the older animals. The conclusion drawn is that an impaired glucose-mediated insulin response is present in the older animals although the animals maintained their insulin responsivity to GLP-1 (Ore et al., 1997, *Journal of Gerontology: Biological Sciences* 52A(5):B245–B249).

A GLP-1 agonist refers to a compound or agent that mimics the physiological and pharmacological properties of endogenous GLP-1. A GLP-1 antagonist refers to a compound or agent that attenuates the effects of GLP-1 through the ability of these compounds or agents to inhibit GLP-1 peptide binding to the GLP-1 receptor and/or prevent the activation of the receptor by bound GLP-1.

The glucagon-like peptides GLP-1-(7–36)-amide and exendin-4-(1–39) have been identified as GLP-1 agonists. The glucagon-secretin-vasoactive intestinal peptide exendin-(9–39) has been identified as a GLP-1 antagonist (Montrose-Rafizadeh et al., 1997, *J. Biol. Chem.* 272(34) :21201–21206).

Peptide antagonists of peptide hormones are often quite potent. However, the use of peptide antagonists is typically associated with problems due to susceptibility to enzymatic degradation and poor biodistribution, i.e., the inability to be readily transported from the digestive system into the blood stream. Thus, such antagonists have limited effectiveness as drugs since it is difficult to achieve the desired blood levels of peptide antagonists in low dosages. Consequently, there is a need for GLP-1 antagonists, and particularly for non-peptide GLP-1 antagonists.

GLP-1 antagonists have potential to be used therapeutically to increase eating in disorders characterized by cachexia. For example, work by Larsen et al. has shown that the central administration of GLP-1 activates the central CRH-containing neurons of the hypothalamo-pituitary-adrenocortical axis, which may be responsible for feeding behaviors (Larsen et al., 1997, *Endocrinology* 138(10): 4445–4455). Much evidence shows that GLP-1 agonists inhibit food and water intake in rat, and these effects are blocked by the GLP-1 receptor antagonist exendin-(9–39) amide (Navarro et al., 1996, *J. Neurochem.* 67(5): 1982–1991; Tang-Christensen, 1996, *Amer. J. Physiol.* 271(4 Part 2):R848–856). Exendin-(9–39) alone increases feeding in other rat models (Turton et al., 1996, *Nature* 379(6560):69–72). In addition, GLP-1 receptor antagonists may be useful in post-prandial hypoglycemia and the dumping syndrome, where there is an exaggerated GLP-1 release (Vecht, 1997, *Scand. J. Gastroenterol. Suppl.* 223:21–27).

Thus, there is a need for effective non-peptide GLP-1 antagonists useful for the therapeutic regulation of GLP-1 that avoid the in vivo degradation and biodistribution problems exhibited by peptide GLP-1 antagonists.

SUMMARY OF THE INVENTION

An object of the present invention is to provide non-peptide GLP-1 antagonists useful as pharmaceuticals. A further object of the invention is to provide methods of synthesizing the compounds and intermediate compounds useful in such syntheses. The compounds of the invention are pharmaceutically superior to peptide compounds since they provide better biodistribution and tolerance to degradation by physiological enzymes.

The invention is directed to GLP-1-antagonizing compounds of the general formula:

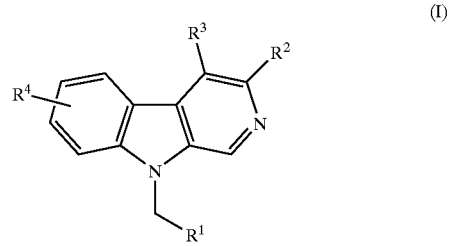

(I)

wherein:

$R^1$ is a phenyl or pyridyl group optionally substituted with one or more substituents independently selected from halogen, hydroxyl, nitro, trifluoromethyl, cyano, $C_1$–$C_6$ alkyl, $C_2$–$C_6$ alkenyl, and $C_1$–$C_6$ alkoxy groups;

$R^2$ is:

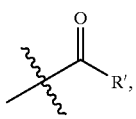

where R' is: hydrogen; a hydroxy group; —$OR^5$, where $R^5$ is a $C_1$–$C_6$ alkyl or $C_2$–$C_6$ alkenyl group optionally substituted with a hydroxy group or an amino, $C_1$–$C_6$ alkoxy, cycloalkyl, thioether, heterocycloalkyl, aryl, or heteroaryl group optionally substituted with one or more substituents independently selected from alkyl, hydroxyalkyl, carboxyl, $C_1$–$C_6$ alkoxycarbonyl, oxygen, halogen, and trifluoromethyl groups; or —$NR^6R^7$, where $R^6$ and $R^7$ are each independently hydrogen or a $C_1$–$C_6$ alkyl, $C_2$–$C_6$ alkenyl, amino, or imino group optionally substituted with a hydroxy group, a $C_1$–$C_6$ alkoxy group, or an amino, thioether, heterocycloalkyl, aryl, or heteroaryl group optionally substituted with one or more substituents independently selected from oxygen, halogen, trifluoromethyl, and carboxyl groups, or where —$NR^6R^7$ forms a 5- or 6-membered heterocyclic ring optionally containing, in addition to the nitrogen heteroatom, a heteroatom selected from O, N, and S;

—$(CH_2)_n$—O—R", where n is 1 or 2, and R" is hydrogen, a $C_5$–$C_7$ heteroaryl group, or

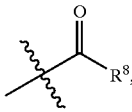

where $R^8$ is hydrogen, a $C_1$–$C_6$ alkyl group, a $C_3$–$C_6$ cycloalkyl group, or a 5- or 6-membered heteroaryl group optionally substituted with one or more substituents independently selected from halogens, methyl, and trifluoromethyl;

—$(CH_2)_p$—N(R")(R'''), where p is 1 or 2, R" is as defined above, and R''' is hydrogen or an alkyl or alkoxy group optionally substituted with a $C_3$–$C_6$ cycloalkyl group optionally substituted with cyano;

—CH=N—R'''', where R'''' is hydrogen, hydroxy, or —$OR^9$, where $R^9$ is an alkyl, cycloalkyl, aryl, or heteroaryl group; or a 5- or 6-membered heterocyclic ring containing one to three heteroatoms independently selected from O, N, and S, the ring being optionally substituted with one or two substituents independently selected from methyl, methoxymethyl, oxygen, and $C_1$–$C_6$ alkoxy groups;

$R^3$ is hydrogen or a $C_1$–$C_6$ alkyl, $C_2$–$C_6$ alkenyl, or ($C_1$–$C_3$ alkoxy)$C_1$–$C_3$ alkyl group;

or $R^2$ and $R^3$ together with the atoms to which they are bound form a 5- or 6-membered ring containing one or two heteroatoms selected from O, N, and S, the ring being optionally substituted with oxygen, hydroxyl, or a $C_1$–$C_6$ alkyl group optionally substituted with a 5- or 6-membered heterocycloalkyl containing one or two heteroatoms independently selected from O, N, and S; and $R^4$ is hydrogen or an amino, halogen, hydroxyl, nitro, trifluoromethyl, cyano, $C_1$–$C_6$ alkyl, or $C_2$–$C_6$ alkenyl group.

The invention is also directed to prodrugs, pharmaceutically acceptable salts, pharmaceutically acceptable solvates, and active metabolites of the compounds of the Formula (I).

The GLP-1 antagonists of the present invention inhibit GLP-1 peptide binding to the GLP-1 receptor and/or prevent the activation of the receptor by bound GLP-1. Accordingly, the invention is further directed to a method of inhibiting the binding of GLP-1 to the GLP-1 receptor and a method of inhibiting the activation of the GLP-1 receptor using the inventive compounds.

DETAILED DESCRIPTION AND PREFERRED EMBODIMENTS OF THE INVENTION

In accordance with a convention used in the art,

is used in structural formulas herein to depict the bond that is the point of attachment of the moiety or substituent to the core or backbone structure.

As used herein, the terms "alkyl group" is intended to mean a straight- or branched-chain monovalent radical of saturated carbon atoms and hydrogen atoms, such as methyl (Me), ethyl (Et), propyl, isopropyl, butyl, isobutyl, t-butyl, and the like.

The term "alkenyl group" refers to a straight- or branched-chain alkene-type radical containing one or more double bonds, such as ethenyl, pentenyl, butenyl, propenyl, and the like.

"Alkynyl group" refers to a straight- or branched-chain alkyne-type radical containing at least one triple bond, such as ethynyl, butynyl, propynyl, pentynyl, hexynyl, and the like.

A "cycloalkyl group" is intended to mean a non-aromatic monovalent monocyclic, bicyclic, or tricyclic radical containing 3 to 14 carbon ring atoms, each of which may be saturated or unsaturated. Illustrative examples of cycloalkyl groups include the following moieties:

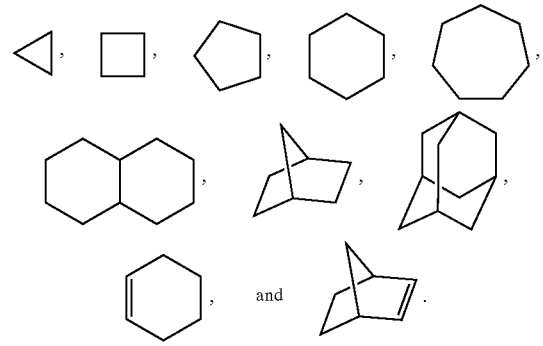

A "heterocycloalkyl group" is intended to mean a non-aromatic monovalent monocyclic, bicyclic, or tricyclic radical, which is saturated or unsaturated, containing 3 to 18 ring atoms, which includes 1 to 5 heteroatoms selected from nitrogen, oxygen, and sulfur. Illustrative examples of heterocycloalkyl groups include the following moieties, where R is any suitable substituent:

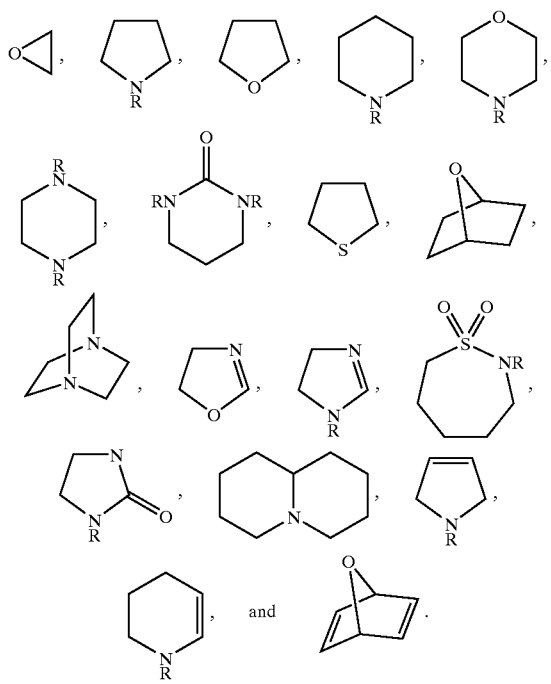

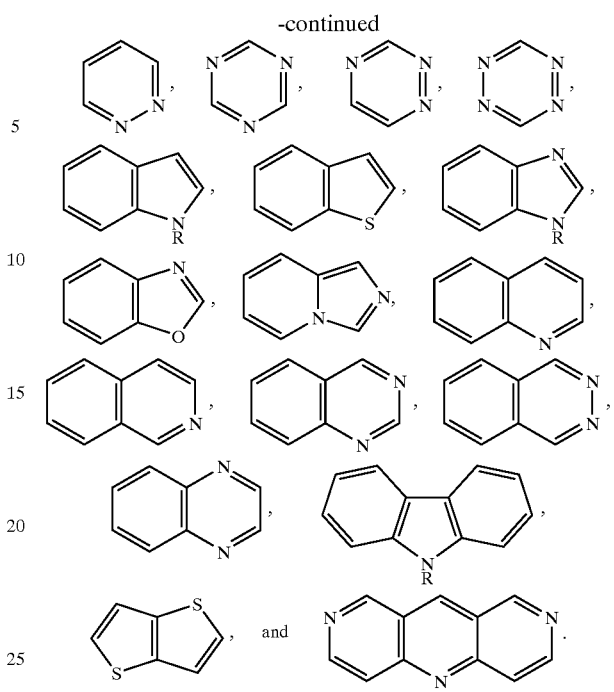

An "aryl group" is intended to mean an aromatic monovalent monocyclic, bicyclic, or tricyclic radical containing 6 to 18 carbon ring atoms. Illustrative examples of aryl groups include the following moieties:

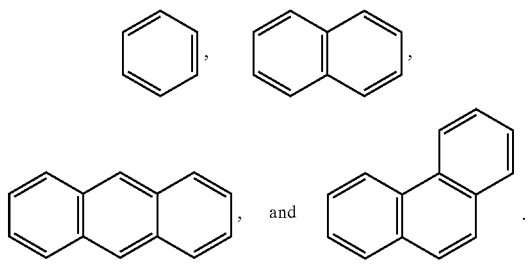

A "heteroaryl group" is intended to mean an aromatic monovalent monocyclic, bicyclic, or tricyclic radical containing 4 to 18 ring atoms, including 1 to 5 heteroatoms selected from nitrogen, oxygen, and sulfur. Illustrative examples of heteroaryl groups include the following moieties:

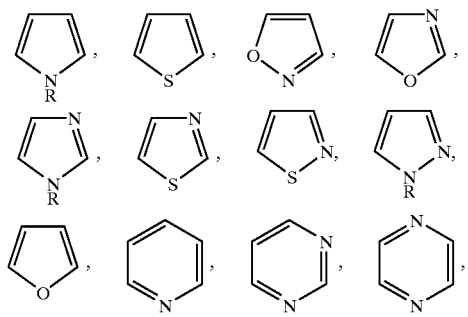

A "heterocycle" is intended to mean a heteroaryl or heterocycloalkyl group.

An "acyl group" is intended to mean a —C(O)—R radical, where R is a carbon—, oxygen—, nitrogen—, or sulfur—linked substituent.

A "sulfonyl group" is intended to mean an —SO₂R radical, where R is a carbon-, oxygen-, or nitrogen-linked substituent.

An "amino group" is intended to mean an —NH₂ radical or a primary, secondary, or tertiary amine radical (e.g., NHR$_a$, where R$_a$ is an alkyl group; and —NR$_a$R$_b$, where R$_a$ and R$_b$ are each independently an alkyl group).

An "imino" substituent refers to a substituent containing a carbon—nitrogen double bond, for example,

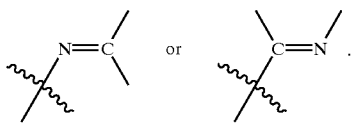

An "alkoxy group" is intended to mean the radical —OR$_a$, where R$_a$ is an alkyl group. Exemplary alkoxy groups include methoxy, ethoxy, propoxy, and the like.

An "alkoxycarbonyl group" is intended to mean the radical —C(O)OR$_a$, where R$_a$ is an alkyl group.

The term "thioether" refers to alkylthio, arylthio, and heteroarylthio groups. An "alkylthio group" is intended to mean the radical —SR$_a$, where R$_a$ is an alkyl group. An "arylthio group" is intended to mean the radical —SR$_c$, where R$_c$ is an aryl group. A "heteroarylthio group" is intended to mean the radical —SR$_d$, where R$_d$ is a heteroary. group.

An "aryloxy group" is intended to mean the radical —OR$_c$, where R$_c$ is an aryl group. A "heteroaryloxy group" is intended to mean the radical —OR$_d$, where R$_d$ is a heteroaryl group.

The term "substituent" or "suitable substituent" is intended to mean any chemically suitable substituent that may be recognized or selected, such as through routine testing, by those skilled in the art. Illustrative examples of suitable substituents include hydroxy (—OH), halogens, oxo groups, alkyl groups, acyl groups, sulfonyl groups, mercapto groups, alkylthio groups, alkoxy groups, cycloalkyl groups, heterocycloalkyl groups, aryl groups, heteroaryl groups, carboxy (—C(O)OH), amino groups, carbamoyl (—C(O) NH$_2$), aryloxy groups, heteroaryloxy groups, arylthio groups, heteroarylthio groups, and the like.

The term "optionally substituted" is intended to indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

A "prodrug" is intended to mean a compound that is converted under physiological conditions or by solvolysis or metabolically to a specified compound that is pharmaceutically active.

A "pharmaceutically active metabolite" is intended to mean a pharmacologically active product produced through metabolism in the body of a specified compound.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine.

A "pharmaceutically acceptable salt" is intended to mean a salt that retains the biological effectiveness of the free acids and bases of the specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates (mesylates), propanesulfonates, naphthalene-1-sulfonates, naphthalene-2-sulfonates, and mandelates.

The action of GLP-1 is antagonized by the 9H-β-carboline compounds of the general Formula (I):

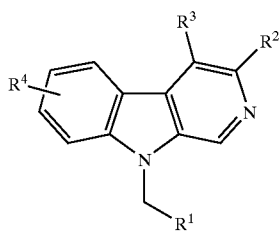
(I)

wherein R$^1$, R$^2$, R$^3$, and R$^4$ are as defined above. The invention is also directed to prodrugs, pharmaceutically acceptable salts, pharmaceutically acceptable solvates, and active metabolites of such compounds.

In a preferred embodiment, R$^1$ is a phenyl group substituted with one or more groups selected from halogen, hydroxyl, nitro, trifluoromethyl, and cyano.

Also preferred are compounds where R$^2$ is

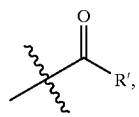

where R' is as defined above and incorporates a hydrogen-bond acceptor substituent that can, through normal conformational variations, assume a position 3–5 Å from the carbonyl group. As used herein, "hydrogen-bond acceptor substituent" refers to a substituent that includes an N or O capable of forming a hydrogen bond with a hydrogen-bond donor such as —OH or =NH. Exemplary hydrogen-bond acceptor substituents include moieties containing a group such as

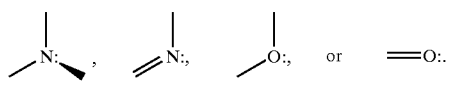

Exemplary R$^2$ groups of this type include

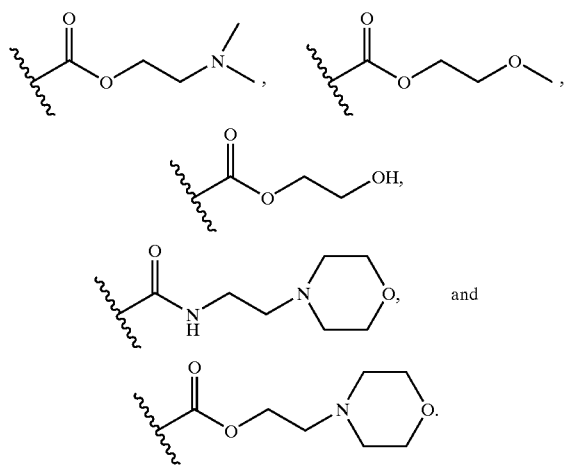

As known in the art, the shorthand designation

is used herein to depict —CH$_3$.

Also preferred are compounds wherein R$^3$ is hydrogen or methoxymethyl.

In a further preferred embodiment, R$^1$ is 2,5-dichlorophenyl or 3,5-dinitrophenyl.

In another preferred embodiment, R$^2$ and R$^3$ together with the atoms to which they are bound form a 5- or 6-membered lactone or lactam ring.

In yet another preferred embodiment, R$^2$ is selected from:

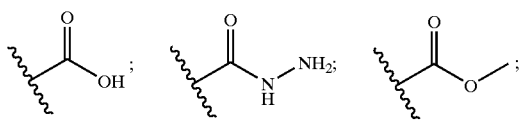

-continued
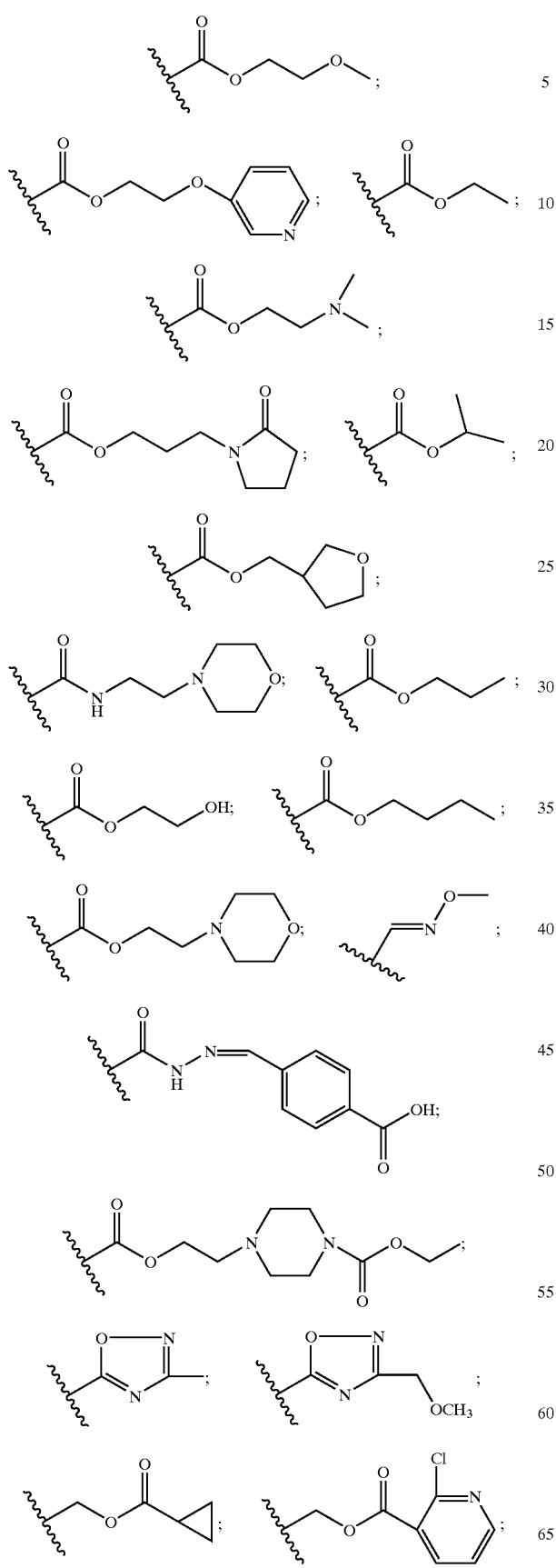
-continued
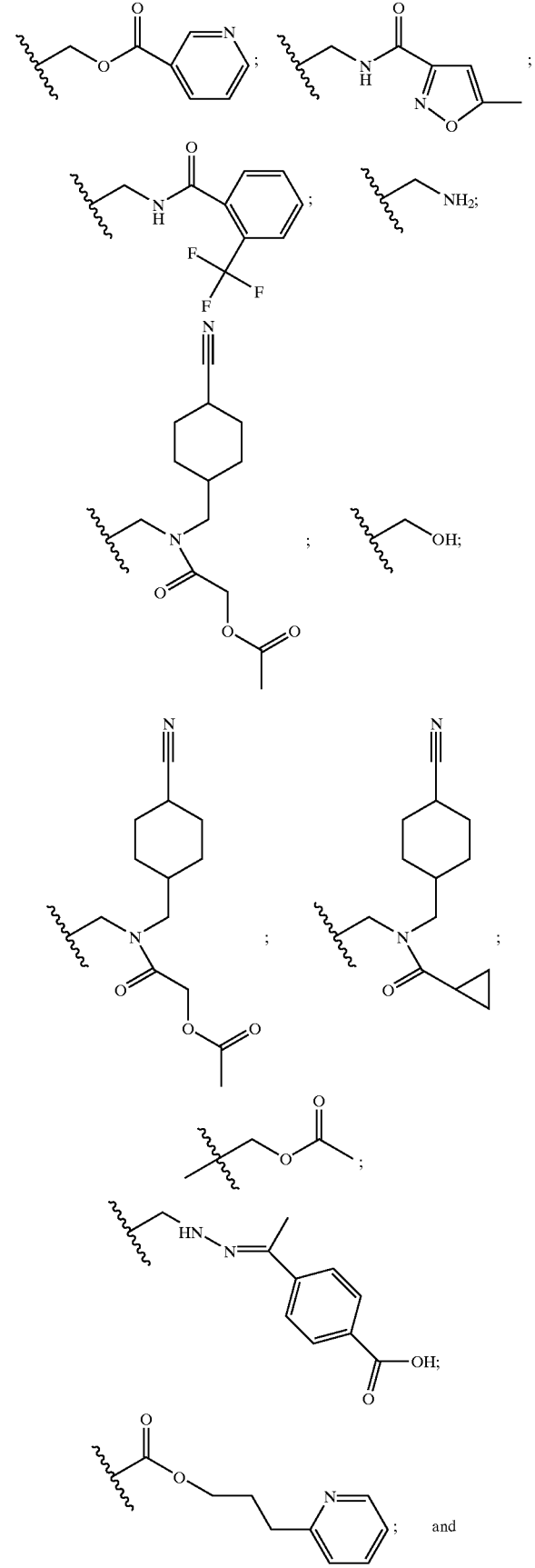

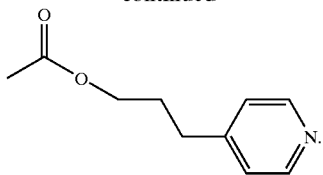
In another preferred embodiment, the 5- or 6-membered ring formed by $R^2$ and $R^3$ and the atoms to which they are bound is selected from:
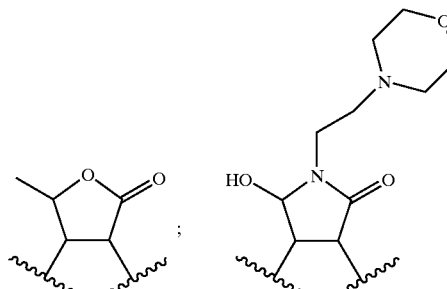
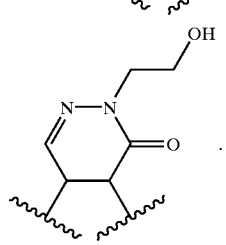
Especially preferred compounds represented by the above general Formula (I) include the following:
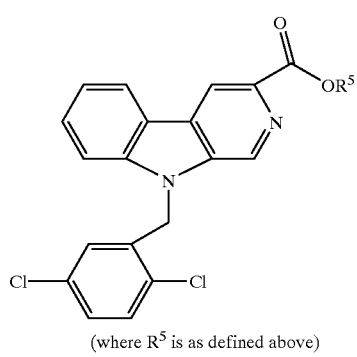
(where $R^5$ is as defined above)
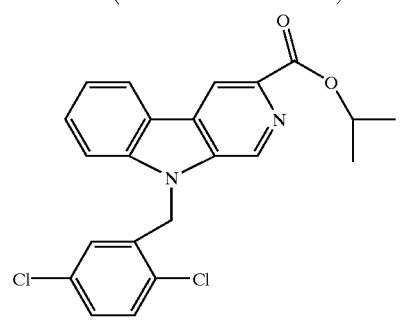
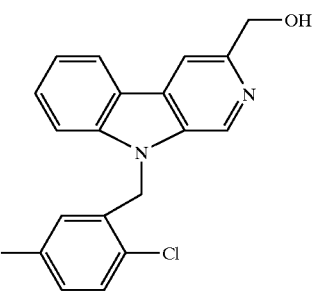
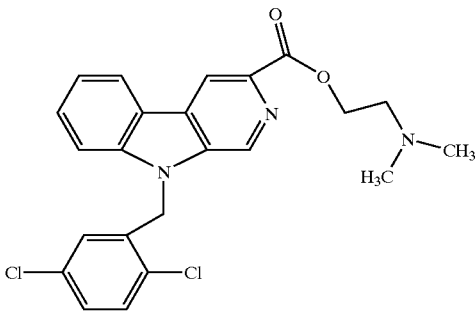
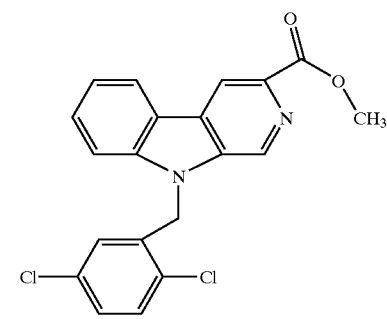
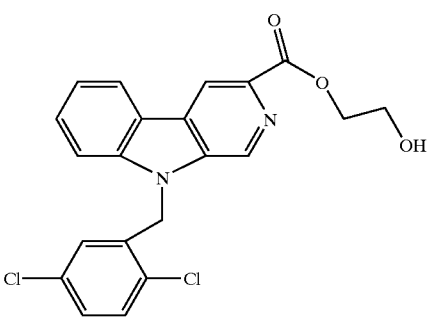
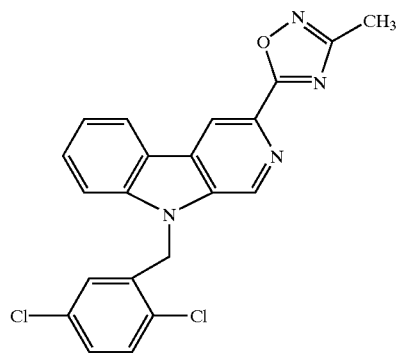

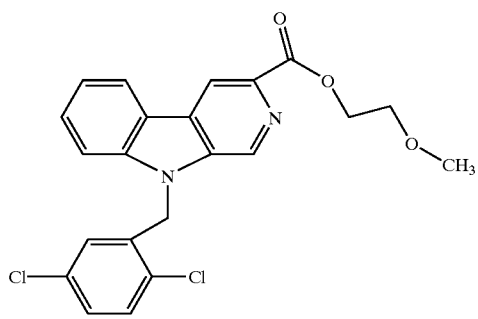
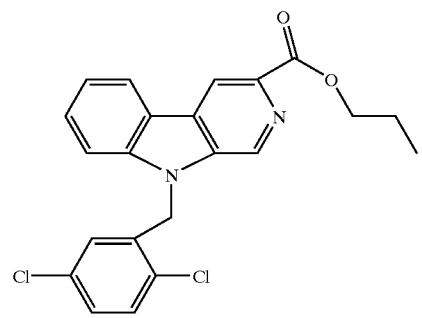
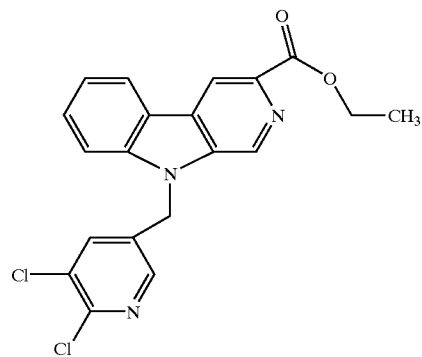
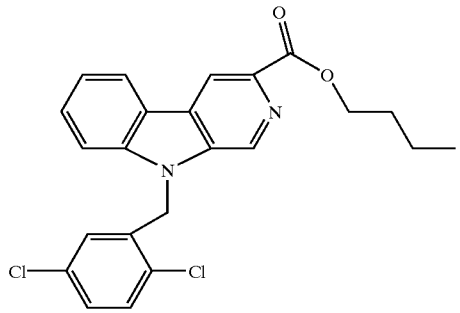
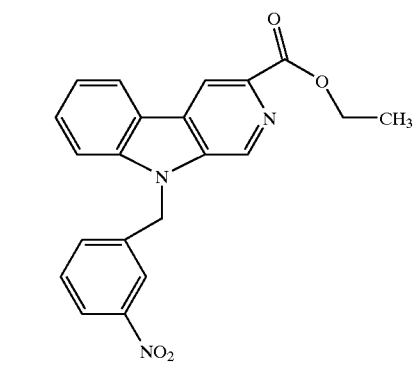
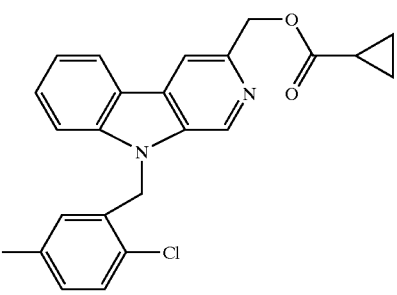
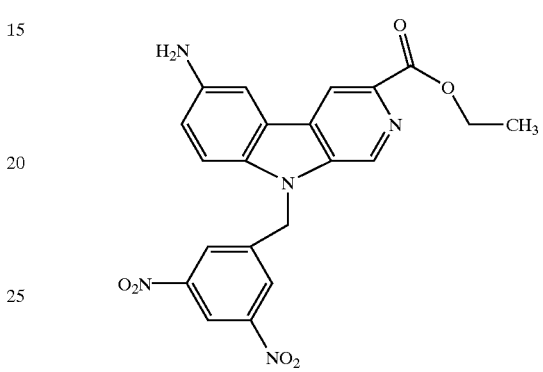
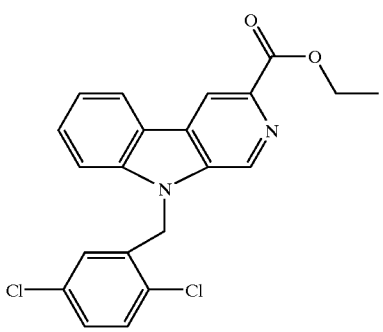
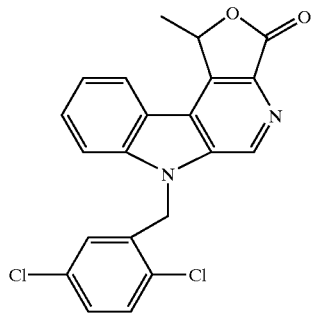
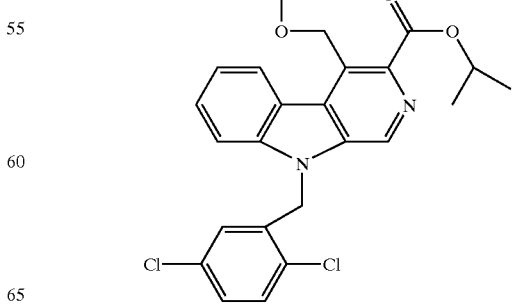

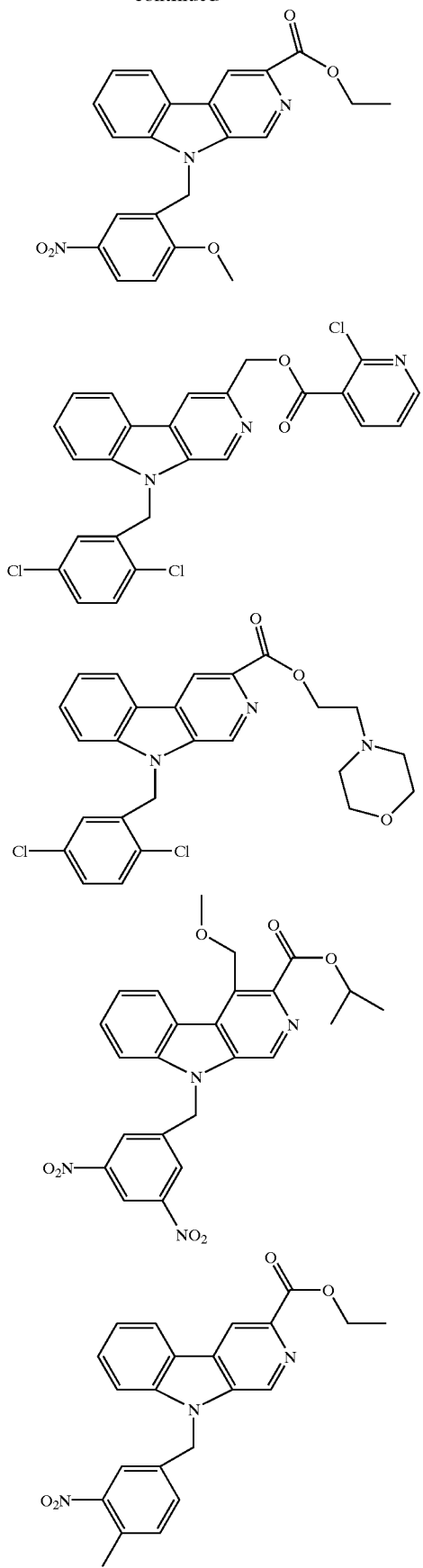
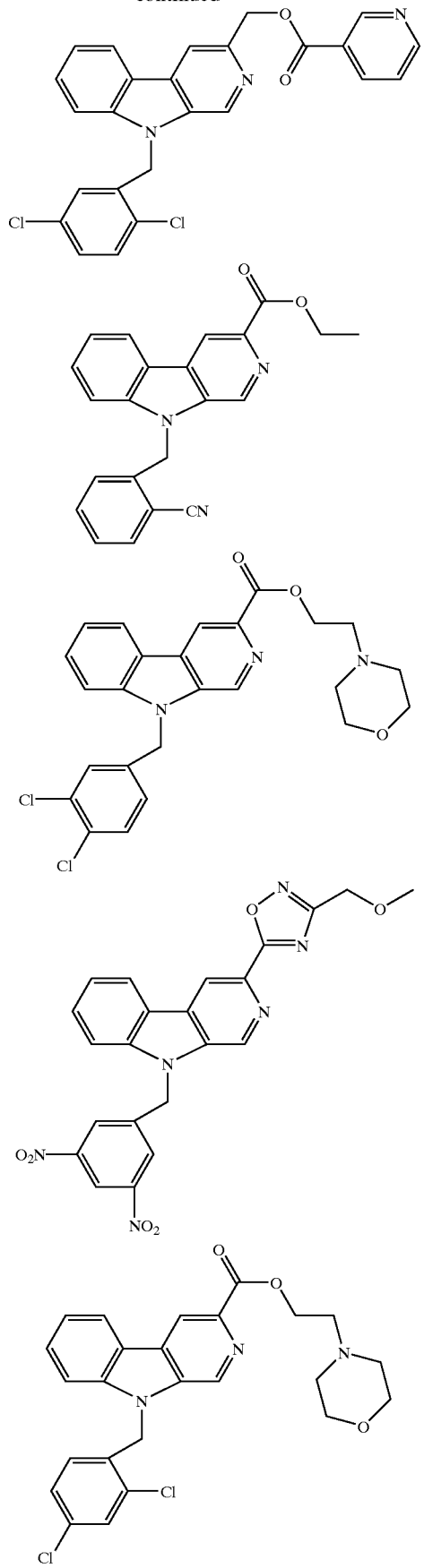

-continued
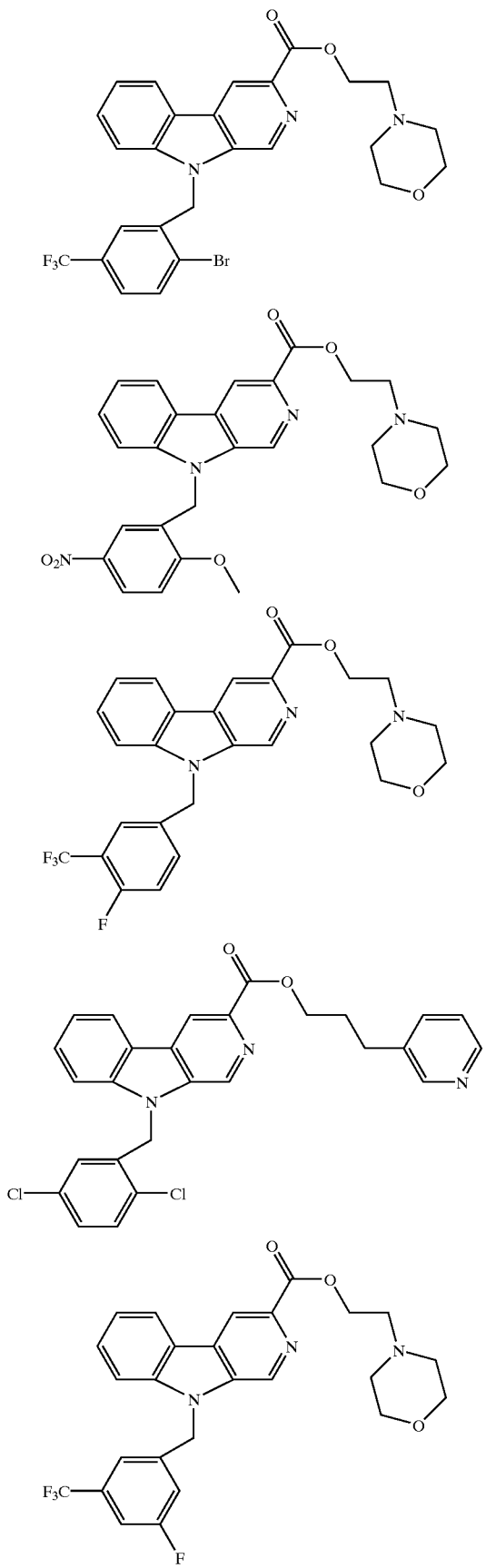
-continued
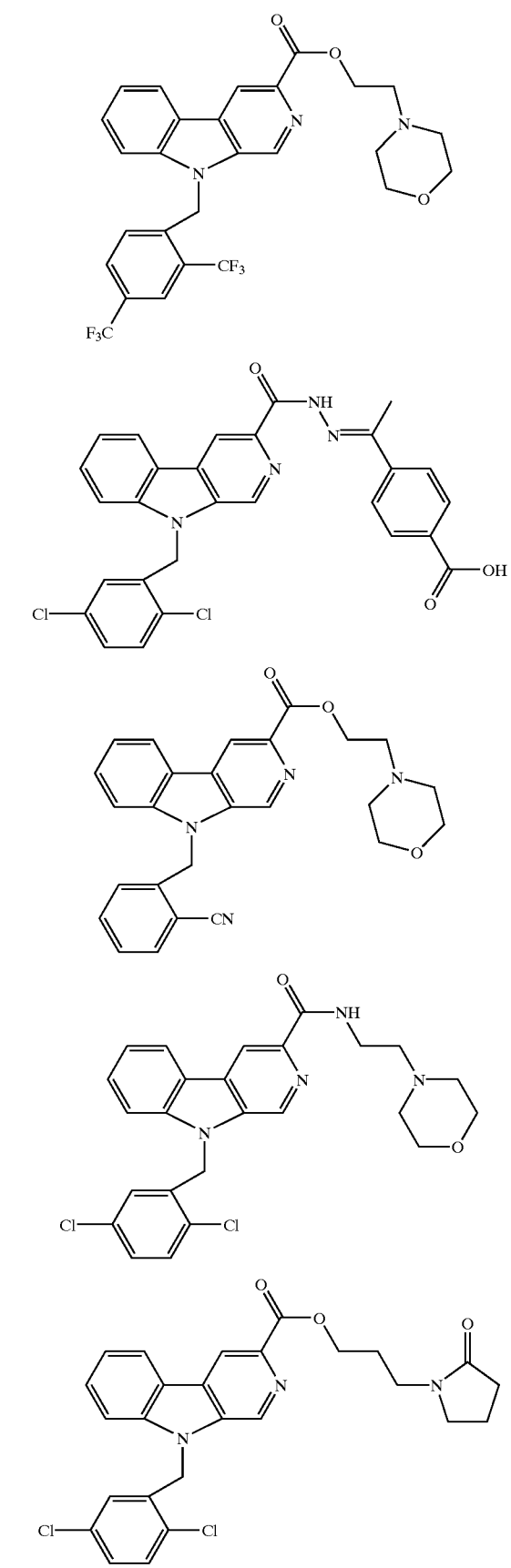

-continued
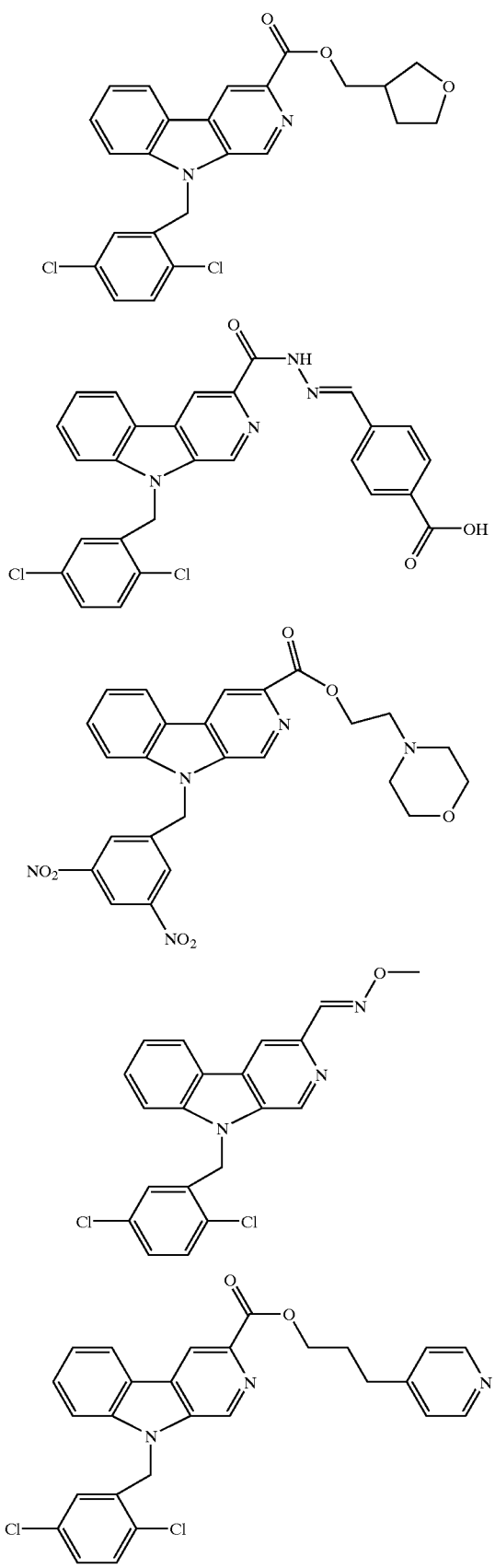
-continued
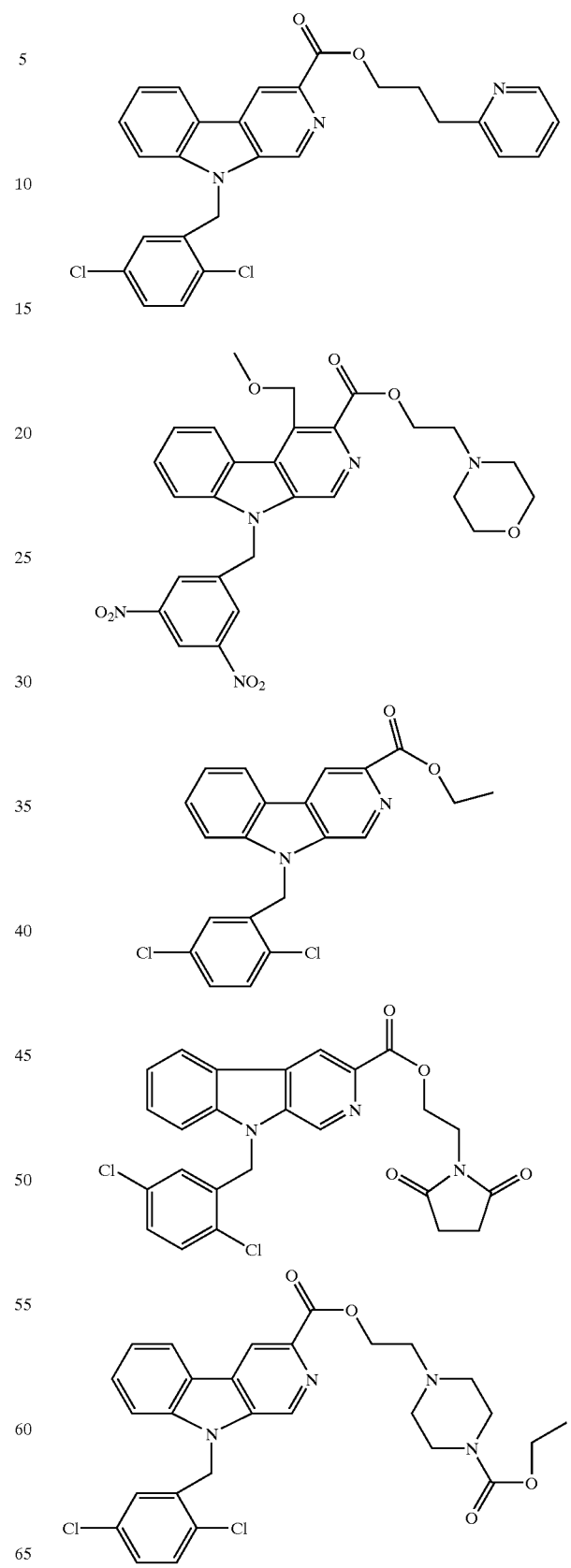

21
-continued
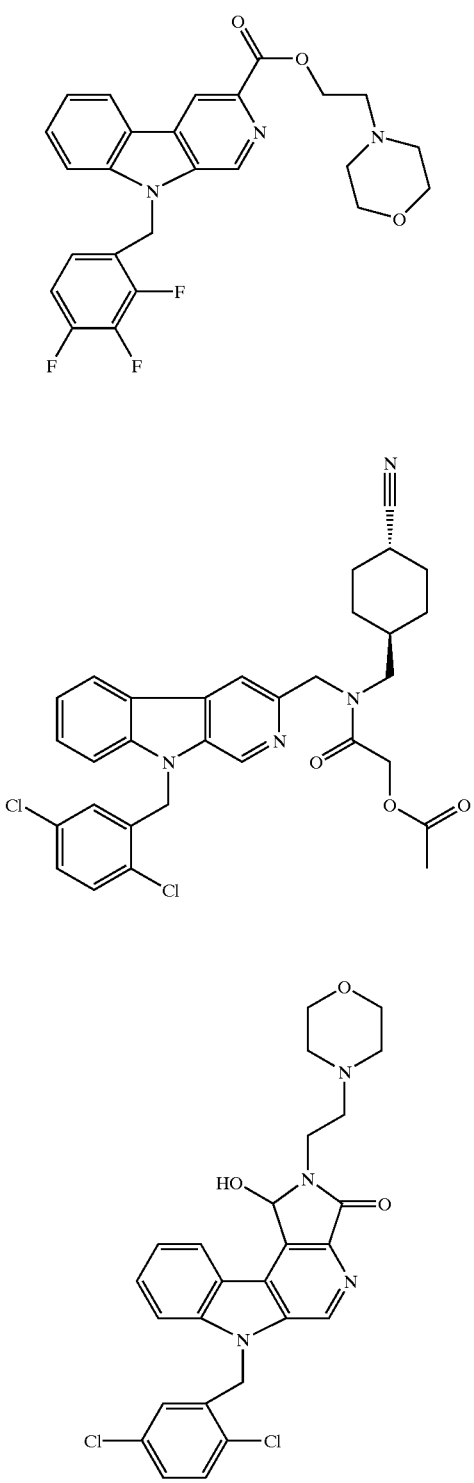
22
-continued
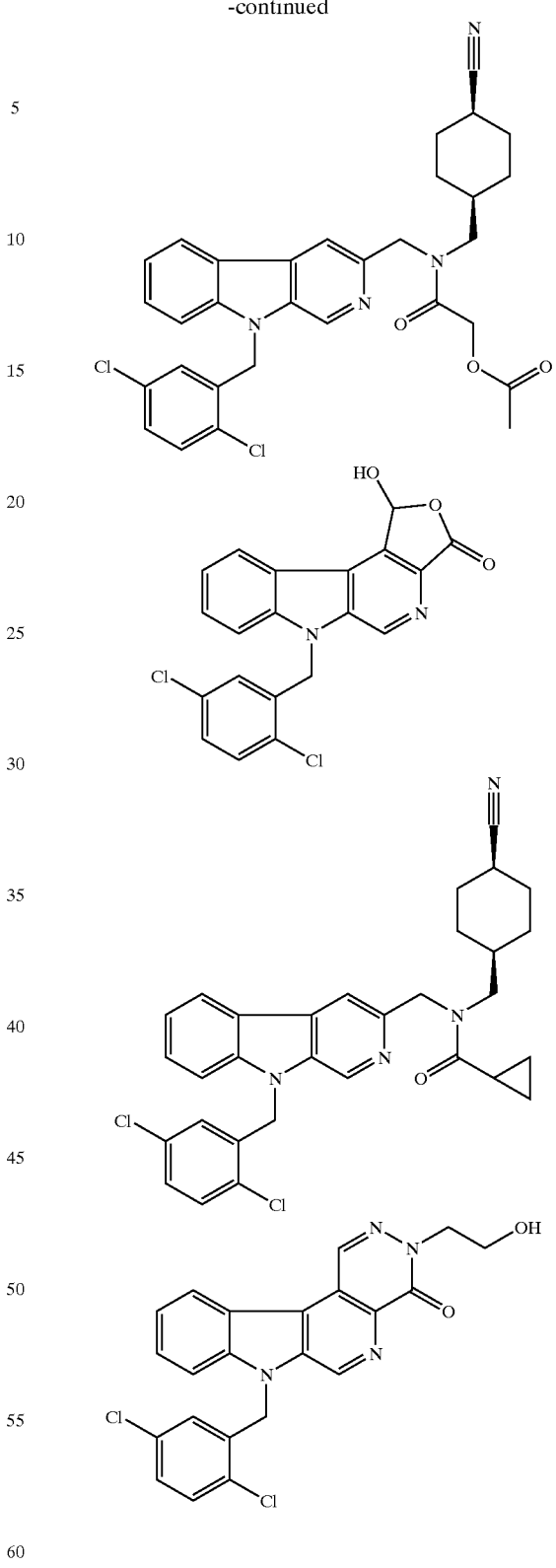

-continued

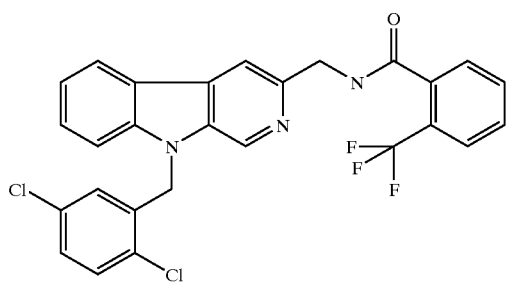

and

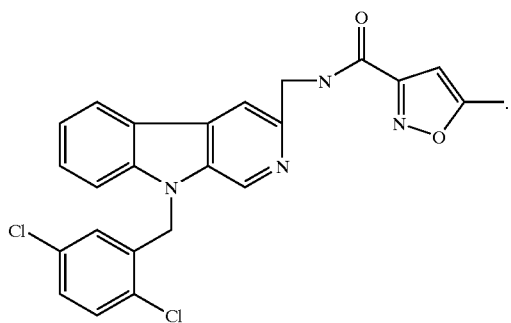

In addition, the present invention is directed to precursors, building blocks, and intermediates that are useful in preparing the compounds of Formula (I). The examples illustrate specific precursors, building blocks, and intermediates within the scope of the present invention. In particular, the following compounds can be used to synthesize certain compounds within the scope of the present invention:

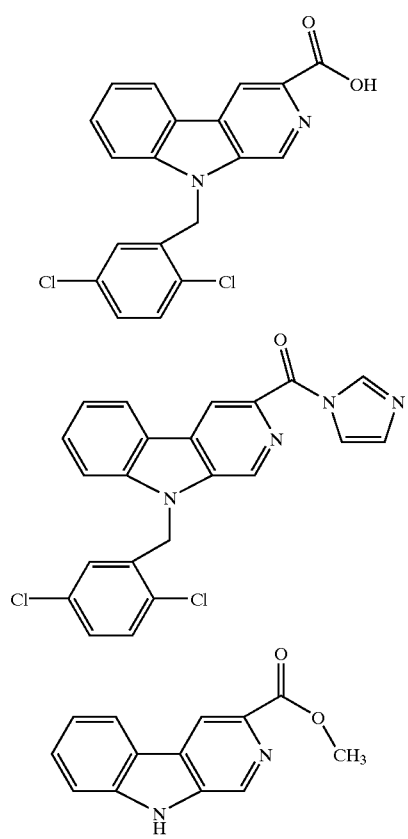

-continued

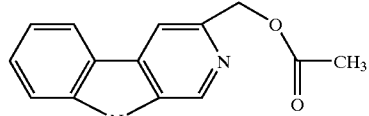

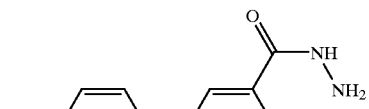

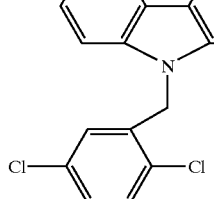

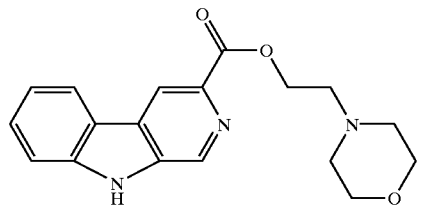

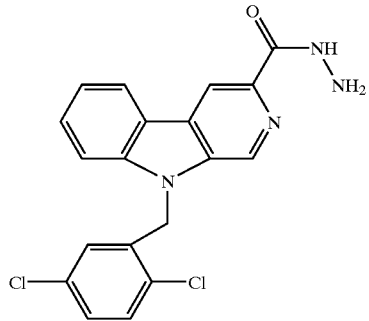

and

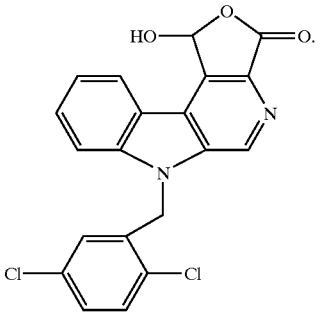

The compounds of the present invention include prodrugs, pharmaceutically acceptable salts, pharmaceutically acceptable solvates, and active metabolites of compounds of the Formula (I). The salts of the compounds are pharmaceutically acceptable salts derived from inorganic or organic acids as defined above.

The invention further comprises active metabolites and prodrugs of the compounds of Formula (I). Active metabolites of the present invention have undergone modification to their chemical structure resulting from being acted on by biotransformation reactions of drug metabolizing enzymes in various organs of the body. Prodrugs are compounds that, through these various biotransformation reactions, are metabolically converted in vivo from a precursor compound to a compound of Formula (I). Examples of prodrugs include biohydrolyzable esters and amides.

Some compounds of the invention described herein contain one or more centers of asymmetry and may thus give rise to enantiomers, diastereoisomers, and other stereoisomeric forms. The present invention is meant to include all such possible stereoisomers as well as their racemic and optically pure forms. Optically active (R) and (S) isomers may be prepared using chiral synthons, chiral reagents, or resolved using conventional techniques. When the compounds described herein contain olefinic double bonds, both E and Z geometric isomers are comprehended.

The chemical formulae referred herein may exhibit the phenomenon of tautomerism. As the formulae drawings within this specification can only represent one of the possible tautomeric forms, it should be understood that the invention encompasses any tautomeric form which can be generated by employing the tools disclosed and is not limited to any one tautomeric form utilized within the formulae drawings.

Pharmaceutical Compositions and Methods of Treatment

The pharmaceutical compositions of this invention comprise an effective amount of a compound of Formula (I) and an inert pharmaceutically acceptable carrier or diluent. An "effective amount" of a compound of Formula (I) is determined to be a GLP-1 antagonistic amount, which is a concentration of the compound where the binding and/or activation of the GLP-1 receptor is inhibited. Such an amount provides therapeutic benefits for the regulation of the insulin trophic effects associated with GLP-1 binding.

The inventive pharmaceutical compositions are prepared in dosage unit form appropriate for administration to a patient in need of treatment of a disease or condition mediated by GLP-1 inhibition. Appropriate forms of administration include (but are not limited to) oral, parenteral, intravenous, intramuscular, and transdermal methods that are generally known in the art.

The compositions may be prepared by combining an effective amount of the compound of the Formula (I) with known pharmaceutical carriers or diluents according to conventional procedures. These procedures may involve mixing, granulating, compressing or dissolving the ingredients as appropriate for the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, and preferably will be from about 25 mg to about 1 g. If a liquid carrier is used, the preparation may be in the form of syrup, emulsion, soft gelatin capsule, sterile injectable solution or suspension in an ampoule or vial or nonaqueous liquid suspension.

To obtain a stable water-soluble dose form, a pharmaceutically acceptable salt of a compound of Formula (I) is dissolved in an aqueous solution of an organic or inorganic acid, such as 0.3 M solution of succinic acid, or preferably, citric acid. If a soluble salt form is not available, the compound of Formula (I) is dissolved in one or more suitable cosolvents. Examples of suitable cosolvents include (but are not limited to) alcohol, propylene glycol, polyethylene glycol 300, polysorbate 80, glycerin and the like in concentrations ranging from 0–60% of the total volume.

The composition may also be in the form of a solution of a salt form of the active ingredient in an appropriate aqueous vehicle, such as water or isotonic saline or dextrose solution.

It will be appreciated that the actual dosages of the Formula (I) compounds used in the compositions of this invention will be selected according to the particular complex being used, the particular composition formulated, the mode of administration and the particular site, and the host and condition being treated. Optimal dosages for a given set of conditions can be ascertained by those skilled in the art using conventional dosage-determination tests. For oral administration, e.g., the dose generally employed is from about 0.001 to about 1000 mg/kg body weight, with courses of treatment repeated at appropriate intervals.

Synthesis Methods

The following synthesis protocols refer to preferred intermediate compounds and final products identified in the synthesis schemes or elsewhere in the specification. The preparation of compounds of the present invention is described in detail using the following general and specific examples. Occasionally, the reaction may not be applicable as described to each compound included within the disclosed scope of the invention; the compounds for which this occurs will be readily recognized by those skilled in the art. In all such cases, the reactions can be successfully performed by routine modifications within the level of ordinary skill in the art (e.g., by reference to teachings in the art, including those cited herein), such as by appropriate protection of interfering groups, by changing to other conventional reagents, or by routine changes to reaction conditions. Alternatively, other reactions disclosed herein or otherwise conventional will be applicable to the preparation of the corresponding compounds of the invention. In the preparative methods described below: all starting materials are known, available or readily prepared from known starting materials; all temperatures are set forth in degrees Celsius; and, unless otherwise indicated, all parts and percentages are by weight.

Reagents were purchased from commercial suppliers such as Aldrich Chemical Company or Lancaster Synthesis Ltd. and were used without further purification unless otherwise indicated. Tetrahydrofuran (THF) and N,N-dimethylformamide (DMF) were purchased from Aldrich in sealed bottles and used as received. All solvents were purified using standard methods known to those skilled in the art, unless otherwise indicated.

Biological Assays

In general, the activity of the non-peptide antagonists of the present invention may be determined using a variety of assays and techniques. The GLP-1 antagonists of the present invention inhibit the binding of GLP-1 to its receptor and/or inhibit receptor activation by bound GLP-1. Thus, binding affinity studies are useful to assess the antagonistic activity of the compounds of the present invention. Binding affinity may be determined, for example, by displacement of a ligand bound to the receptor, where the ligand is labeled with a detectable label. In particular, one having ordinary skill in the art could conduct an in vitro binding study to calculate the specific binding affinity of the compounds of the present invention to the GLP-1 receptor by pretreating cells with the compounds and then challenging the pretreated cells with radioactively labeled GLP-1.

Additionally, one having ordinary skill in the art would appreciate that the activation of the GLP-1 receptor can be measured by determining the intracellular cAMP levels measured in cells treated with the compounds of the present invention. See, e.g., Montrose-Rafizadeh et al., 1997, *J. Biol. Chem.* 272(34):21201–21206. After treatment with the compounds of the present invention, the cells are challenged with GLP-1 and the intracellular cAMP levels are determined. Antagonistic activity would be represented by decreased levels of cAMP relative to a non-treated control.

In addition to these biological assays, other peripheral assays are suitable to determine the antagonistic activity of the compounds of Formula (I). For example, known assays for determining GLP-1 activity include ingestion bioassays and ANG II-stimulated thirst assays (Tang-Christensen et al., 1996, *Amer. J. Physiol.* 271(4 Pt 2):R848–R856), and lipolysis assays (Montrose-Rafizadeh et al., 1997, *J. Cell Phys.* 172(3):275–283).

Based upon the foregoing assays, one having ordinary skill in the art could determine the effectiveness of the compounds of the present invention to inhibit the binding and/or activation of the GLP-1 receptor by GLP-1. Furthermore, such studies would be useful in assessing the effective amounts of the compounds of the present invention to inhibit GLP-1 activity.

General Examples

Method A: General Procedures for N-alkylation

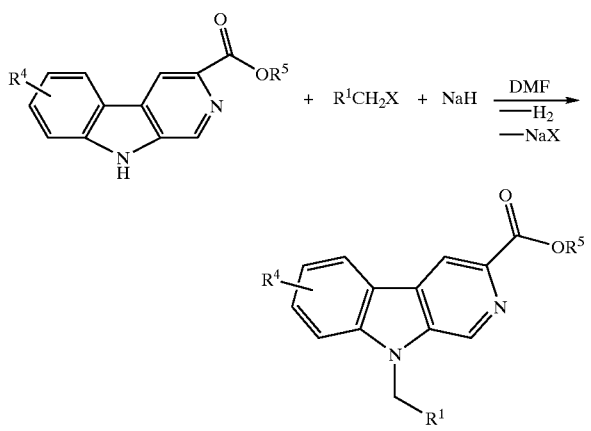

In the compounds set forth above, $R^1$, $R^4$, and $R^5$ are as defined above.

To a solution of alkyl halides in DMF (1 equiv) is added a DMF solution of substituted methyl 9H-β-carboline-3-carboxylate (1 equiv) and a suspension of sodium hydride in DMF (~1 equivalent of 60% NaH in oil) is added to the mixture. The mixture is covered, briefly agitated and shaken briefly every 15 minutes for approximately one hour. The DMF is removed in vacuo.

Method B: N-Alkylation

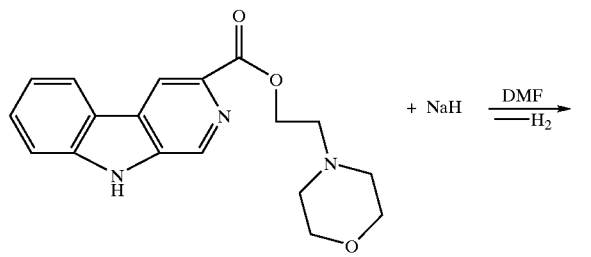

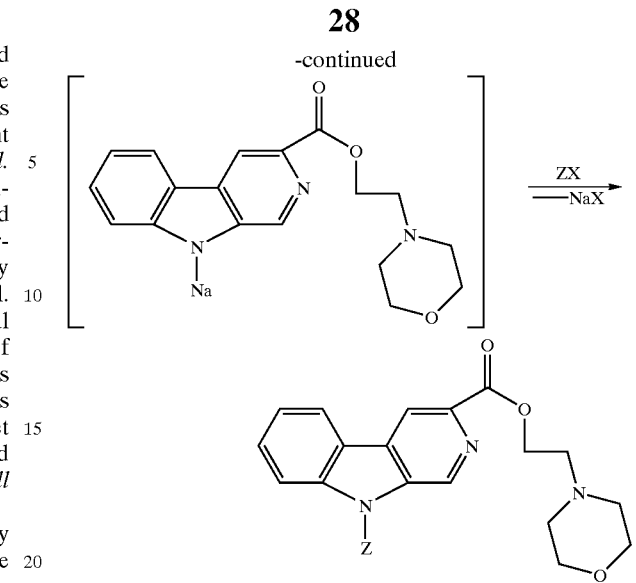

In the above compounds, Z represents —$CH_2R^1$, which is as defined above.

A mixture of a methyl 9H-β-carboline-3-carboxylate or derivative (5.0 mmol) and sodium hydride (0.20 g of 60% in oil, 5.0 mmol) is treated with dry DMF (11 mL) under nitrogen. After stirring for 15 minutes, gas evolution is essentially complete, affording a light brown, nearly clear solution of the sodium salt of the β-carboline (~0.40 M), with a trace of solid material still remaining. This solution is similarly prepared by addition of the solid β-carboline to a slurry of sodium hydride in DMF, or by addition of sodium hydride to a slurry/solution of the β-carboline in DMF. Cooling to 0° C. is necessary when the reaction is carried out on a larger scale (40–80 mmol).

To the solution of the sodium salt is added a solution of an alkyl halide in DMF (5 mL of 1.0 M, 5.0 mmol, 1 equiv), resulting in a slight exotherm. After stirring at room temperature for 2–24 hours, the DMF was removed in vacuo, and the residue partitioned between water and ethyl acetate. The ethyl acetate phase is separated, dried over $Na_2SO_4$, filtered, concentrated in vacuo, and the residue crystallized from ethyl ether, ethyl acetate/ethyl ether, or ethyl acetate/petroleum ether.

Alternatively, the products are purified by chromatography on silica gel using 95:5 diethyl ether/8M $NH_3$—$CH_3OH$ or a gradient elution of 90:10 trichloromethane ($CHCl_3$)/2M $NH_3$—$CH_3OH$ in $CHCl_3$, or reverse-phase preparative HPLC, followed by recrystallization from ethyl ether or ethyl acetate/petroleum ether.

Method C: Esterification from carboxylic acid imidazolide

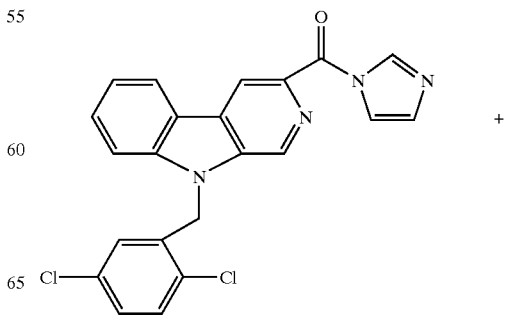

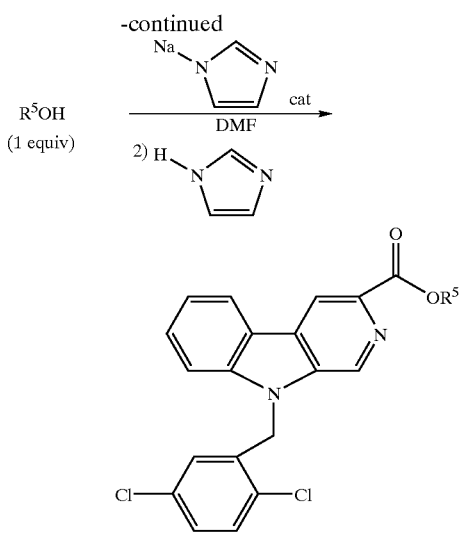

In the compounds set forth above, R₅ is as defined above.

Esterification of acids via 3-(1-imidazolylcarbonyl)-9-(2,5-dichlorobenzyl)-9H-β-carboline may be conducted by the following method (Staab, H. A., *ACIEE* 1962, 1:351). To a solution of an alcohol (125 μL of 0.40 M, 0.050 mmol) in DME (1,2-dimethoxyethane) is added a solution of a 3-(1-imidazolylcarbonyl)-9-(2,5-dichlorobenzyl)-9H-β-carboline (125 μL of 0.40 M, 0.050 mmol, 1 equiv) in DMF, followed by a solution of imidazolyl sodium (25 μL of 0.1 M, 0.0025 mmol, 5 mol %) in DMF. The latter is freshly prepared from imidazole and sodium hydride. The resulting mixture is briefly agitated and heated at 50° C. for 18–24 hours. The solvents are removed in vacuo, and the product is isolated from the residue by preparative HPLC.

Method D: Esterification of an Alcohol

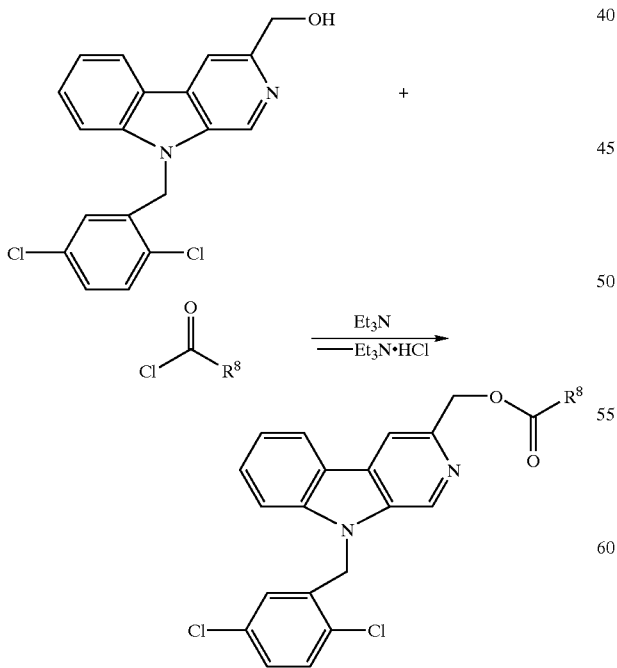

In the compounds set forth above, R⁸ is as defined above.

Esterification of an alcohol such as [9-(2,5-dichlorobenzyl)-9H-β-carbolin-3-yl]methanol (see above) may be conducted by the following method. A solution of [9-(2,5-dichlorobenzyl)-9H-β-carbolin-3-yl]methanol (100 μL of 0.5 M, 0.05 mmol) in DME is treated with a solution of an acid chloride (100 μL of 0.5 M, 0.05 mmol) in DCE (1,2-dichloroethane), and the mixture agitated briefly. A solution of triethylamine (100 μL of 1.0 M, 0.1 mmol, 2equiv) in DME is added, and the mixture is agitated again and allowed to stand at room temperature overnight. The volatiles are removed in vacuo, and the product is isolated from residue by preparative HPLC.

Method E: Esterification of a Carboxylic Acid

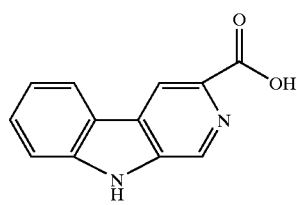

A carboxylic acid such as 9H-β-carboline-3-carboxylic acid (see above) may be esterified according to the present invention as follows. 9H-β-Carboline-3-carboxylic acid is stirred with excess SOCl₂ at room temperature overnight. The excess SOCl₂ is removed in vacuo and the resulting crude acid chloride is dissolved in CHCl₃. To this solution is added Et₃N (3 equiv) and an alcohol (5 equiv), and the resulting mixture is stirred at room temperature overnight. The reaction mixture is subjected to an aqueous workup, and the residue from the organic phase is chromatographed on silica gel (CH₂Cl₂) affording the ester.

SPECIFIC EXAMPLES

Example 1

Preparation of Methyl 9H-β-carboline-3-carboxylate

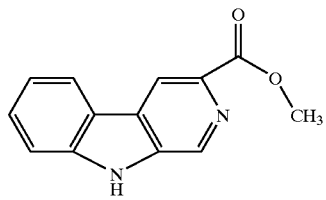

This compound was prepared by a modification of a known procedure (Couts et al., *Heterocycles* 1984, 22:131). To a mixture of the free base of L-tryptophan methyl ester (161 g, 0.738 mol) and paraformaldehyde (22 g, 0.733 mol) was added toluene (1 L). The mixture was refluxed with efficient mechanical stirring, and the water removed using a Barrett trap. After 1 hour, nearly the theoretical amount of water was collected (13 mL). Trifluoroacetic acid (5 mL, 0.065 mol, 8.8 mol %) was added through the top of the condenser (exothermic), and the mixture refluxed for another 1.5 hours. The solvent was evaporated and 10% palladium-on-carbon was added to the pot (44 g of moist material recovered from a previous run; dry wt=38 g based on water removed in subsequent step; ~0.036 mol Pd, or 4.8 mol %). Xylene (800 mL) was added, and the mixture vigorously stirred (mechanical stirrer) and refluxed overnight with a Barrett trap to remove the water from the Pd/C. The reaction mixture was then cooled in an ice bath, then in a freezer at −20° C. overnight. The resulting sludge was filtered, affording mother liquors containing impurities, including a compound consistent with methyl 2-methyl-1,2,3,4-tetrahydro-9H-β-carboline-3-carboxylate, and a gray filter cake containing a mixture of the product and Pd/C. The filter cake was transferred to a paper thimble and extracted in a Soxhlet apparatus with methanol (800 mL in a 2-L recovery flask) in several batches. As the product crystallized in the pot, the slurry was filtered, the light yellow solid was washed with methanol and dried, and the filtrate was returned to the pot. Three batches of product were collected, affording a total of 76 g of product (46% yield from tryptophan methyl ester).

Example 2

Preparation of Ethyl 9-(2,5-dichlorobenzyl)-9H-β-carboline-3-carboxylate

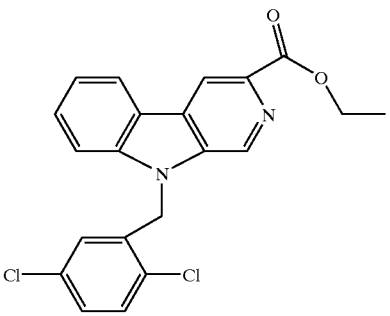

A suspension of ethyl 9H-β-carboline-3-carboxylate (2.40 g, 10 mmol) in anhydrous DMF (20 mL) was cooled in an ice bath under nitrogen. Sodium hydride (420 mg of 60% NaH in mineral oil, 10.5 mmol) was added at once, and the mixture stirred until most of the solids dissolved and hydrogen evolution stopped (approx 10 min). The cool mixture was treated with 2,5-dichlorobenzyl chloride (2.15 g, 1.0 mmol) slowly with stirring, then allowed to warm to room temperature over two hours. The resulting cloudy solution was neutralized with acetic acid, then the solvent was removed in vacuo, affording a tan solid (3.94 g). The crude material was chromatographed on silica gel using a mixture of chloroform and ethyl acetate, affording the title product (1.96 g, 49%). $^1$H NMR (300 MHz, DMSO-$d_6$) δ9.06 (s, 1 H), 8.96 (s, 1H), 8.48 (d, J=8.0, 1H), 7.55–7.64 (m, 3H), 7.35–7.42 (m, 2H), 6.60 (d,J=2.3, 1H), 5.89 (s, 2H), 4.36 (q, J=6.9, 1H), 1.35 (t, J=7.2, 3H); LRMS calcd for $C_{21}H_{16}Cl_2N_2O_2$ (M+H) 399, found 399.0.

Example 3

Preparation of 9-(2,5-Dichlorobenzyl)-9H-β-carboline-3-carboxylic acid

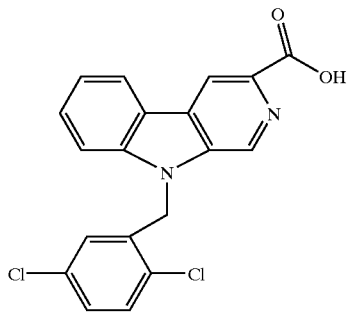

9-(2,5-Dichlorobenzyl)-9H-β-carboline-3-carboxylic acid was prepared as described for the corresponding 9-unsubstituted compound (Hagen et al., *Heterocycles* 1986, 24:2845). A mixture of methyl 9-(2,5-dichlorobenzyl)-9H-β-carboline-3-carboxylate (15.0 g, 0.0389 mol), sodium hydroxide (2.0 g, 0.05 mol), water (75 mL), and 95% ethanol (200 mL) was refluxed for 1 hour. The mixture was concentrated in vacuo, and the residue dissolved in warm water (500 mL), and the pH adjusted to 3 using dilute HCl with vigorous stirring, resulting in the precipitation of a solid. The fine slurry was filtered, washed thoroughly with water, and dried in vacuo overnight at 70° C., and for another day at 85° C., affording 12.60 g (87%) of product. In another run, the product was isolated in 82% yield after recrystallization from hot acetic acid. The product had the following properties: $^1$H NMR (300 MHz, DMSO-$d_6$) δ9.16 (s, 1H), 9.08 (s, 1H), 8.59 (d, J=8.0, 1H), 7.60–7.69 (m, 3H), 7.39–7.44 (m, 2H), 6.705 (d, J=2.3, 1H), 5.93 (s, 2H), 1.93 (s, 3H); LRMS calcd for $C_{19}H_{10}Cl_2N_2O_2$ (M+H) 371, found 371.0.

Example 4

Preparation of 3-(1-Imidazolylcarbonyl)-9-(2,5-dichlorobenzyl)-9H-β-carboline

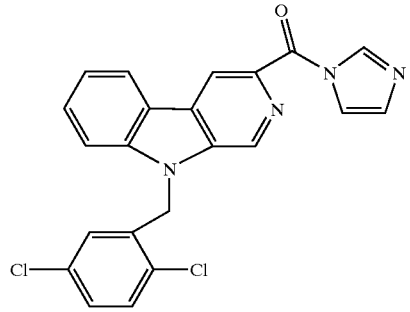

To a suspension of 9-(2,5-dichlorobenzyl)-9H-β-carboline-3-carboxylic acid (4.55 g, 0.0123 mol) in dry DMF (100 mL) was added 1,1-carbonyldiimidazole (3.77 g, 0.0233 mol), resulting in the formation of an opaque, yellow solution. The reaction was stirred at room temperature under nitrogen for 5 hours. Cold water (800 mL) was added, and the resulting precipitate filtered, washed with cold water, and dried in vacuo, affording 4.85 g (94%) of the product as a white solid. $^1$H NMR (CDCl$_3$) δ9.13 (s, 1H), 9.12 (s, 1H), 8.87 (s, 1H), 8.33 (d, J=7.9 Hz, 1H), 8.08 (s, 1H), 7.71 (t, J=7.7 Hz, 1H), 7.52–7.45 (m, 3H), 7.28–7.25 (m, 1H), 7.16 (s, 1H), 6.56 (d, J=2.2 Hz, 1H), 5.74 (s, 2H). MS (APCI; (M+H)$^+$) m/z 421.

Example 5

Preparation of Isopropyl 9-(2,5-dichlorobenzyl)-9H-β-carboline-3-carboxylate

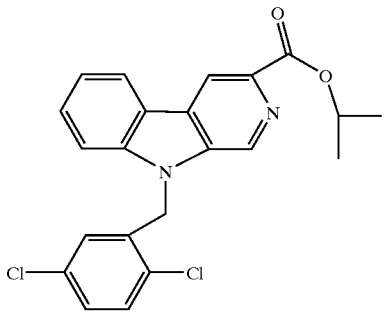

A mixture of 9-(2,5-dichlorobenzyl)-9H-β-carboline-3-carboxylic acid acetate salt (1.30 g, 3.02 mmol) and thionyl chloride (2.2 mL, 30 mmol) was stirred and refluxed for 2 hours. The reaction mixture was concentrated in vacuo and the resulting dark oil was used without further purification. The oil was dissolved in 15 mL of DMF (theor. 0.2M). A portion (2.5 mL, 0.5 mmol) of this solution was added to a large excess of isopropanol and triethylamine and the resulting mixture stirred at 60° C. overnight. After cooling to room temperature, the mixture was shaken with methylene chloride, and the mixture was washed with water and brine. The organic phase was dried with anhydrous sodium sulfate and the solvent removed in vacuo. Purification by flash chromatography on silica gel afforded the product as an oil (144 mg, 70%). $^1$H NMR (300 MHz, DMSO-d$_6$) δ8.80 (s, 1H), 8.75 (s, 1H), 8.13–8.16 (m, 1H), 7.50–7.56 (m, 1H), 7.20–7.33 (m, 3H), 7.08 (dd, J=2.6, 8.7, 1H), 6.48 (d, J=2.3, 1H), 5.48 (s, 2H), 5.37 (septet, J=6.4, 1 H), 1.43 (d, J=6.4, 6H).

Example 6

Preparation of 9H-β-carbolin-3-ylmethyl acetate

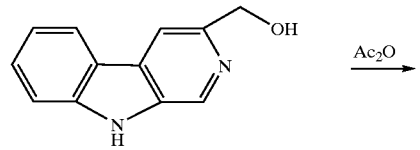

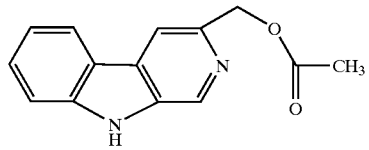

A suspension of 9H-β-carboline-3-methanol (99 mg, 0.50 mmol) in acetic anhydride (10 mL) was stirred for 4 hours at room temperature, during which time the starting material dissolved. Removal of the acetic anhydride in vacuo afforded a tan solid (122 mg). Purification by flash chromatography on silica gel with ethyl acetate as the eluent afforded 82 mg (68%) of the title compound. $^1$H NMR (300 MHz, DMSO-d$_6$) δ9.49 (s, 1H), 8.99 (s, 1H), 8.13 (d, J=8.0, 1H), 8.07 (s, 1H), 7.56–7.61 (m, 2H), 7.26–7.34 (m, 1H), 5.43 (s, 2H), 2.15 (s, 3H). LRMS calcd for C$_{14}$H$_{12}$N$_2$O$_2$ (M+H) 241, found 241.0.

Example 7

Preparation of [9-(2,5-Dichlorobenzyl)-9H-β-carbolin-3-yl]methyl acetate

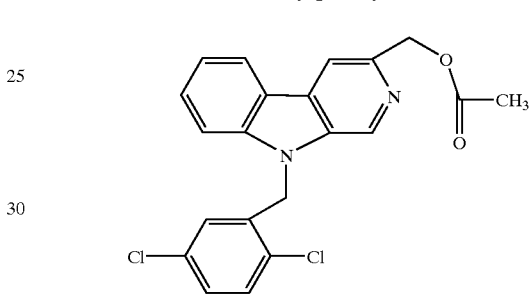

[9-(2,5-Dichlorobenzyl)-9H-β-carbolin-3-yl]methyl acetate was prepared from 3-acetoxymethyl-9H-pyrido[3,4-b]indole using Method A. Purification by flash chromatography on silica gel with chloroform/ethyl acetate eluent afforded the product in 89% yield. $^1$H NMR (300 MHz, DMSO-d$_6$) δ8.72 (s, 1 H), 8.19 (d, J=7.9, 1H), 8.09 (s, 1H), 7.55–7.61 (m, 1H), 7.28–7.39 (m, 3H), 7.18 (dd, J=2.3, 8.7, 1H), 6.51 (d, J=2.3, 1H), 5.54 (s, 2H), 5.42 (s, 2H), 2.19 (s, 3H).

Example 8

Preparation of Methyl 9-(2,5-dichlorobenzyl)-9H-β-carboline-3-carboxylate

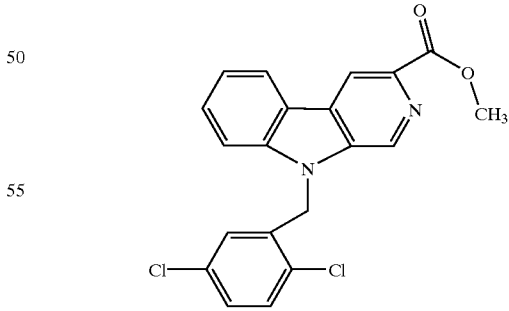

To a suspension of sodium hydride (1.60 g of 60% dispersion in oil, 0.04 mol) in dry DMF (60 mL) was added methyl 9H-β-carboline-3-carboxylate (8.7 g, 0.0385 mol) at −20° C. with stirring. The mixture was allowed to warm to room temperature with stirring under nitrogen. After stirring for 10 minutes at room temperature, formation of the sodium salt of the β-carboline appeared to be complete, resulting in a clear brown solution. The reaction mixture was cooled in an ice bath, 2,5-dichlorobenzyl chloride (7.82 g, 0.040 mol) was added, and the mixture was allowed to warm to room temperature and stirred overnight. The reaction mixture was diluted with water (200 mL), filtered, and the cake washed with water, ethyl acetate, ether, and dried, affording 13.05 g (88%) of the title product. $^1$H NMR (CDCl$_3$) δ8.88 (s, 1H), 8.78 (s, 1H), 8.20 (d, J=7.8 Hz, 1H), 7.61 (t, J=7.8 Hz, 1H), 7.45–7.35 (m, 3H) 7.18 (dd, J=8.2, 1.7 Hz,1H), 6.52 (s, 1H), 5.56 (s, 2H), 4.06 (s, 3H); MS (APCI; (M+H)$^+$) m/z 385.

Example 9

Preparation of [9-(2,5-Dichlorobenzyl)-9H-β-carbolin-3-yl]methanol

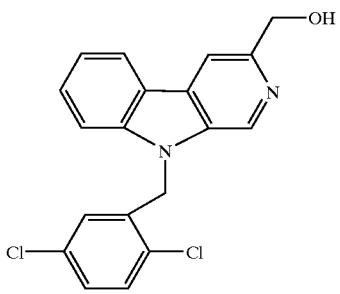

A mixture of methyl 9-(2,5-dichlorobenzyl)-9H-β-carboline-3-carboxylate (13.05 g, 0.0339 mol), and sodium borohydride (3 g, 0.079 mol) was stirred and refluxed in anhydrous ethanol (200 mL) for 15 h. The ethanol was evaporated, and the residue partitioned between 10% aqueous Na$_2$CO$_3$ (100 mL) and methylene chloride (100 mL). The organic phase was dried over MgSO$_4$, evaporated, and the residue crystallized from ether, affording the title product as an ivory-colored solid (11 g, 91%).

In an alternative synthesis, a solution of [9-(2,5-dichlorobenzyl)-9H-β-carbolin-3-yl]methyl acetate (53.4 mg, 0.13 mmol) in methanol (2 mL) was treated with potassium hydroxide (54 mg, 0.96 mmol) and stirred, resulting in nearly immediate hydrolysis, as evidenced by TLC and flow-injection MS. The product was isolated by flash chromatography on silica gel using 10:1 chloroform/methanol affording 35 mg (75%) of the pure product. $^1$H NMR (CDCl$_3$) 67 8.58 (s, 1H), 8.10 (d, J=9.0Hz, 1H), 7.91 (s, 1H), 7.50 (td, J=7.7 Hz, 1H), 7.23–7.32 (6-line multiplet, 2H), 7.10 (dd, J=8.5 Hz, 2.4 Hz, 1H), 6.41 (d, J=2.4Hz, 1H), 5.48 (s, 2H), 4.87 (s, 2H), 3.62–3.77 (br. s, 1H); MS monoisotopic mass (calculated) 355.9, MH$^+$ (observed) 357.0.

Example 10

Preparation of 2-(Dimethylamino)ethyl 9-2,5-dichlorobenzyl)-9-β-carboline-3-carboxylate

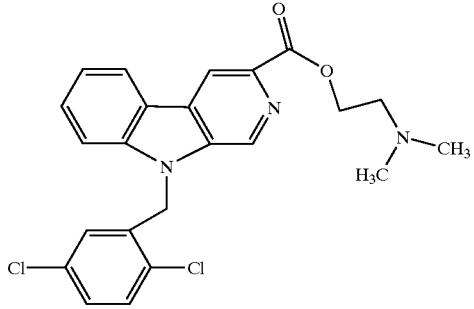

2-(Dimethylamino)ethyl 9-(2,5-dichlorobenzyl)-9H-β-carboline-3-carboxylate was prepared according to Method D. $^1$H NMR (CDCl$_3$) 67 8.96 (s, 1H), 8.82 (s, 1H), 8.26 (d, J=8.2 Hz, 1H), 7.62 (m, 1H), 7.59–7.66 (m, 3H), 7.19 (d,J=6.2 Hz, 1H), 6.52 (s, 1H), 5.61 (d, J=8.4 Hz, 2H), 4.58 (t, J=6.0 Hz, 2H), 2.81 (t,J=6.1 Hz, 2 H), 2.81 (t,J=6.1 Hz, 2H), 2.37 (s, 6H); MS (APCI; (M+H)$^+$) m/z 441.

Example 11

Preparation of 2-Methoxyethyl 9-(2,5-dichlorobenzyl)-9H-β-carboline-3-carboxylate

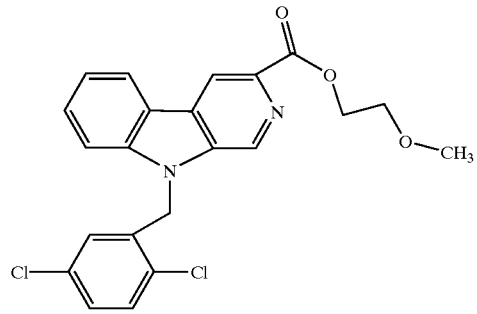

2-Methoxyethyl 9-(2,5-dichlorobenzyl)-9H-β-carboline-3-carboxylate was prepared according to Method D. $^1$H NMR (CDCl$_3$) δ8.95 (s, 1H), 8.85 (s, 1H), 8.27 (d, J=7.8 Hz, 1H), 7.62 (t,J=7.4 Hz, 1H), 7.41 (m, 3H), 7.21 (t,J=2.4 Hz, 1 H), 6.54 (s, 1H), 5.67 (s, 2H), 4.64 (t,J=5.0 Hz, 2H), 3.83 (t,J=3.7 Hz, 2H), 3.46 (s, 3H); MS (APCI; (M+H)$^+$) m/z 429.

Example 12

Preparation of 2-Hydroxyethyl 9-(2,5-dichlorobenzyl)-9H-β-carboline-3-carboxylate

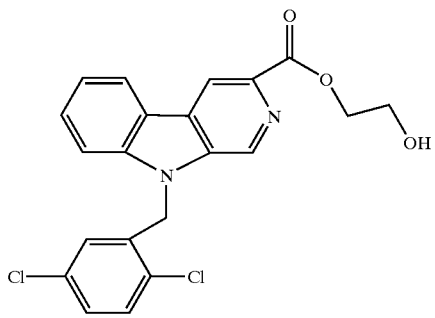

2-Hydroxyethyl 9-(2,5-dichlorobenzyl)-9H-β-carboline-3-carboxylate was prepared according to Method D. $^1$H NMR (CDCl$_3$) 67 8.83 (s, 1H), 8.82 (s, 1H), 8.15 (d, J=7.8 Hz, 1H), 7.62 (t, J=7.2 Hz, 1H), 7.41 (m, 3H), 7.21 (d,J=6.1 Hz, 1H), 6.49 (s, 1H), 5.54 (s, 2H), 4.61 (t,J 4.7 Hz, 2H), 4.26 (br s, 1H), 4.08 (t,J=3.5 Hz, 2H); MS (APCI; (M+H)$^+$) m/z 415.

Example 13

Preparation of 9-(2,5-Dichlorobenzyl)-3-(3-methyl-1,2,4-oxadiazol-5-yl)-9H-β-carboline

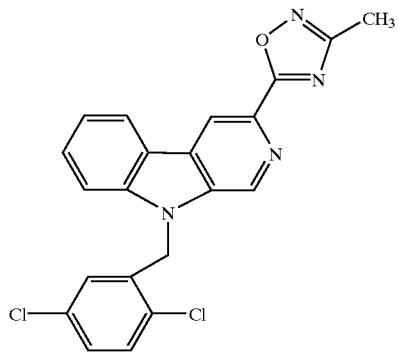

A slurry of sodium hydride (40 mg of 60 wt % in mineral oil, 1.0 mmol), acetamidoxime (74 mg, 1.0 mmol), and powdered 3 Å molecular sieves (200 mg) in THF (3 mL) was stirred and refluxed for 30 minutes. To this was added methyl 9-(2,5-dichlorobenzyl)-9H-β-carboline-3-carboxylate (193 mg, 0.50 mmol), using an additional 2 mL of THF to transfer it quantitatively to the flask. The resulting slurry was stirred and refluxed until the reaction was complete by TLC (1.5 hours or less). The reaction mixture was filtered through 10 cc of silica gel in a fritted glass funnel, using THF as the eluent, affording 193 mg of the crude oxadiazole after evaporation of the solvent. The product was purified by preparative TLC using 1:1 ethyl acetate/petroleum ether, affording 79 mg (39%) of the pure title compound. $^1$H NMR (CDCl$_3$) δ8.96 (s, 1H), 8.92 (s, 1H), 8.28 (d,J=7.5Hz, 1H), 7.66 (t, J=7.5 Hz, 1H), 7.47–7.41 (m, 3H), 7.23 (dd, J=8.5, 2.3 Hz, 1H), 6.57 (d, J=2.3 Hz, 1H), 5.70 (s, 2H), 2.54 (s, 3H); MS (APCI; (M+H)$^+$) m/z 409.

Example 14

Preparation of Butyl 9-(2,5-Dichlorobenzyl)-9H-β-carboline-3-carboxylate

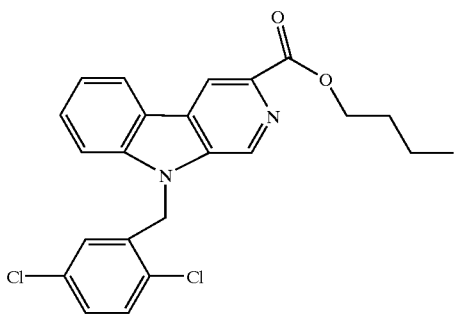

Methyl 9-(2,5-dichlorobenzyl)-9H-β-carboline-3-carboxylate (195 mg, 0.5 mmol), was heated with n-butanol (15 mL) and concentrated sulfuric acid; the mixture was distilled slowly over 45 minutes, after which time the reaction appeared complete by TLC. The reaction mixture was partitioned between aqueous sodium carbonate and ethyl acetate, the organic phase was dried over sodium sulfate, filtered, evaporated, and the residue recrystallized from ethyl acetate/petroleum ether. From this was isolated 318 mg of a white solid whose $^1$H NMR was consistent with sodium butyl sulfate. The filtrate was filtered through silica gel using 1:1 ethyl acetate/petroleum ether, and the filtrate recrystallized from a minimum amount of ethyl acetate and petroleum ether, affording the product as an ivory-colored solid (119 mg, 56%). $^1$H NMR (CDCl$_3$) δ8.93 (s, 1H), 8.85 (s, 1H), 8.28 (d, J=8.3 Hz, 1H), 7.64 (ddd, J=8.3, 7.2, 1.1 Hz, 1H), 7.45–7.39 (m, 3H), 7.21 (dd,J=8.5, 2.4 Hz, 1H), 6.54 (d, J=2.3 Hz, 1H), 4.49 (t, J=7 Hz, 2H), 1.87 (m, 2H), 1.51 (m, 2H), 1.01 (t,J=7 Hz, 3H); MS (APCI; (M+H)$^+$) m/z 427.

Example 15

Preparation of Propyl 9-(2,5-Dichlorobenzyl)-9H-β-carboline-3-carboxylate

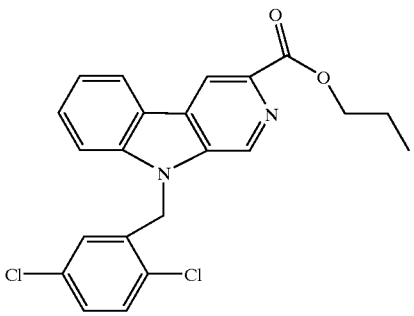

Methyl 9-(2,5-dichlorobenzyl)-9H-β-carboline-3-carboxylate (195 mg, 0.5 mmol) was refluxed with n-propanol (15 mL) and concetrated sulfuric acid (1.5 mL) as described for the synthesis of the butyl 9-(2,5-dichlorobenzyl)-9H-β-carboline-3-carboxylate, affording an ivory-colored solid (152 mg, 74%). $^1$H NMR (CDCl$_3$) δ8.94 (s, 1H), 8.85 (s, 1H), 8.28 (d, J=8.3 Hz, 1H), 7.64 (t, J=7.5 Hz, 1H), 7.45–7.40 (m, 3H), 7.22 (dd, J=8.5, 2.3 Hz, 1H), 6.55 (s, 1H), 5.66 (s, 2H), 4.45 (t,J=7 Hz, 2H), 1.93 (m, 2H), 1.07 (t, J=7 HZ, 3H); MS (APCI; (M+H)$^+$) m/z 413.

Example 16

Preparation of Ethyl 9-[(5,6-Dichloro-3-pyridyl)methyl]-9H-β-carboline-3-carboxylate

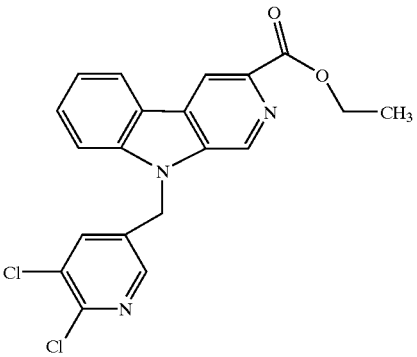

Ethyl 9-[(5,6-Dichloro-3-pyridyl)methyl]-9H-β-carboline-3-carboxylate was prepared by Method A, and purified by preparative thin layer chromatography (TLC). $^1$H NMR (300 MHz, DMSO-d$_6$) δ8.91 (s, 2H), 8.23–8.26 (m, 2H), 7.59–7.68 (m, 1H), 7.39–7.45 (m, 3H), 5.62 (s, 2H), 4.53 (q, J=7.2, 2H), 1.49 (t,J=7.2, 3H); LRMS calcd for C$_{20}$H$_{15}$Cl$_2$N$_3$O$_2$ (M+Cl−) 434, found 433.9.

Example 17

Preparation of Ethyl 9-(3,5-dinitrobenzyl)-9H-β-carboline-3-carboxylate

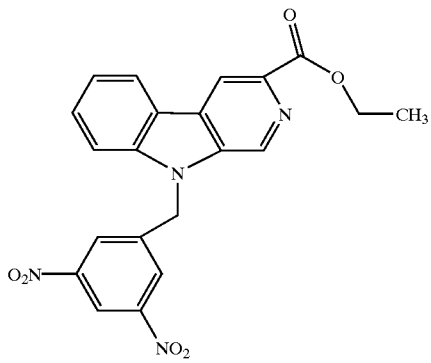

Ethyl 9-(3,5-dinitrobenzyl)-9H-β-carboline-3-carboxylate was prepared by Method A, and purified by preparative thin layer chromatography (yield: 66%). $^1$H NMR (300 MHz, DMSO-$d_6$) δ8.95 (s, 2H), 8.90 (s, 1H), 8.31 (s, 3H), 7.65–7.67 (m, 1H), 7.41–7.49 (m, 2H), 5.86 (s, 2H), 4.54 (q, J=7.1, 2H), 1.50 (t, J=7.1, 3H), LRMS calcd for $C_{21}H_{16}N_4O_6$ (M–H) 419, found 419.0.

Example 18

Preparation of Ethyl 9-(3-nitrobenzyl)-9H-β-carboline-3-carboxylate

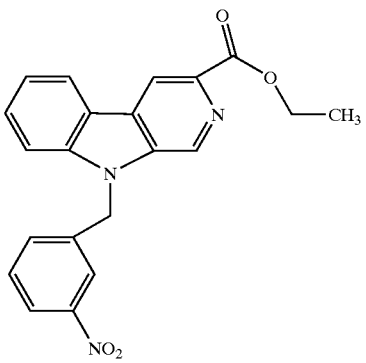

Ethyl 9-(3-nitrobenzyl)-9H-β-carboline-3-carboxylate was prepared by Method A, and purified by preparative thin layer chromatography (yield: 39%). $^1$H NMR (300 MHz, DMSO-$d_6$) δ8.90 (s, 1H), 8.88 (s, 1H), 8.24 (d, J=7.9, 1H), 8.08–8.13 (m, 2H), 7.61–7.66 (m, 1H), 7.35–7.46 (m, 4H), 5.72 (s, 2H), 4.52 (q, J=7.1, 2H), 1.49 (t, J=7.1, 3H); LRMS calcd for $C_{21}H_{17}N_3O_4$ (M–H) 374, found 374.0.

Example 22

Preparation of 6-(2,5-dichlorobenzyl)-1-methyl-1,6-dihydro-3H-furo[3',4':5,6]pyrido[3,4-b]indol-3-one

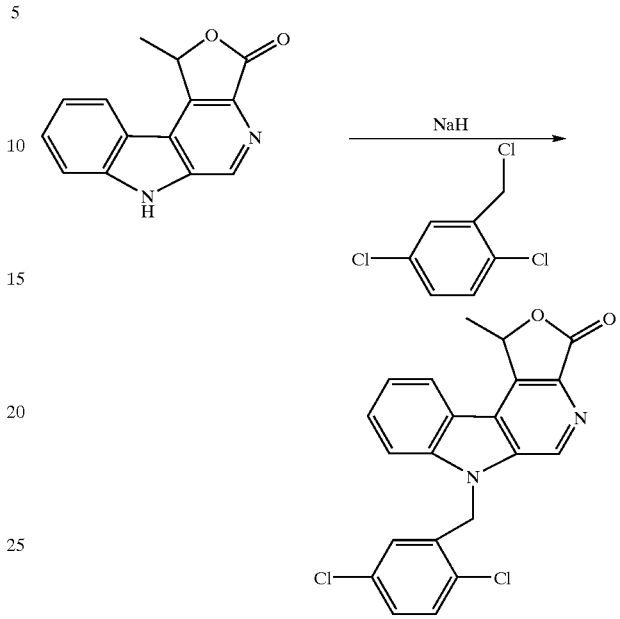

6-(2,5-Dichlorobenzyl)-1-methyl-1,6-dihydro-3H-furo[3',4':5,6]pyrido[3,4-b]indol-3-one was prepared using Method A from 1-methyl-1,6-dihydro-3H-furo[3',4':5,6]pyrido[3,4-b]indol-3-one (9 mg, 0.038 mmol), NaH (0.046 mmol, 2 mg of 60 wt. % suspension in mineral oil) and 2,5-dichlorobenzyl chloride (9 mg, 0.046 mmol) in DMF (1 mL). Purification of the crude product by preparative thin layer chromatography with hexane/ether (2:1) as eluent furnished the desired product (5 mg, 33% yield) as a yellow solid. $^1$H NMR (CDCl$_3$) δ8.93 (s, 1H), 8.09 (d, J=8.0 Hz, 1H), 7.65 (t, J=7.8 Hz, 1H), 7.37–7.46 (m, 3H), 7.16 (d, J=2.2 Hz, 1H), 6.42 (d, J=2.2 Hz, 1H), 6.05 (q, J=6.6 Hz, 1H), 5.70 (s, 2H), 1.92 (d, J=6.6 Hz, 3H); MS (APCI; (M+H)$^+$) m/z 397.

Example 23

Preparation of 2-(4-Morpholinyl)ethyl 9-(3,5-dinitrobenzyl)-9H-β-carboline-3-carboxylate

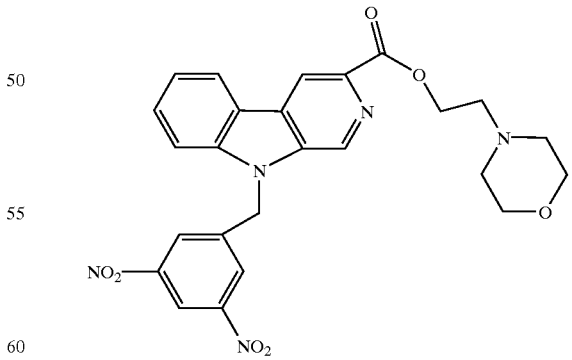

2-(4-Morpholinyl)ethyl 9-(3,5-dinitrobenzyl)-9H-β-carboline-3-carboxylate was prepared according to Method A. $^1$H NMR (CDCl$_3$) δ8.93 (m, 2H), 8.86 (s, 1H), 8.28 2,5-dichlorobenzyl chloride (80 mg, 0.41 mmol) in DMF (2 mL) was treated according to Method A. Purification of the crude product by column chromatography on silica with hexane/ether (1:1) as eluent furnished the desired product (90 mg, 60% yield) as a pale yellow solid. $^1$H NMR (CDCl$_3$) δ8.64 (s, 1H), 8.25 (d, J=7.5Hz, 1H), 7.49 (t, J=7.7 Hz, 1H), 7.18–7.31 (m, 2H), 7.05–7.11 (m, 2H), 6.38 (s, 1H), 5.23 (s, 2H), 5.20–5.23 (m,1H), 3.40 (s, 3H), 1.33 (d, J=6.3 Hz, 6H); MS (APCI; (M+H)$^+$)m/z 457.

Example 21

Preparation of Ethyl 6-amino-9-(2,5-dichlorobenzyl)-9H-β-carboline-3-carboxylate

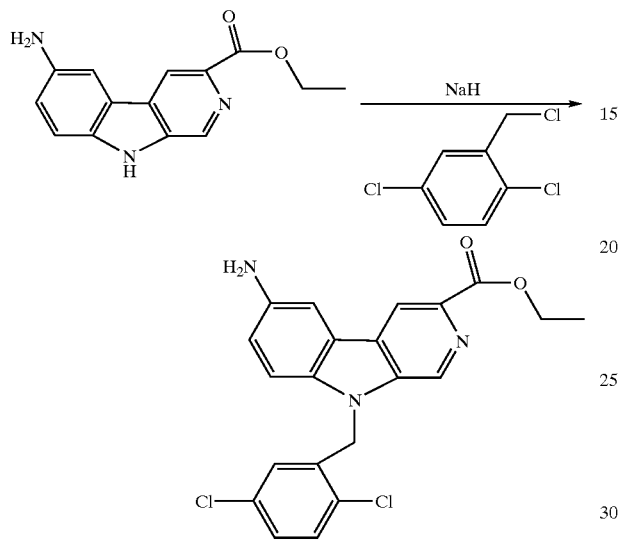

A mixture of ethyl 6-amino-9H-β-carboline-3-carboxylate (100 mg, 0.39 mmol), NaH (0.58 mmol, 24 mg of 60 wt. % suspension in mineral oil) and 2,5-dichlorobenzyl chloride (115 mg, 0.59 mmol) in DMF (2 mL), was treated according to Method A. Purification of the crude product by column chromatography on silica with hexane/ethyl acetate (7:3) as eluent furnished the desired product (87 mg, 54% yield) as a yellow solid. $^1$H NMR (DMSO-d$_6$) δ8.96 (s, 1H), 8.74 (s,1H), 7.60 (d,J=8.6 Hz, 1H), 7.48 (d, 1H), 7.41 (dd, J=8.4 Hz, 2.1Hz, 1H), 7.35 (d, J=8.8 Hz, 1H), 7.01 (d,J=8.6 Hz, 1H), 6.51 (d, J=1.8 Hz, 1H), 5.80 (s, 2H), 5.10 (br s, 1H), 4.37 (q,J=7.0 Hz, 2H), 1.37 (t, J=7.0 Hz, 3H); MS (APCI; (M+H)$^+$) m/z 414.

Example 19

Preparation of [9-(2,5-Dichlorobenzyl)-9H-β-carbolin-3-yl]methyl cyclopropanecarboxylate

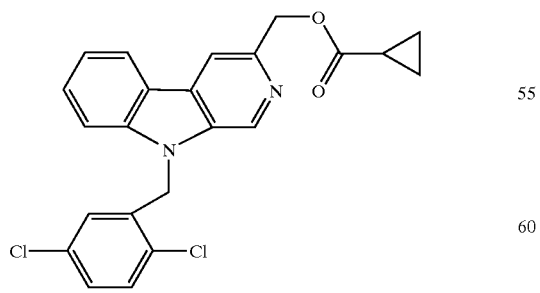

A solution of [9-(2,5-dichlorobenzyl)-9H-β-carbolin-3-yl]methanol (357 mg, 1.0 mmol) and cyclopropyl carbonyl chloride (133 mg, 1.27 mmol) in methylene chloride (5 mL) was allowed to stand for 10 minutes. The solvent was evaporated, and the residue partitioned between aqueous Na$_2$CO$_3$ and methylene chloride. The extract was dried over Na$_2$SO$_4$, filtered and evaporated, affording a resin. This was dissolved in ether and filtered through a plug of silica gel, treated with ethereal hydrogen chloride, evaporated, and the residue recrystallized from ethanol/ethyl acetate/ether, affording 270 mg (58%) of the title compound as a yellow solid. $^1$H NMR (CDCl$_3$) δ8.85 (s, 1H), 8.44 (s, 1 H), 8.25 (d, J=7.9 Hz, 1H), 7.58 (t, J=7.5 Hz, 1H), 7.35–7.28 (m, 3H), 7.10 (dd, J=8, 2.3 Hz, 1H), 6.37 (d, J=2.3 Hz, 1H), 5.62 (s, 2H), 5.46 (s, 2H), 1.74 (m, 2H), 1.56 (m, 1H), 0.84–0.71 (m, 4H); MS (APCI; (M+H)$^+$) m/z 425.

Example 20

Preparation of Isopropyl 9-(2.5-dichlorobenzyl)-4-(methoxymethyl)-9H-β-carboline-3-carboxyate

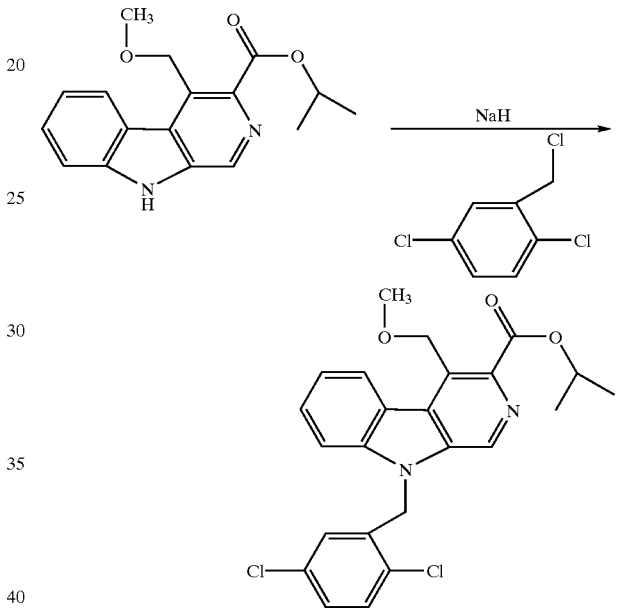

A mixture of isopropyl 4-(methoxymethyl)-9H-β-carboline-3-carboxylate (100 mg, 0.33 mmol), NaH (0.36 mmol, 15 mg of 60 wt. % suspension in mineral oil) and (m, 3H), 7.68 (t, 1H), 7.47–7.34 (m, 2H), 5.80 (s, 2H), 4.53 (t, 2H), 3.69 (m, 4H), 2.81 (t, 2H), 2.53 (m, 4H); MS (APCI; (M+H)$^+$) m/z 506.

Example 24

Preparation of 2-(4-Morpholinyl)ethyl 9-(2,5-dichlorobenzyl)-9H-β-carboline-3-carboxylate

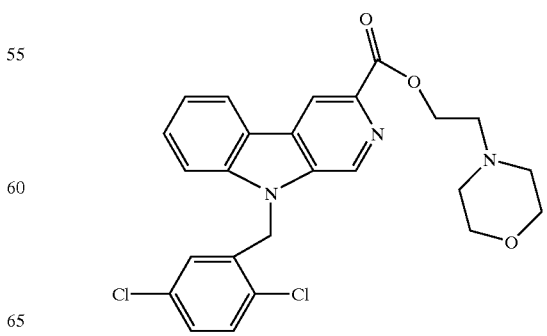

2-(4-Morpholinyl)ethyl 9-(2,5-dichlorobenzyl)-9H-β-carboline-3-carboxylate was prepared according to Method D. Following chromatographic purification, the free base was treated with ethereal hydrogen chloride, and the product isolated as the dihydrochloride salt in 11% yield after recrystallization from ethanol/ether. $^1$H NMR (DMSO-$d_6$) δ11.7 (br s, 1H), 9.63 (s, 1H), 9.42 (s, 1H), 8.75 (d,J=7.9Hz, 1H), 7.81–7.70 (m, 2H), 7.63 (d, J=8.5 Hz, 1H), 7.53 (t, J=7.4 Hz, 1H), 7.44 (dd, J=8.5, 2.4 Hz, 1H), 6.68 (d, J=2.4 Hz, 1H), 6.05 (s, 2H), 4.75 (br s, 2H, overlap with water peak), 4.00 (br s, 4H), 3.60 (br s, 4H), 3.22 (br s, 2H); MS (APCI; (M+H)$^+$) m/z 484.

Example 25

Preparation of Ethyl 9-(2-methoxy-5-nitrobenzyl)-9H-β-carboline-3-carboxylate

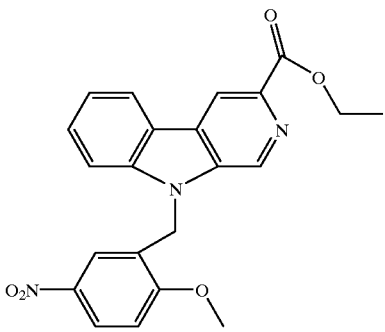

Ethyl 9-(2-methoxy-5-nitrobenzyl)-9H-β-carboline-3-carboxylate was prepared according to Method A. The product was purified by reverse-phase HPLC. $^1$H NMR (CDCl$_3$) δ8.94 (s, 1H), 8.91 (s, 1H), 8.23–8.13 (m, 2H), 7.66 (s, 1H), 7.63 (m, 1H), 7.44 (d, J=7.5 Hz, 1H), 7.32 (t,J=7.5 Hz, 1H), 6.96 (d,J=8.5 Hz, 1H), 5.60 (s, 2H), 4.52 (q, J=6.7 Hz, 2H), 3.93 (s, 3H), 1.51 (t, J=6.7 Hz, 3H); MS (APCI; (M+H)$^+$) m/z 406.

Example 26

Preparation of [9-(2,5-Dichlorobenzyl-9H-β-carbolin-3-y]methyl 2-chloronicotinate

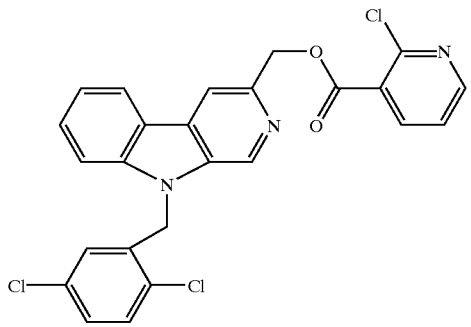

[9-(2,5-Dichlorobenzyl-9H-β-carbolin-3-yl]methyl 2-chloronicotinate was prepared according to Method C, and purified by reverse-phase HPLC. The product was isolated as the free base. $^1$H NMR (CDCl$_3$) δ8.77 (s, 2H), 8.51 (dd, J=4.6, 2.0 Hz, 1H), 8.29–8.21 (m, s, overlap, 3H), 7.60 (t,J=7.8 Hz, 1H), 7.42–7.29 (m, overlap 3H), 7.21 (dd, J=8.5, 2.3 Hz, 1H), 6.50 (s, 1H), 5.63 (s, 2H), 5.59 (s, 2H); MS (APCL; (M+H)$^+$) m/z 496.

Example 27

Preparation of [9-(2,5-Dichlorobenzyl)-9H-β-3-carbolin-3-yl]methyl nicotinate

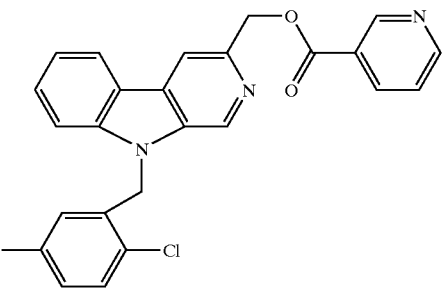

[9-(2,5-Dichlorobenzyl)-9H-β-carbolin-3-yl]methyl nicotinate was prepared according to Method C, and purified by preparative TLC. The product was isolated as the hydrochloride salt upon treatment of the free base with ethereal hydrogen chloride, followed by recrystallization from ethanol/ether (overall yield: 43%). $^1$H NMR (DMSO-$d_6$) δ9.61 (s, 1H), 9.40 (s, 1H), 9.18 (s, 1H), 9.02 (d, 1H), 8.75 (m, 2H), 7.8–7.39 (m, 6H), 6.70 (s, 1H), 6.03 (s, 2H), 5.89 (s, 2H) (note: the acidic hydrogens, including the water in the solvent, were not observed, presumably due to severe broadening); MS (APCL; (M+H)$^+$) m/z 462.

Example 28

Preparation of Isopropyl 9-(3,5-dinitrobenzyl)-4-(methoxymethyl)-9H-β-carboline-3-carboxylate

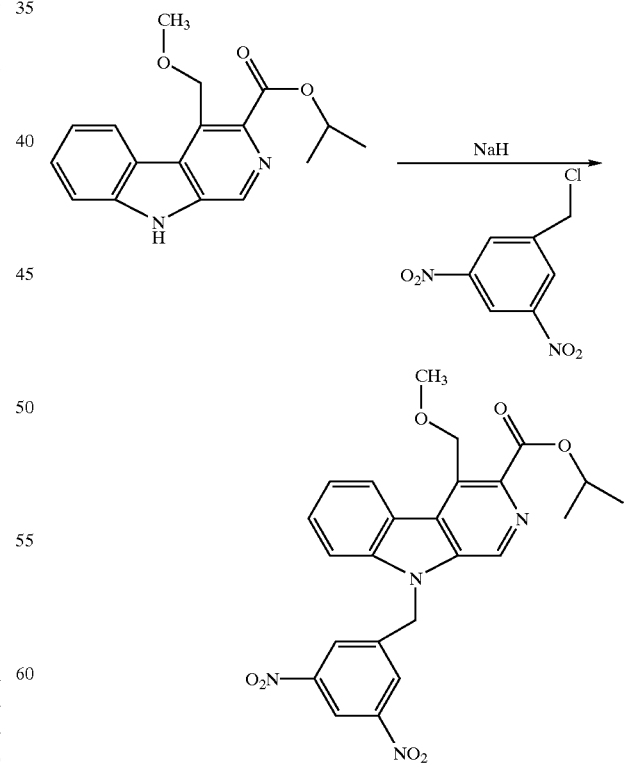

Isopropyl 9-(3,5-dinitrobenzyl)-4-(methoxymethyl)-9H-β-carboline-3-carboxylate was prepared from isopropyl 4-(methoxymethyl)-9H-β-carboline-3-carboxylate according to Method A, in 44% yield. The free base was treated with ethereal hydrogen chloride, and the product isolated as the hydrochloride salt. $^1$H NMR (DMSO-d$_6$) δ9.38 (s, 1H), 8.72 (t, J=2 Hz, 1H), 8.48 (d, J=2 Hz, 2H), 8.37 (d, J=7.5 Hz, 1H), 7.3 (br s, 1H), 6.24 (s, 2H), 5.31–5.23 (s, m, overlap, 3H), 3.41 (s, 3H), 1.41 (d, J=6.3 Hz, 6H); MS (APCI; (M+H)$^+$) m/z 479.

Example 29

Preparation of 2-(4-Morpholinyl)ethyl 9H-β-carboline-3-carboxylate

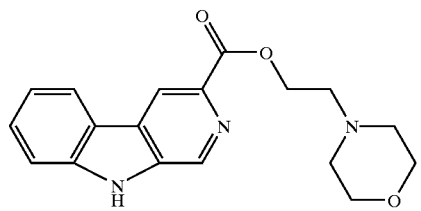

A suspension of β-carboline-3-carboxylic acid, methyl ester (5.3 g, 23.4 mmol), 4-(2-hydroxyethyl) morpholine (4.62 g, 35 mmol), 4-dimethylaminopyridine (1.2 g, 9.8 mmol), 4 Å molecular sieves (5 g) and xylene (250 mL) was heated at reflux for 48 hours. The reaction mixture was cooled to room temperature, concentrated under vacuum, and the resulting slurry was partitioned with CH$_2$Cl$_2$ (250 mL). The mixture was filtered under vacuum and the residue was washed with CH$_2$Cl$_2$ (2×25 mL). Combined organic layers were washed several times with water, dried over Na$_2$SO$_4$, and concentrated. Purification of crude product by column chromatography on silica with 8% 2M NH$_3$—CH$_3$OH in CH$_2$Cl$_2$ as eluent furnished the desired product (4.8 g, 64%) as a pale yellow solid. $^1$H NMR (CDCl$_3$) δ9.09 (s, 1H), 8.88 (s, 1H), 8.21 (d,J=7.9 Hz, 1H), 7.63 (d,J=8.1 Hz, 1H), 7.63 (d,J=8.1 Hz, 1H), 7.62 (t,J=7.38 (t, J=7.4 Hz, 2H), 4.63 (t, J=6.1 Hz, 2H), 3.73 (t, J=4.6 Hz, 4H), 6.1 Hz, 2H), 2.59 (t, J=4.6 Hz, 4H); MS (APCI; (M+H)$^+$) m/z 326.

Example 30

Preparation of 9-(3,5-dinitrobenzyl)-3-[3-(methoxymethyl)-1,2,4-oxadiazol-5-yl]-9H-β-carboline

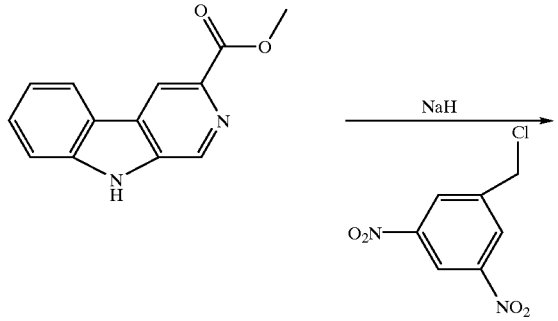

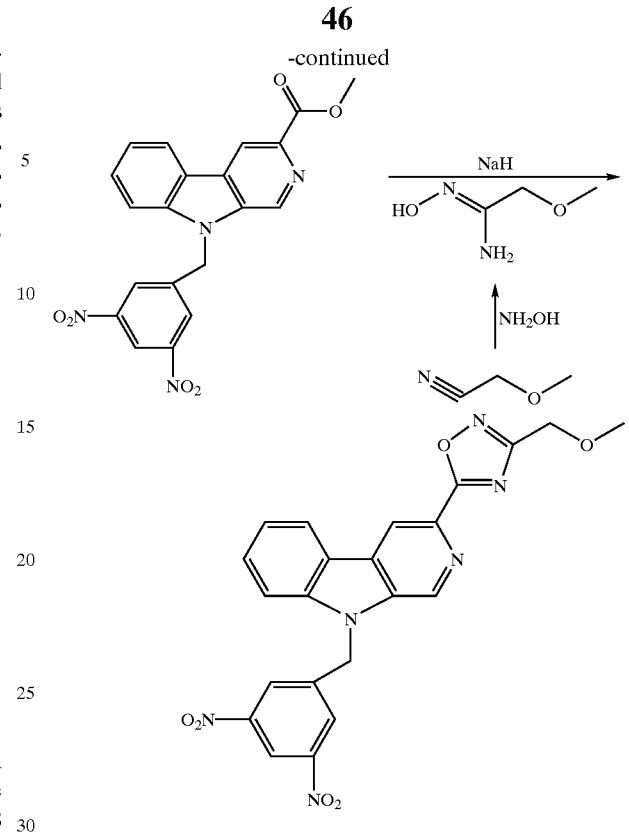

9-(3,5-Dinitrobenzyl)-3-[3-(methoxymethyl)-1,2,4-oxadiazol-5-yl]-9H-β-carboline was prepared according to a modification of a literature procedure for the synthesis of oxadiazoles from esters (Swain et al., *J. Med. Chem.* 1991, 34:140).

A suspension of hydroxylamine hydrochloride (2.02 g, 29.2 mmol), potassium carbonate (5.48 g, 39.6 mmol), and 2-methoxyacetonitrile (1.42 g, 20 mmol) in absolute ethanol (160 mL) was heated at reflux for 15 hours. The reaction mixture was cooled, filtered, and concentrated in vacuo. The residue was purified by column chromatography on silica gel with a gradient elution of 10–30% 2M NH$_3$—CH$_3$OH in CH$_2$Cl$_2$ affording 2-methoxyacetamidoxime (1.35 g, 65%) as a white solid. $^1$H NMR (DMSO-d$_6$) δ9.25 (br. s, 1H), 5.40 (br. s, 2H), 3.76 (s, 2H), 3.25 (s, 3H); MS (APCI; (M+H)$^+$) m/z 105.

A suspension of methyl 9H-β-carboline-3-carboxylate (2.26 g, 10 mmol), sodium hydride (11 mmol, 440 mg of 60% mineral oil dispersion) and 3,5-dinitrobenzyl chloride (2.17 g, 10 mmol) in DMF (25 mL) was treated as described in Method B. Recrystallization of the crude material from ethyl acetate/hexane afford methyl 9-(3,5-dinitrobenzyl)-9H-carbonline-3-carboxylate (2.85 g, 70%) as a yellow solid. $^1$H NMR (CDCl$_3$) δ8.95 (s, 2H), 8.94 (s, 1H), 8.37 (s, 2H), 8.30 (d, J=7.7 Hz, 1H), 7.67 (t,J=7.4 Hz, 1H), 7.39–7.50 (5-line multiplet, 2H), 5.94 (s, 2H), 4.06 (s, 3H); MS (APCI; (M+H)$^+$) m/z 406.

A suspension of 2-methoxyacetamidoxime (260 mg, 2.5 mmol) and 4 Å molecular sieves (1 g) in anhydrous tetrahydrofuran (15 mL) was stirred at room temperature for 0.5 hours, then treated with sodium hydride (2.75 mmol, 110 mg of 60% mineral oil suspension). The mixture was heated at reflux for 1 hour. After cooling to room temperature, a suspension of methyl 9-(3,5-dinitrobenzyl)-9H-β-carboline-3-carboxylate (205 mg, 0.5 mmol) in anhydrous tetrahydrofuran (10 mL) was added. The resulting mixture was heated at reflux for 15 hours, cooled, filtered, and the filtrate concentrated in vacuo. The residue was purified by preparative thin layer chromatography with 4% 2M $NH_3$—$CH_3OH$ in $CH_2Cl_2$ as eluent to afford the desired product (86 mg, 38% yield) as a white solid. $^1$H NMR (DMSO-$d_6$) δ 9.41 (s, 1H), 9.24 (s, 1H), 8.72 (t, J=1.9 Hz, 1H), 8.59 (d, J=7.8, 1H), 8.49 (d, J=1.9 Hz, 2H), 7.94 (d, J=8.3 Hz, 1H), 7.73 (t, J=7.8Hz, 1H), 7.45 (t, J=7.5 Hz, 1H), 6.20 (s, 2H), 4.67 (s, 2H), 3.42 (s, 3H); MS (APCI; (M+H)$^+$) m/z 461.

Example 31

Preparation of Ethyl 9-(2-cyanobenzyl)-9H-β-carboline-3-carboxylate

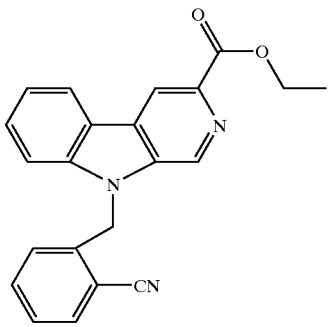

Ethyl 9-(2-cyanobenzyl)-9H-β-carboline-3-carboxylate was prepared according to Method A. The compound was purified by RP-HPLC using acetonitrile/water/trifluoroacetic acid eluent, and isolated as the trifluoroacetate salt. $^1$H NMR (300 MHz, DMSO-$d_6$) δ 9.23 (s, 1H), 9.11 (s, 1H), 8.57 (d, J=7.9, 1H), 7.95–7.98 (m, 1H), 7.67–7.71 (m, 2H), 6.40–6.53 (m, 3H), 6.72–6.78 (m, 1H), 6.13 (s, 2H), 4.42 (q, J=7.2, 2H), 1.39 (t, J=7.2, 3H); LRMS calcd for $C_{22}H_{17}N_3O_2$ (M+H) 356, found 356.1.

Example 32

Preparation of Ethyl 9-(4-methyl-3-nitrobenzyl)-9H-β-carboline-3-carboxylate

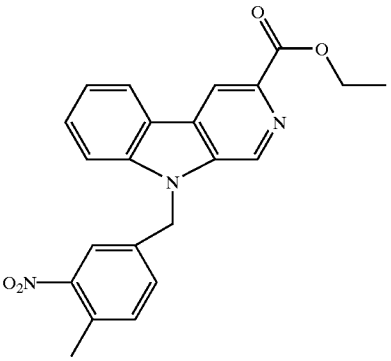

Ethyl 9-(4-methyl-3-nitrobenzyl)-9H-β-carboline-3-carboxylate was prepared by Method A. The product was purified by RP-HPLC using acetonitrile/water/trifluoroacetic acid eluent, and isolated as the trifluoroacetate salt. $^1$H NMR (300 MHz, DMSO-$d_6$) δ 9.21 (s, 1H), 8.93 (s, 1H), 8.45 (d,J=8.0, 1H), 7.88 (s, 1H), 7.78–7.83 (m, 1H), 7.58–7.68 (m, 1H), 7.30–7.45 (m, 3H), 5.89 (s, 2H), 4.31 (q, J=7.2, 2H), 2.35 (s, 3H), 1.30 (t, J=7.2, 3H); LRMS calcd for $C_{22}H_{19}N_3O_4$ (M+H) 390, found 390.1.

Example 33

Preparation of 2-(4-Morpholinyl)ethyl 9-(2-methoxy-5-nitrobenzyl)-9H-β-carboline-3-carboxylate

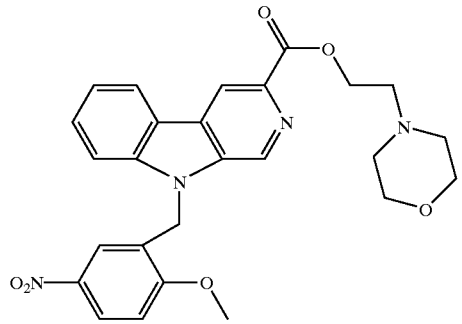

2-(4-Morpholinyl)ethyl 9-(2-methoxy-5-nitrobenzyl)-9H-β-carboline-3-carboxylate was prepared by Method A. $^1$H NMR (CDCl$_3$) δ 8.95 (s, 1H), 8.94 (s, 1H), 8.28 (d, J=7.9 Hz, 1H), 8.23 (dd, J=9.1 Hz, 2.8 Hz, 2H), 7.73 (d, J=2.6 Hz, 1H), 7.66 (t, J=7.7 Hz, 1H), 7.51 (d, J=8.2 Hz, 1H), 7.43 (t, J=7.5 Hz, 1H), 7.03 (d,J=9.1 Hz, 1H), 5.66 (s, 2H), 4.63 (t, J=6.1 Hz, 2H), 4.02 (s, 3H), 3.76 (t,J=4.6 Hz, 4H), 2.89 (t, J=6.0 Hz, 2H), 2.63 (t, J=4.4 Hz, 4H); MS (APCI; (M+H)$^+$) m/z 491.

Example 34

Preparation of 2-(4-Morpholinyl)ethyl 9-(2,4-dichlorobenzyl)-9H-β-carboline-3-carboxylate

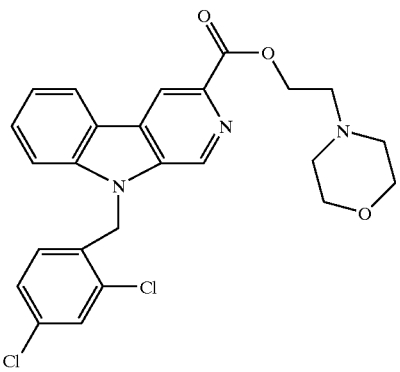

2-(4-Morpholinyl)ethyl 9-(2,4-dichlorobenzyl)-9H-β-carboline-3-carboxylate was prepared by Method A. $^1$H NMR (CDCl$_3$) δ 8.95 (s,1H), 8.86 (s, 1H), 8.23 (d,J=8.1 Hz, 1H), 7.65 (dd, J=8.0 Hz, 7.5 Hz, 2H), 7.56 (d,J=1.8 Hz, 1H), 7.44 (dd,J=8.3 Hz, 4.8 Hz, 2H), 7.02 (dd, J=8.3 Hz, 1.2 Hz, 1H), 6.48 (d, J 8.3 Hz, 1H), 5.70 (s, 2H), 4.62 (t, J=6.0 Hz, 2H), 3.76 (t, J=4.5 Hz, 4H), 2.88 (t, J=6.0 Hz, 2H), 2.63 (t,J=4.4 Hz, 4H); MS (APCI; (M+H)$^+$) m/z484.

Example 35

Preparation of 2-(4-Morpholinyl)ethyl 9-(3,4-dichlorobenzyl)-9H-β-carboline-3-carboxylate

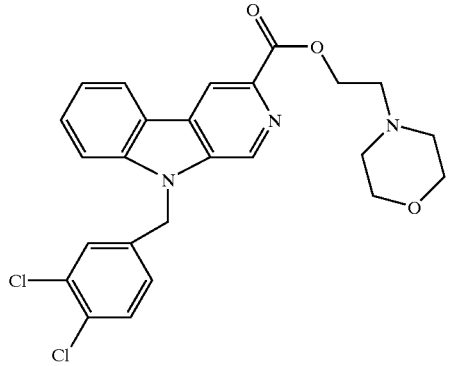

2-(4-Morpholinyl)ethyl 9-(3,4-dichlorobenzyl)-9H-β-carboline-3-carboxylate was prepared by Method A. $^1$H NMR (CDCl$_3$) δ8.93 (s, 1H), 8.90 (s, 1H), 8.27 (d,J=5.8 Hz, 1H), 7.66 (t, J=7.7 Hz, 1H), 7.35–7.48 (7-line multiplet, 3H), 7.27 (s, 1H), 6.96 (d, J=8.3 Hz, 1H), 5.60 (s, 2H), 4.62 (t,J=6.2 Hz, 2H), 3.76 (t,J=4.4 Hz, 4H, 2.88 (t, J=6.1 Hz, 2H), 2.63 (t, J=4.0 Hz, 4H); MS (APCI; (M+H)$^+$) m/z 484.

Example 36

Preparation of 2-(4-Morpholinyl)ethyl 9-[3-fluoro-5-(trifluoromethyl)benzyl]-9H-β-carboline-3-carboxylate

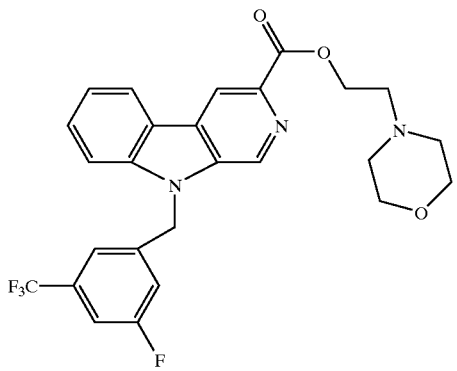

2-(4-Morpholinyl)ethyl 9-[3-fluoro-5-(trifluoromethyl)benzyl]-9H-β-carboline-3-carboxylate was prepared by Method A. $^1$H NMR (CDCl$_3$) δ8.96 (s, 1H), 8.89 (s, 1H), 8.30 (d, J=8.1 Hz, 1H), 7.68 (t, J=7.7 Hz, 1H), 7.43–7.48 (multiplet, 2H), 7.34 (s, 1H), 7.28 (s, 1H), 6.88 (d,J=8.7 Hz, 1H), 5.70 (s, 2H), 4.63 (t,J=6.1 Hz, 2H), 3.76 (t, J=4.5 Hz, 4H), 2.89 (t, J=6.1 Hz, 2H), 2.63 (t, J=4.0 Hz, 4H); MS (APCI; (M+H)$^+$)m/z 502.

Example 37

Preparation of 2-(4-Morpholinyl)ethyl 9-(4-fluoro-3-(trifluoromethyl)benzyl]-9H-β-carboline-3-carboxylate

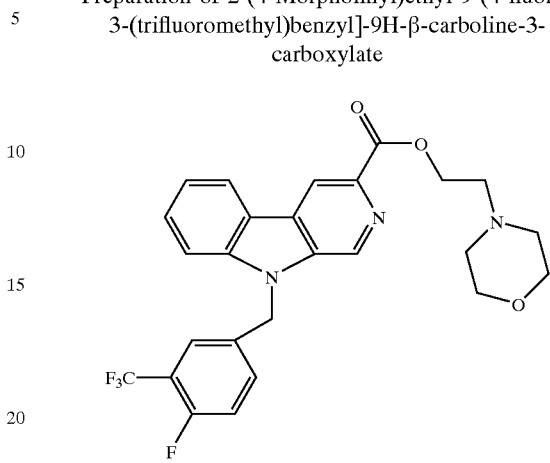

2-(4-Morpholinyl)ethyl-9-(4-fluoro-3-(trifluoromethyl)benzyl)-9H-β-carboline-3-carboxyl-ate was prepared by Method A. $^1$H NMR (CDCl$_3$) δ8.95 (s, 1H), 8.90 (s, 1H), 8.29 (d, J=7.8 Hz, 1H), 7.68 (t, J=7.7 Hz, 1H), 7.42–7.53 (7-line multiplet, 3H), 7.20–7.25 (multiplet, 1H), 7.12 (t,J=9.2 Hz, 1H), 5.67 (s, 2H), 4.62 (t,J=6.0 Hz, 2H), 3.67 (t, J=4.0 Hz, 4H), 2.89 (t, J=6.1 Hz, 2H), 2.60 (t, J=4.0 Hz, 4H); MS (APCI; (M+H)$^+$) m/z 502.

Example 38

Preparation of 2-(4-Morpholinyl)ethyl 9-(2,3,4-trifluorobenzyl)-9H-β-carboline-3-carboxylate

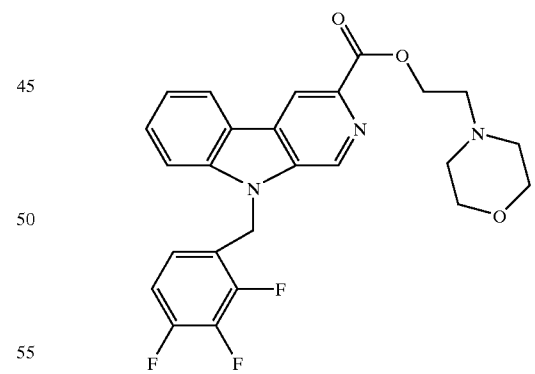

2-(4-Morpholinyl)ethyl 9-(2,3,4-trifluorobenzyl)-9H-β-carboline-3-carboxylate was prepared by Method A. $^1$H NMR (CDCl$_3$) δ8.97 (s, 1H), 8.93 (s, 1H), 8.26 (d,J=7.8 Hz, 1H), 7.68 (td,J 7.2 Hz, 1.0 Hz, 1H), 7.53 (d,J=8.3 Hz, 1H), 7.44 (t,J=7.4 Hz, 1H), 6.78–6.87 (10-line multiplet, 1H), 6.57–6.65 (multiplet, 1H), 5.68 (s, 2H), 4.62 (t, J=6.1 Hz, 2H), 3.76 (t, J=4.5 Hz, 4H), 2.89 (t,J=6.1 Hz, 2H), 2.63 (t, J=4.5 Hz, 4H); MS (APCI; (M+H)$^+$) m/z 470.

Example 39

Preparation of 2-(4-Morpholinyl)ethyl 9-(2-bromo-5-fluoromethylbenzyl)-9H-β-carboline-3-carboxylate

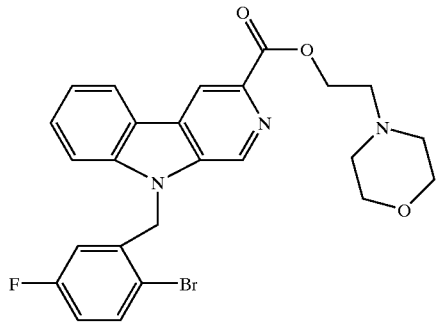

2-(4-Morpholinyl)ethyl 9-(2-bromo-5-fluoromethylbenzyl)-9H-β-carboline-3-carboxylate was prepared by Method A. $^1$H NMR (CDCl$_3$) δ8.94 (s, 1H), 8.83 (s, 1H), 8.28 (d, J=7.8 Hz, 1H), 7.61–7.68 (5-line multiplet, 2H), 7.40–7.46 (5-line multiplet, 2H), 6.90 (td, J=8.2 Hz, 2.9 Hz, 1H), 6.16 (dd,J=9.0 Hz, 2.9 Hz, 1H), 5.64 (s, 2H), 4.62 (t, J=6.1 Hz, 2H), 3.76 (t, J=4.6 Hz, 4H), 2.88 (t, J=6.1 Hz, 2H), 2.62 (t,J=4.5 Hz, 4H); MS (APCI; (M+H)$^+$) m/z 514.

Example 40

Preparation of 2-(4-Morpholinyl)ethyl 9-(2-cyanobenzyl)-9H-β-carboline-3-carboxylate

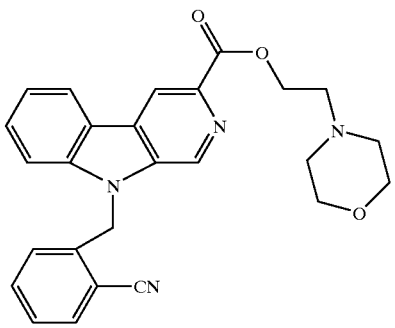

2-(4-Morpholinyl)ethyl 9-(2-cyanobenzyl)-9H-β-carboline-3-carboxylate was prepared from 2-(4-morpholinyl)ethyl 9H-β-carboline-3-carboxylate according to Method A. The free base was treated with ethereal hydrogen chloride, and the product isolated as the dihydrochloride salt in 25% yield after crystallization from acetone/ether. $^1$H NMR (DMSO-d$_6$) δ11.8 (brs, 1H), 9.61 (s, 1H), 9.40 (s, 1H), 8.71 (d, J=8 Hz, 1H), 7.93 (d, J 8 Hz, 1H), 7.72 (s, 2H), 7.54–7.47 (m, 3H), 6.78 (d,J=7.3 Hz, 1H), 6.22 (s, 2H), 4.79 (br s, 2H, overlap with water peak), 4.00 (br s, 4H), 3.66 (br s, 4H), 3.27 (br s, 2H); MS (APCI; (M+H)$^+$) m/z 441.

Example 41

Preparation of 2-(4-Morpholinyl)ethyl 9-[2,4-bis-(trifluoromethyl)benzyl]-9H-β-carboline-3-carboxylate

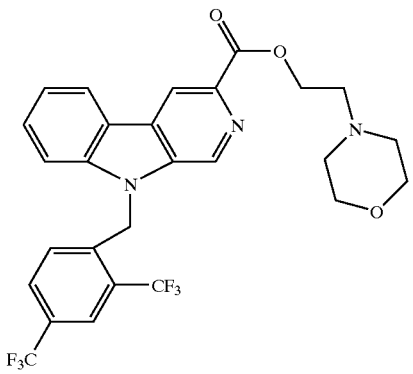

2-(4-Morpholinyl)ethyl-9-[2,4-bis-(trifluoromethyl)benzyl]-9H-β-carboline-3-carboxylate was prepared from 2-(4-morpholino)ethyl 9H-β-carboline-3-carboxylate using alkylation Method A on a 0.2-mmol scale (yield: 45%). $^1$H NMR (CDCl$_3$) δ8.97 (s, 1H), 8.83 (s, 1H), 8.31 (d,J=8 Hz, 1H), 8.07 (s, 1H), 7.66 (t,J=7.5 Hz, 1H), 7.54 (d, J=7.9 Hz, 1H), 7.47 (t,J=7.5 Hz, 1H), 7.38 (d,J=8 Hz, 1H), 6.79 (d,J=7.9 Hz), 1H), 5.9 (s, 2H), 4.63 (t, J=6 Hz, 2H), 3.75 (m, 4H), 2.88 (t, J=6 Hz, 2H), 2.62 (m, 4H); MS (APCI; (M+H)$^+$) m/z 552.

Example 42

Preparation of 6-(2,5-Dichlorobenzyl)-1-hydroxy-2-[2-(4-morpholinyl)ethyl]-1,6-dihydropyrrolo[3',4':5,6]pyrido[3,4-b]indol-3(2H)-one

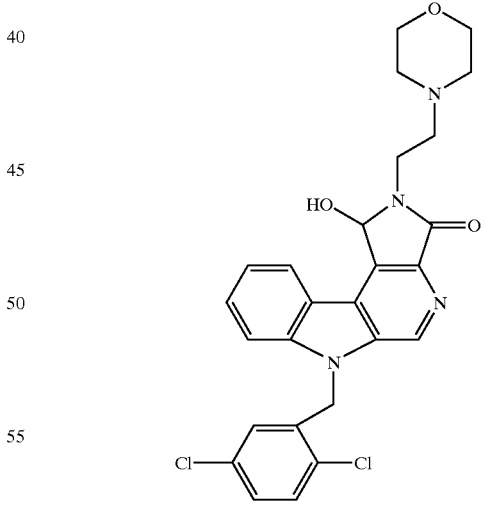

6-(2,5-Dichlorobenzyl)-1-hydroxy-2-[2-(4-morpholinyl)ethyl]-1,6-dihydropyrrolo[3',4':5,6]-pyrido[3,4-b]indol-3 (2H)-one was prepared by a slight modification of a reported procedure (Dodd et al., *J Org. Chem.* 1993, 58:7587): A solution of 9-(2,5-dichlorobenzyl)-N-[2-(4-morpholinyl) ethyl]-9H-β-carboline-3-carboxamide (400 mg, 0.83 mmol) in anhydrous THF (12 mL) was stirred and cooled to −78° C. under nitrogen. When an internal temperature of −78° C.

was attained, a 1.0 M methyllithium in diethyl ether/cumene solution (4.2 mL, 4.2 mmol) was added by syringe over a period of 0.3 hours. The reaction mixture developed a very dark blue color after complete addition of methyllithium. The solution was stirred at −78° C. for 2 hours, and the dry ice-acetone bath was then replaced with an ice-water bath. After 0.5 hour, anhydrous DMF (3070 mg, 4.2 mmol) was added dropwise, and the reaction mixture was stirred at room temperature for another 15 hours. The solution was cooled to 0° C., and distilled water was slowly added while maintaining the internal temperature of the reaction mixture at 0–5° C. The solution was concentrated to about 10 mL under reduced pressure, excess $CH_2Cl_2$ was added, and the mixture was washed with water. The organic phase was dried ($Na_2SO_4$), and the solvents were removed in vacuo. The resulting crude residue was washed several times with ether. Purification of the crude material by column chromatography on silica with 4% 2M $MH_3$—$CH_3OH$ in $CH_2Cl_2$ as eluent furnished the lactam (106 mg, 25%) as a pale yellow solid. A 241 mg portion (60%) of unreacted starting material was recovered by evaporating combined ether layers and chromatography fractions. $^1H$ NMR ($CDCl_3$) δ8.76 (s, 1H), 8.48 (d, J=7.6 Hz, 1H), 7.66 (td, J=8.2 Hz, 0.91 Hz, I H), 7.46 (t,J=7.4 Hz, 1H), 7.35–7.40 (4 -line multiplet, 2H), 7.18 (dd, J=8.5 Hz, 2.4 Hz, 1H), 6.42 (d,J=2.3 Hz, 1H), 6.17 (s, 1H), 5.56 (s, 2H), 4.46 (dt, J=9.6, 2.7 Hz, 1H), 3.83 (t, J=4.3 Hz, 4H), 3.47 (td,J=9.8, 1.5 Hz, 1H), 2.78–2.86 (m, 3H), 2.51–2.64 (m, 3H), 1.50–2.30 (v. br. s, 1H); MS (APCI; (M+H)$^+$) m/z 511.

Example 43

Preparation of 3-(3-Pyridyl)propyl 9-(2,5-dichlorobenzyl)-9H-β-carboline-3-carboxylate

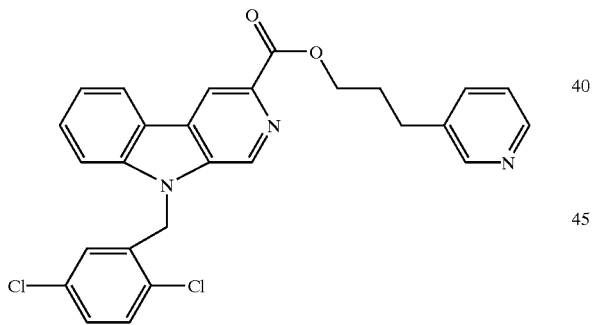

A suspension of 3-(1-imidazolylcarbonyl)-9-(2,5-dichlorobenzyl)-9H-β-carboline (505 mg, 1.20 mmol) and 3-pyridinepropanol (8.2 g, 60 mmol) was heated at 80° C. in toluene (15 mL) for 22 hours. The resulting solution was cooled to room temperature, and extracted several times with water before drying the organic phase with $Na_2SO_4$. Evaporation of the solvent followed by preparative thin layer chromatography of the resulting crude material with hexane/ethyl acetate (6:4) as eluent furnished the desired product (470 mg, 80% yield) as a pale yellow solid. $^1H$ NMR ($CDCl_3$) δ8.91 (s, 1H), 8.88 (s, 1H), 8.56 (s, 1H), 8.48 (s, 1H), 8.31 (d,J=8.0 Hz, 1H), 7.67 (AB q, J=7.4 Hz, 1H), 7.60 (d, J=7.8 Hz, 1H), 7.42–7.48 (m, 3H), 7.22–7.28 (m, 2H), 6.60 (s, 1H), 5.70 (s, 2H), 4.53 (t,J=6.5 Hz, 3H), 2.87 (t, J=7.7 Hz, 3H), 2.26 (t, J=7.3 Hz, 3H); MS (ACPl; (M+H)$^+$) m/z 490.

Example 44

Preparation of Tetrahydro-3-furanylmethyl 9-(2,5-dichlorobenzyl)-9H-β-carboline-3-carboxylate

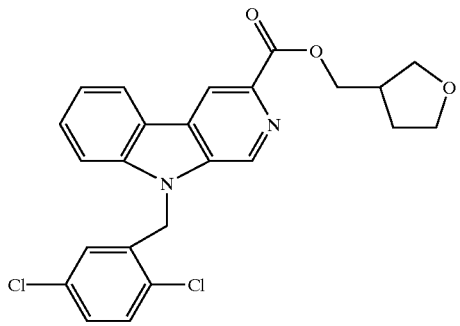

Tetrahydro-3-furanylmethyl 9-(2,5-dichlorobenzyl)-9H-β-carboline-3-carboxylate was prepared according to Method B. The compound was purified by RP-HPLC using acetonitrile/water/trifluoroacetic acid eluent, and the product isolated as the trifluoroacetate salt. $^1H$ NMR (300 MHz, DMSO-d,) δ9.12 (s, 1H), 9.02 (s, 1H), 8.54 (d, J=4.72 Hz, 1H), 7.65–7.68 (m, 2H), 7.61 (d,J=5.28 Hz, 1H), 7.39–7.45 (m, 2H), 6.65 (d, J=1.6 Hz,1H), 5.94 (s,1H), 4.35 (dd,J=4.05, 6.48 Hz, 1H), 4.27 (dd,J=4.75 Hz, 6.48, 1H), 3.77–3.85 (m, 2H), 3.65–3.71 (m, 2H), 3.57–3.62 (m, 1H), 2.69–2.74 (m, 1H), 2.03–2.09 (m, 1H), 1.68–1.75 (m, 1H); LRMS calcd for $C_{24}H_{20}Cl_2N_2O_3$ (M+H) 455, found 455.1.

Example 45

Preparation of 9-(2,5-Dichlorobenzyl)-N-[2-(4-morpholinyl)ethyl]-9H-β-carboline-3-carboxylate

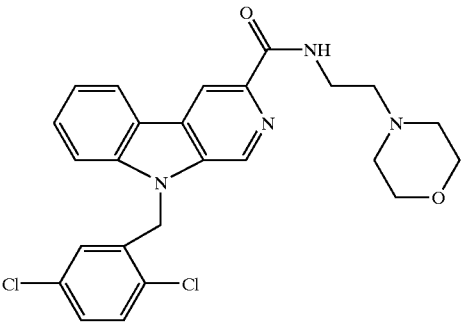

9-(2,5-Dichlorobenzyl)-N-[2-(4-morpholinyl)ethyl]-9H-β-carboline-3-carboxylate was prepared by a modification of a known procedure (Dodd et al., J Org. Chem., 1993, 58:7587). To a solution of trimethylaluminum (2 mL of a 2M solution in hexane, 4 mmol) in anhydrous $CH_2Cl_2$ (12.5 mL) cooled to −10° C. was added a solution 4-(2-aminoethyl) morpholine (261 mg, 2 mmol) in anhydrous $CH_2Cl_2$ (2.5 mL) dropwise. The reaction mixture was stirred for 0.5 hours at −10° C. and then allowed to warm to room temperature over 0.5 hours. A solution of methyl 9-(2,5-dichlorobenzyl)-9H-β-carboline-3-carboxylate (800 mg, 2 mmol) in anhydrous $CH_2Cl_2$ (5 mL) was added to the reaction mixture, and the latter was heated at reflux for 15 hours. The solution was cooled to room temperature, quenched slowly with 1.8M aqueous hydrochloric acid (5 mL) and basified to pH 9.0–9.5 with aqueous sodium bicarbonate to afford a white solid. The suspension was filtered through a pad of Celite and the residue was washed with CH$_2$Cl$_2$ (2×5 mL). Evaporation of the dried (over Na$_2$SO$_4$) filtrate afforded a yellow solid, which upon recrystallization from ethyl acetate furnished the desired carboxamide in 80% (774 mg) isolated yield. $^1$H NMR (CDCl$_3$) δ9.00 (s, 1H), 8.68 (s, 1H), 8.43 (t, J=3.9 Hz, 1H), 8.30 (dd,J=7.5, 1.1 Hz, 1H), 7.64 (dt,J=7.7, 1.1Hz 1H), 7.42 (t, J=7.9Hz, 2H), 7.23 (dd, J=8.5, 2.4Hz, 1H), 6.54 (s, 1H), 5.67 (s,2H), 3.77 (t, J=4.6 Hz, 4H), 3.68 (q,J=5.8, 3.9 Hz, 2H), 2.67 (t,J=6.2 Hz, 2H), 2.56 (t,J=5.1 Hz, 4H); MS (APCI; (M+H)$^+$) m/z483.

Example 46

Preparation of 9-(2,5-Dichlorobenzyl)-9H-β-carboline-3-carbohydrazide

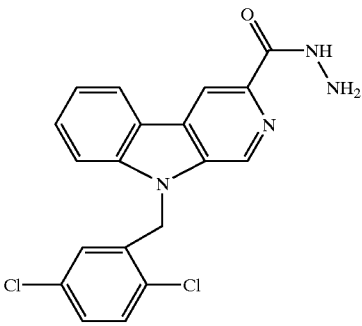

A mixture of methyl 9-(2,5-dichlorobenzyl)-9H-β-carboline-3-carboxylate (4.8 g, 12.5 mmole), hydrazine (6 mL) and methanol (50 mL) was refluxed for 5 hours. The reaction mixture was cooled to room temperature, and the precipitate was collected by filtration. The solid was treated with methanol (50 mL) and the slurry stirred for 10 minutes, filtered, and dried, affording 4.6 grams (98%) of the title compound. $^1$H NMR (DMSO-d$_6$) δ9.5 (s, 1H), 8.8 (s, 1H), 8.7 (s, 1H), 8.25 (d, 1H), 7.6–7.4 (m, 3H), 7.2–7.1 (m, 2H), 6.5 (s, 1H), 5.7 (s, 2H), 4.3 (s, 2H) MS (APCI; (M+H)$^+$) m/z 385.

Example 47

Preparation of 9-(2,5-Dichlorobenzyl)-9H-β-carboline-3-carbaldehyde O-methyloxime

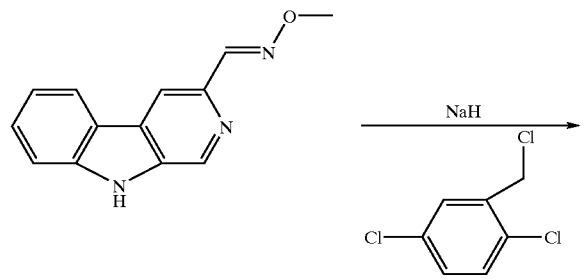

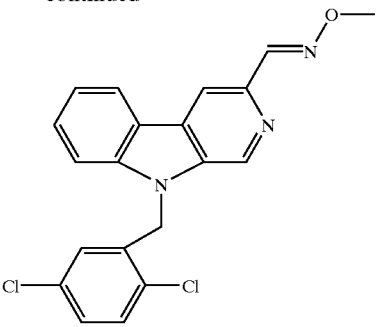

A mixture of 9H-β-carboline-3-carbaldehyde O-methyloxime (46 mg, 0.20 mmol), NaH (0.22 mmol, 9 mg of 60 wt. % suspension in mineral oil), and 2,5-dichlorobenzyl chloride (43 mg, 0.22 mmol) in DMF (1.5 mL) was treated according to Method A. Purification of the crude product by preparative thin layer chromatography with hexane/ethyl acetate (7:3) as eluent furnished the desired product (37 mg, 48% yield) as a white solid. $^1$H NMR (DMSO-d$_6$) δ9.00 (s, 1H), 8.64 (s, 1H), 8.45 (d,J=7.8 Hz, 1H), 8.32 (s, 1H), 7.64–7.59 (m, 2H), 7.61 (d, J=8.6 Hz, 1H), 7.41 (dd, J=8.6, 1.5 Hz, 1H), 7.36 (m, 1H), 6.60 (d,J=2.5 Hz, 1H), 5.86 (s, 2H), 3.97 (s, 3H), MS (APCI; (M+H)$^+$) m/z 384.

Example 48

Preparation of 4-[-2-{[9-(2,5-Dichlorobenzyl)-9H-β-carboline-3-yl]carbonyl}hydrazono)-methyl]benzoic acid

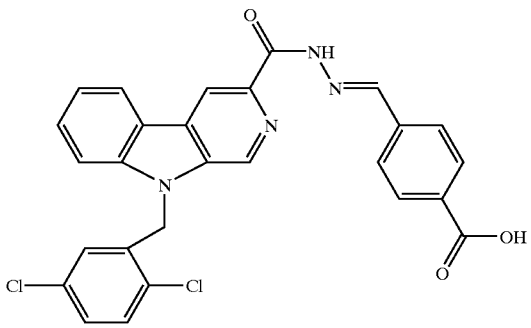

A mixture of 9-(2,5-dichlorobenzyl)-9H-β-carboline-3-carbohydrazide (77 mg, 0.2 mmol), 4-formyl benzoic acid (30 mg, 0.2 mmol), DMSO (5 mL), and one drop of glacial acetic acid was stirred at room temperature for 12 hours. Ethyl acetate (50 ml) was added to the flask. The mixture was extracted with water and brine. The product which crystallized from the organic phase was filtered, affording 80 mg (78%) of the title compound. $^1$H NMR (DMSO-d$_6$) δ9.0 (s, 2H), 8.5 (s, 1H), 8.3 (s, 1H), 8.0 (d, 2H), 7.8 (d, 2H), 7.5–7.7 (m, 4H), 7.3–7.4 (m, 2H), 6.8 (s, 1H), 5.9 (s, 2H), 8.0 (d, 2H), (M+H)$^+$) m/z 517.

Example 49

Preparation of 4-[1-(2-{[9-(2,5-dichlorobenzyl)-9H-β-carboline-3-yl]carbonyl}hydrazono)-ethyl]benzoic acid

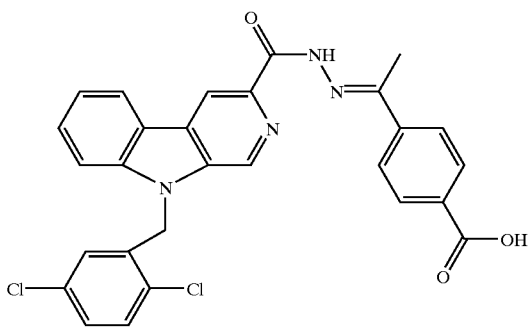

A mixture of 9-(2,5-dichlorobenzyl)-9H-β-carboline-3-carbohydrazide (100 mg, 0.25 mmole), 4-acetyl benzoic acid (50 mg, 0.3 mmole), DMSO (5 mL), and one drop of glacial acetic acid was stirred at room temperature for 12 hours. Ethyl acetate (50 ml) was added to the flask. The mixture was extracted with water and brine. The product crystallized from the organic phase was filtered, affording 97 mg (73%) of the title compound. $^1$H NMR (DMSO-$d_6$) δ9.0 (s, 2H), 8.5 (d, 1H), 8.25 (s, 1H), 8.0–7.9 (m, 4H), 7.6–7.5 (m, 3H), 7.4–7.3 (m, 2H), 6.6 (s, 1H), 5.9 (s, 2H), 2.4 (s, 3H), MS (APCI; (M+H)$^+$) m/z 531.

Example 50

Preparation of 2-(4-Morpholinyl)ethyl 9-(3,5-dinitrobenzyl)-4-(methoxymethyl)-9H-β-carboline-3-carboxylate

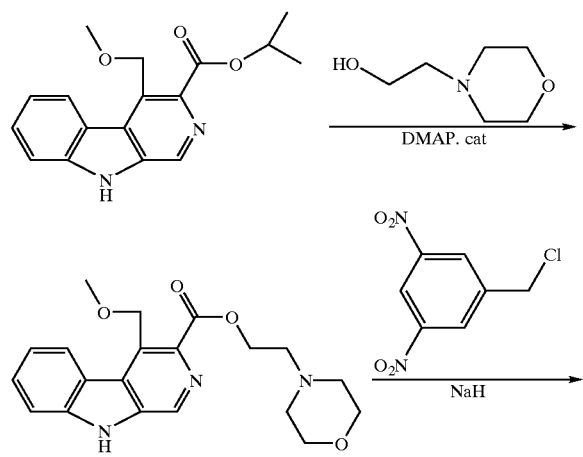

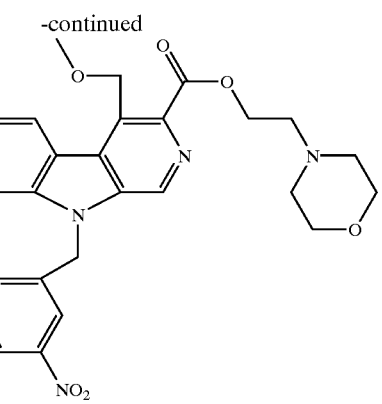

A suspension of isopropyl 4-(methoxymethyl)-9H-β-carboline-3-carboxylate (522 mg, 1.75 mmol), 4-(2-hydroxyethyl)morpholine (6.7 g, 51 mmol), 4-dimethylaminopyridine (130 mg, 1.05 mmol), 4 Å molecular sieves (500 mg) and xylene (25 mL) was refluxed for 48 hours. The reaction mixture was cooled to room temperature, concentrated under vacuum, and the resulting slurry was partitioned with CH$_2$Cl$_2$ (50 mL). The mixture was filtered and the residue was washed with CH$_2$Cl$_2$ (2×5 mL). Combined organic layers were washed several times with water, dried over Na$_2$SO$_4$, and concentrated. The crude product, 2-(4-morpholinyl)ethyl 4-(methoxymethyl)-9H-β-carboline-3-carboxylate, was about 95% pure by $^1$H NMR and was used in the next step without further purification.

The title compound was prepared according to Method A, using 2-(4-morpholinyl)ethyl 4-(methoxymethyl)-9H-β-carboline-3-carboxylate (100 mg, 0.27 mmol), sodium hydride (0.30 mmol, 12 mg of 60% mineral oil suspension), and 3,5-dinitrobenzyl chloride (65 mg, 0.30 mmol) in DMF (2 mL). Purification of the crude material by preparative thin layer chromatography with ethyl acetate/hexane (7:3) afforded 2-(4-morpholinyl)ethyl 9-(3,5-dinitrobenzyl)-4-(methoxymethyl)-9H-β-carboline-3-carboxylate (107 mg, 72%). $^1$H NMR (CDCl$_3$) δ8.98 (s, 1H), 8.81 (s, 1H), 8.44 (d, J=8.0 Hz, 1H), 8.31 (d, J=1.9 Hz, 2H), 7.68 (t, J=7.3 Hz, 1H), 7.49 (t, J=7.6 Hz, 1H), 7.42 (d, J=8.3 Hz, 2H), 5.83 (s, 2H), 5.44 (s, 2H), 4.59 (t, J=5.8 Hz, 2H), 3.76 (t, J=4.5Hz, 4H), 3.56 (s, 3H), 2.85 (t, J=5.8Hz, 2H), 2.63 (t, J=4.5 Hz, 4H); MS (APCI; (M+H)$^+$) m/z 550.

Example 51

Preparation of 3-(4-Pyridinyl)propyl 9-(2,5-dichlorobenzyl)-9H-β-carboline-3-carboxylate

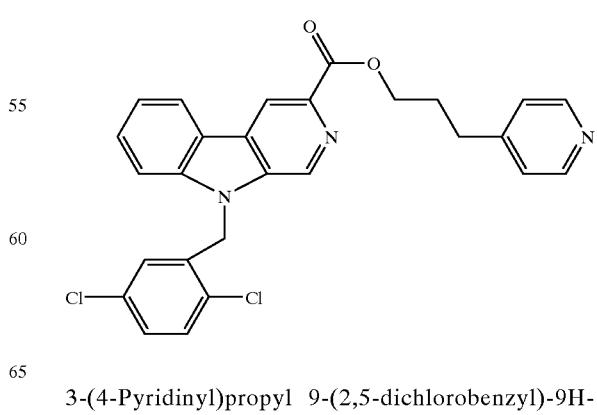

3-(4-Pyridinyl)propyl 9-(2,5-dichlorobenzyl)-9H-β-carboline-3-carboxylate was prepared according to Method B. $^1$H NMR (300 MHz, DMSO-d$_6$) δ9.10 (s, 1H), 8.94 (m, (s, 1H), 8.53 (d, J=7.9, 1H), 8.47 (d,J=5.3, 2H), 7.59–7.68 (m, 3H), 7.40–7.45 2H), 7.32 (d, J=5.6, 2H), 6.64 (d,J=2.3, 1H), 5.93 (s, 2H), 2.77–2.85 (m, 4H), 2.08–2.16 (m, 2H); LRMS calcd for C$_{27}$H$_{21}$Cl$_2$N$_3$O$_2$ (M+H) 490, found 490.1.

Example 52

Preparation of 3-(2-Oxo-1-pyrrolidinyl)propyl 9-(2, 5-dichlorobenzyl)-9H-β-carboline-3-carboxylate

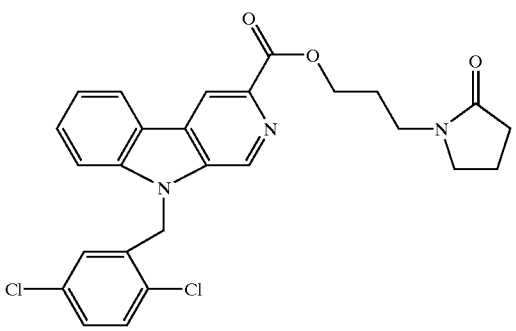

3-(2-Oxo-1-pyrrolidinyl)propyl 9-(2,5-dichlorobenzyl)-9H-β-carboline-3-carboxylate was prepared according to Method B. $^1$H NMR (300 MHz, DMSO-d$_6$) δ9.17 (s, 1H), 9.07 (s, 1H), 8.52 (d,J=7.93Hz, 1H), 7.56–7.69 (m, 3H), 7.37–7.44 (m, 2H), 6.64 (d, J=2.3Hz, 1H), 5.92 (s, 2H), 4.32 (t,J=6.2Hz, 2H), 3.33–3.40 (m, 4H), 2.16 (t, J=7.9 Hz, 2H), 1.82–2.00 (m, 4H); LRMS calcd for C$_{26}$H$_{23}$Cl$_2$N$_3$O$_3$ (M+H) 496, found 496.1.

Example 53

Preparation of 3-(2-Pyridinyl)propyl 9-(2,5-dichlorobenzyl)-9H-β-carboline-3-carboxylate

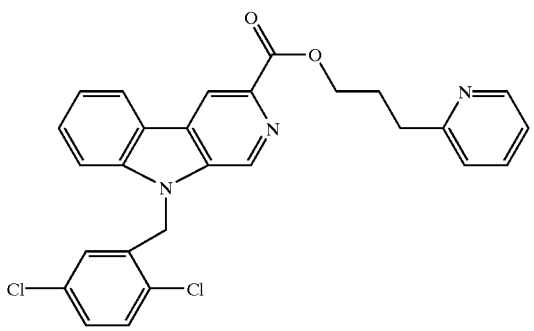

3-(2-Pyridinyl)propyl 9-(2,5-dichlorobenzyl)-9H-β-carboline-3-carboxylate was prepared according to Method B. $^1$H NMR (300 MHz, DMSO-d$_6$) δ9.14 (s, 1H), 8.97 (s, 1H), 8.56 (d, J=4.5 Hz, 1H), 8.50 (d, J 7.9 Hz, 1H), 7.60–7.75 (m, 5H), 7.39–7.46 (m, 2H), 7.34 (d, J=7.6 Hz, 1H), 7.20–7.25 (m, 1H), 6.69 (d,J=2.3 Hz, 1H), 5.90 (s, 1H), 4.46 (t, J=6.4 Hz, 2H), 3.00 (t, J=7.4 Hz), 2.22–2.32 (m, 2H). LRMS calcd for C$_{27}$H$_{21}$Cl$_2$N$_3$O$_2$ (M+H) 490, found 490.

Example 54

Preparation of 2-[4-(Ethoxycarbonyl)-1-piperazinyl]ethyl 9-(2,5-dichlorobenzyl)-9H-β-carboline-3-carboxylate

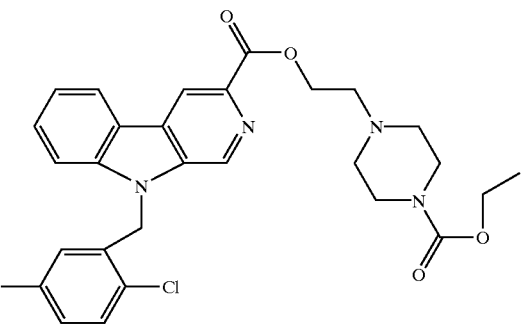

2-[4-(Ethoxycarbonyl)-1-piperazinyl]ethyl 9-(2,5-dichlorobenzyl)-9H-β-carboline-3-carboxylate was prepared according to Method B. $^1$H NMR (300 MHz, DMSO-d$_6$) δ9.11 (s, 1H), 8.99 (s, 1H), 8.50 (d,J=7.9Hz, 1H), 7.59–7.67 (m, 3H), 7.38–7.44 (m, 2H), 6.65 (d, J=2.3 Hz, 1H), 5.90 (s, 2H), 4.46–4.52 (m, 2H), 4.05 (q,J=7.2 Hz, 2H), 3.35–3.45 (m, 4H), 2.75–2.87 (m, 2H), 2.45–2.60 (m, 4H), 1.18 (t,J=7.2 Hz, 3H); LRMS calcd for C$_{28}$H$_{28}$Cl$_2$N$_4$O$_4$ (M+H) 555, found 555.1.

Example 55

Preparation of 9-(2,5-Dichlorobenzyl)-9H-β-carboline-3-carbaldehyde

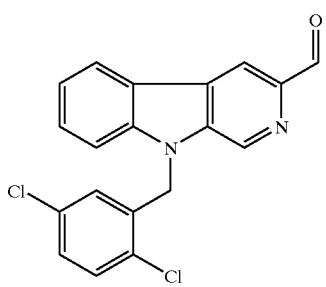

A 250-mL round-bottomed flask was charged with [9-(2, 5-dichlorobenzyl)-9H-β-carbolin-3-yl]methanol (1.84 g, 5.1 mmol), manganese (IV) oxide (1.14 g, 13.1 mmol) and dichloromethane (60 mL). The reaction mixture was stirred at room temperature for 12 hours. The mixture was filtered, concentrated in vacuo, and the residue chromatographed (hexane:ethyl acetate=10:1), affording the title compound (1.6 g, 87% yield). $^1$H NMR (CDCl$_3$) δ10.3 (s, 1H), 8.9 (s, 1H), 8.8 (s, 1H), 8.3 (d,1H), 7.7 (t, 1H), 7.5–7.4 (m, 3H), 7.2 (s, 1H), 6.6 (s, 1H), 5.7 (s, 2H), MS (Cl); 355, 357, 359.

Example 56

Preparation of [9-(2,5-Dichlorobenzyl)-9H-β-carbolin-3-yl]methylamine

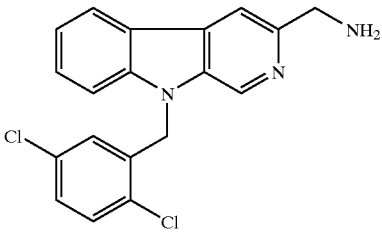

A solution of [9-(2,5-dichlorobenzyl)-9H-β-carbolin-3-yl]methanol (7.14 g, 20 mmol) in anhydrous $CH_2Cl_2$ (100 mL) was cooled to 0° C. under nitrogen atmosphere, and thionyl chloride (2.5 g, 20.8 mmol) was added dropwise with stirring. The solution was allowed to warm to room temperature and stirred for another 15 hours. The reaction mixture was diluted with anhydrous ethanol (50 mL) and concentrated on a rotary evaporator to give a pale-yellow solid. The crude material was crystallized by addition of anhydrous ether, affording 6.92 grams (84%) of 3-chloromethyl-9-(2,5-dichlorobenzyl)-9H-β-carboline hydrochloride. This salt was converted to the free base by addition of aqueous $Na_2CO_3$ and then extracting the resulting mixture with $CH_2Cl_2$. The organic layer was dried ($Na_2SO_4$) and concentrated in vacuo to give 0.30 g (100%) of the free base as a pale yellow solid. $^1$H NMR ($CDCl_3$) δ8.72 (s, 1H), 8.20 (d, J=7.9, 2.3 Hz, 1H), 8.18 (s, 1H), 7.60 (t,J=7 Hz, 1H), 7.38 (m, 3H), 7.20 (dd, J=8.3, 2.3 Hz, 1H), 6.55 (s, 1H), 5.65 (s, 2H), 4.92 (s, 2H); MS monoisotopic mass (calculated) 374.0, MH+(observed) 375.2, (MH+–HCl) 339.1.

A suspension of 3-chloromethyl-9-(2,5-dichlorobenzyl)-9H-β-carboline hydrochloride (5.64 g, 15 mmol) and sodium azide (2.0 9, 30 mmol) in anhydrous ethanol (60 mL) was refluxed under nitrogen for 15 hours. The resulting suspension was cooled to room temperature, diluted with an equal volume of $CH_2Cl_2$, and washed with water (2×50 mL) and brine (2.5 mL), respectively. The organic extract was dried over anhydrous $Na_2SO_4$ and concentrated to give 5.70 grams (100%) of 3-azidomethyl-9-(2,5-dichlorobenzyl)-9H-β-carboline as a pale yellow solid. $^1$H NMR ($CDCl_3$) δ8.75 (s, 1H), 8.20 (d, J=7.4 Hz, 1H), 8.04 (s, 1H), 7.58 (t,J=7.5 Hz, 1H), 7.32–7.40 (m, 3H), 7.20 (dd, J=9.6, 2.5 Hz, 1H), 6.53 (d, J=2.3 Hz,1H), 5.52 (s, 2H), 4.20 (s, 2H); MS monoisotopic mass (calculated) 381.1, MH+ (observed) 382.0, (MH+–N2) 354.2.

Reduction of this azide to the corresponding amine was carried out according to a published procedure of Gartiser et al., *Tetrahedron Lett.*, 1983, 24:1609. A suspension of 3-azidomethyl-9-(2,5-dichlorobenzyl)-9H-β-carboline (4.60 g, 12 mmol), ammonium formate (3.90 g, 61.7 mmol), and 10% Pd-on-carbon (2.0 g, 20mol %) in ethanol (200 mL) was stirred at room temperature under nitrogen for 15 hours. The reaction mixture was filtered to remove the solids, and the filtrate concentrated and diluted with $CH_2Cl_2$ (100 mL). The resulting solution was washed with water (2×25 mL) and brine (25 mL), dried over anhydrous $Na_2SO_4$, and concentrated. The crude product was recrystallized from ethyl acetate, affording 3.0 grams (65%) of N-formyl-[9-(2,5-dichlorobenzyl)-9H-β-carbolin-3-yl]methylamine as a pale-yellow solid. $^1$H NMR ($CDCl_3$) δ 8.65 (s, 1H), 8.30 (s, 1H), 8.24 (d, 1H), 7.95 (s, 1H), 7.58 (t, 7.40 (m, 3H), 7.20 (dd, 1H), 6.51 (s, 1H), 5.60 (s, 2H), 4.78 (d, 1H); MS monoisotopic mass (calculated) 383.1, MH+ (observed) 384.9.

This formamide (2.90 g, 7.5 mmol) was treated with potassium hydroxide (5.40 g, 9.4 mmol) in ethanol/water (5:1, 48 mL) at reflux for 6 hours. The resulting suspension was cooled to room temperature, concentrated, and diluted with $CH_2Cl_2$ (50 mL). The organic phase was washed with water (2×25 mL), dried ($Na_2SO_4$), filtered and concentrated to give [9-(2,5-dichlorobenzyl)-9H-β-carbolin-3-yl]methylamine as a yellow solid. The crude material was recrystallized from ethyl acetate/hexane to give 1.48 grams (55%) of a pale-yellow solid. $^1$H NMR ($CDCl_3$) δ 8.70 (s, 1H), 8.18 (d,J=7.9 Hz, 1H), 8.03 (s, 1H), 7.58 (td,J=7.2, 1.1 Hz, 1H) 7.32–7.42 (6-line m, 3H), 7.20 (dd, J=9.6, 2.6 Hz, 1H), 6.55 (d, J=2.6 Hz, 1H), 5.60 (s, 2H), 4.28 (d, 1H), 1.96 (br s, 2H); MS monoisotopic mass (calculated) 355.1, MH+ (observed) 356.7.

Example 57

Preparation of N-{[9-(2,5-Dichlorobenzyl)-9H-β-carbolin-3-yl]methyl}-5-methyl-3-isoxazolecarboxamide

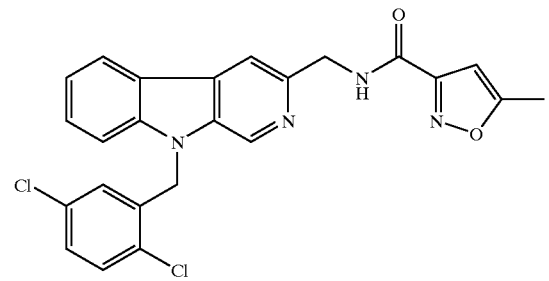

A solution of 5-methylisoxazole-3-carbonyl chloride in DCE (0.25M) was treated with a solution of [9-(2,5-dichlorobenzyl)-9H-β-carbolin-3-yl]methylamine in DME (0.25M, 1 equiv), followed by a solution of triethylamine in DME (1.0M, 1 equiv). The mixture was agitated, and allowed to stand overnight. The solvent was evaporated and the residue purified by preparative HPLC. $^1$H NMR (300 MHz, DMSO-$d_6$) δ9.5 (br t, 1H), 9.40 (s, 1H), 8.74 (s, 1H), 8.60 (d,J=7.8 Hz, 1H) 7.78 (m, 1H), 7.66–7.60 (m, overlap, 2H), 7.50–7.41 (m, overlap, 2H), 6.69 (s, 1H), 6.65 (s, 1H), 5.97 (s, 1H), 4.96 (d, J=5.4Hz, 2H), 2.49 (s, overlap with DMSO peak). A peak at 13.7 ppm in the 13C NMR spectrum is consistent with the methyl group, which presumably overlaps with the solvent in the $^1$H NMR spectrum. Monoisotopic mass calcd for $C_{24}H_{18}Cl_2N_4O_2$: 464.1, (M+H) found 465.4.

Example 58

Preparation of N-{[9-(2,5-Dichlorobenzyl)-9H-β-carbolin-3-yl]methyl-2-(trifluoro-methyl)}benzamide

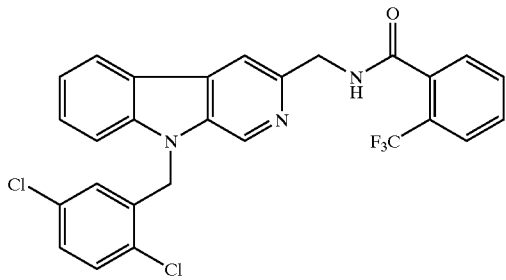

The title compound was prepared using the procedure described for N-{[9-(2,5-dichlorobenzyl)-9H-β-carbolin-3-yl]methyl}-5-methyl-3-isoxazolecarboxamide. $^1$H NMR (300 MHz, DMSO-$d_6$) δ9.41 (t, J=5.6 Hz, 1H), 9.35 (s, 1H), 8.59 (s, 1H), 8.43 (d, J=7.9 Hz, 1H), 7.84–7.60 (m, overlap, 7H), 7.50–7.33 (m, overlap, 2H), 6.66 (d,J=2.4 Hz, 1H), 5.94 (s, 2H), 4.87 (d,J=5.6 Hz, 2H). Monoisotopic mass calcd for $C_{27}H_{18}Cl_2F_3N_3O$: 527.1, (M+H) found 528.5.

Example 59

Preparation of 2-(2,5-Dioxo-1-pyrrolidinyl)ethyl 9-(2,5-dichlorobenzyl)-9H-β-carboline-3-carboxylate

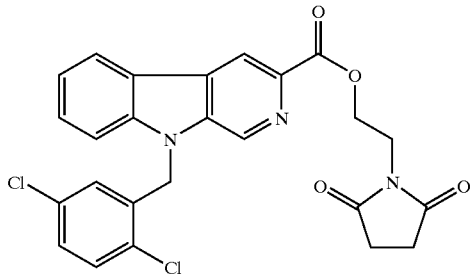

2-(2,5-Dioxo-1-pyrrolidinyl)ethyl 9-(2,5-dichlorobenzyl)-9H-β-carboline-3-carboxy-late was prepared by general method C. $^1$H NMR (300 MHz, CDCl$_3$) δ8.95 (s, 1H), 8.85 (s, 1H), 8.30 (d,J=7.8 Hz, 1H), 7.65 (m, 1H), 7.47–7.42 (m, overlap 3H), 7.23 (dd,J=8.5, 2.4Hz, 1H), 6.59 (d,J=2.4Hz, 1H), 5.68 (s, 2H), 4.65 (t,J=5 Hz, 2H), 4.05 (t, J=5 Hz, 2H), 2.75 (s, 4H). Monoisotopic mass calcd for $C_{25}H_{19}Cl_2N_3O_4$: 495.1, (M+H) found 495.8.

Example 60

Preparation of 6-(2,5-Dichlorobenzyl)1-hydroxy-1,6-dihydrol-3H-furo[3',4':5,6]-pyrido[3,4-b]indol-3-one

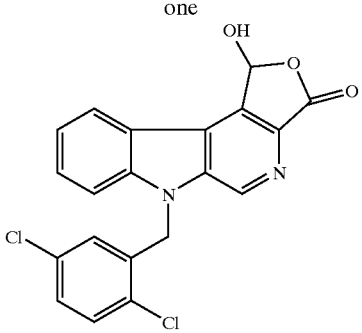

6-(2,5-Dichlorobenzyl)1-hydroxy-1,6-dihydrol-3H-furo[3',4':5,6]pyrido[3,4-b]indol-3-one was prepared by a literature procedure (Narasimhan et al., *Synthesis*, 1975, 797) with some modifications as follows. A solution of 6-(2,5-dichlorobenzyl)-1-hydroxy-2-[2-[2-(4-morpholinyl)ethyl]-1,6-dihdropyrrolo[3',4':5,6]-pyrido[3,4-b]indol -3(2H)-one (2.51 g, 4.91 mmol) in concentrated hydrochloric acid (35 mL, 406 mmol) was refluxed (using a bath temperature of 140° C.) for 48 hours. The solution turned from a brown to a greenish-yellow color in the course of about 24 hours. The solution was cooled, basified to pH ~9 with saturated NaHCO$_3$ and extracted twice with CH$_2$Cl$_2$ (2×25 mL). The aqueous layer was acidified to pH ~6 with 10% aqueous hydrochloric acid. The resulting pale brown precipitate was filtered, washed with CH$_2$Cl$_2$ and ether, respectively, and dried in vacuo at 80° C. for 15 hours. The weakly acidic filtrate precipitated an additional quantity of solid on standing overnight. This was filtered and treated as above, affording a combined yield of 1.6 grams (82%). $^1$H NMR (DMSO-$d_6$) δ9.25 (s, 1H), 8.52 (d,J=1.7 Hz, 1H, exchanges with D$_2$O), 8.30 (d,J=7.8 Hz, 1H), 7.67 (m, 2H), 7.55 (d,J=8.5 Hz, 1H), 7.42 (t,J=5.8 Hz, 1H), 7.36 (dd,J=8.4, 1.6 Hz, 1H), 7.13 (s, 1H), 6.52 (d,J=1.7 Hz, 1H), 5.94 (s, 2H); $^{13}$C NMR (DMSO-$d_6$) δ166.1, 140.1, 136.4, 135.3, 135.0, 134.8, 133.5, 130.8, 130.4, 129.6, 128.5, 128.1, 125.8, 123.1, 121.1, 120.5, 117.6, 109.9, 94.4, 43.5; MS monoisotopic mass (calculated) 398.0, MH+ (observed) 399.0.

Example 61

Preparation of 2-([(4-Cyanocyclohexyl)methyl]{[9-(2,5-dichlorobenzyl)-9H-β-carbolin-3-yl]methyl}amino)-2-oxoethyl acetate

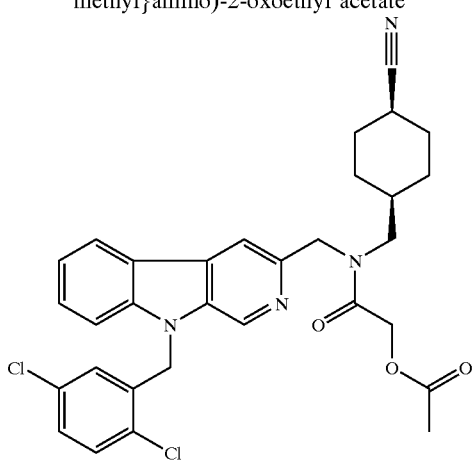

65

-continued

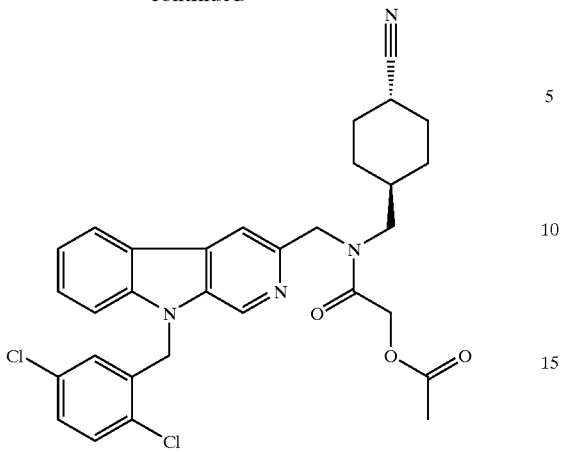

The first step of the sequence used to make this compound was a modification of a procedure reported for reductive amination (Abdel-Magid et al., *J. Org. Chem.*, 1996, 61:3849). A solution of 9-(2,5-dichlorobenzyl)-9H-β-carboline-3-carbaldehyde in methanol (0.10M) was treated with 1 equivalent of 4-cyanocyclohexanemethylamine (as mixture of diastereomers) in methanol (0.10M). The mixture was briefly agitated and allowed to stand at room temperature overnight. The solution was treated with 2 equivalents of a freshly prepared solution of sodium borohydride in undenatured anhydrous ethanol (0.50M), agitated, and allowed to stand at room temperature for 2 hours. The solution was diluted by half its volume with water, agitated (gas was evolved), and the volatiles removed in vacuo. To the solid residue was added 1 equivalent of a 0.1M solution of acetoxyacetyl chloride in DCE, 1 equivalent of a 0.2M solution of triethylamine in methylene chloride, and the mixture agitated for 2 hours. The solvent was evaporated, and the residue chromatographed by preparative HPLC. Approximately 50 mg of this residue was dissolved in 15 mL of 15% DMSO, 30% isopropanol, and 55% hexanes. This was eluted on a Kromasil 100-5 Sil (250×22 mm) column, using a gradient of hexanes (A) and isopropanol (B) at 12 mL/min, while monitoring at 238 mm. The column was eluted with a mixture of 95% A and 5% B for 15 minutes, followed by an increase in amount of B by 2% every ten minutes until the cis and trans isomer peaks elute (about 60–80 minutes). The column was washed with a mixture of 80% B and 20% A for 20 minutes, for a total run time of 120 minutes.

cis isomer: The compound appears as a set of rotamers about the tertiary amide bond: $^1$H NMR (DMSO-$d_6$) δ8.92, 8.86 (s, 1H), 8.30 (m, 1H), 8.17, 7.98 (s, 1H), 7.59 (m, overlap, 3H), 7.40–7.31 (m, 2H), 6.45 (brs, 1H), 5.82 (s, 2H), 5.01, 4.87 (s, 2H), 4.69 (br s, 2H), 3.17 (m, 2H), 2.55 (m, Wh/2=29 Hz, 1H), 2.08, 2.04 (s, 3H), 2.00–1.89 (m, 2H), 1.75–1.52 (m, 3H), 1.45–1.20 (m, 2H), 1.30–0.82 (m, 2H); LRMS calcd for $C_{31}H_{30}Cl_2N_4O_3$: 567.2; MH+ (observed) 577.2.

trans isomer: The compound appears as a set of rotamers about the tertiary amide bond. $^1$H NMR (DMSO-$d_6$) δ8.92, 8.85 (s, 1H), 8.30 (m, 1H), 8.19, 7.98 (s, 1H), 7.60 (m, overlap, 3H), 7.38 (dd,J=8.6, 2.4 Hz, 1H), 7.30 (m, 1H), 6.51 (d,J=2.6 Hz, 1H), 5.81 (br s, 2H), 5.03, 4.90 (s, 2H), 4.71 (br s, 2H), 3.25, 3.20 (d,J=6.4 Hz, 7.2 Hz, respectively, 2H), 3.09, 3.03 (m, $W_{h/2}$=8.7 Hz, 10.5 Hz, respectively, 1H), 2.08, 2.04 (s, 3H), 1.85–1.2 (m, overlap, 9H); LRMS calcd for $C_3 H_{30}Cl_2N_4O_3$: 577.2, MH+ (observed) 577.2.

66

Example 62

Preparation of N-{[(4-Cyanocyclohexyl)methyl]-N-9-(2,5-dichlorobenzyl)-9H-β-carbolin-3-yl]methyl}cyclopropanecarboxamide

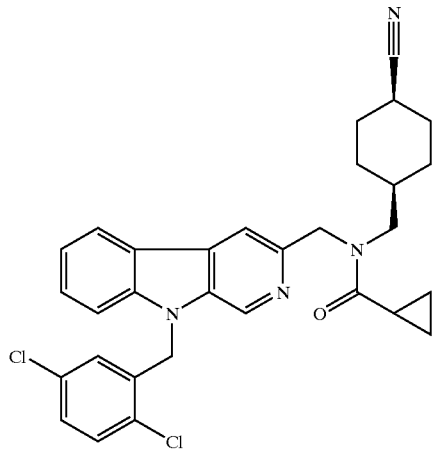

N-{[(4-Cyanocyclohexyl)methyl]-N-9-(2,5-dichlorobenzyl)-9H-β-carbolin-3-yl]methyl}cyclopropanecarboxamide was prepared similar to the procedure described above for 2-([(4-cyanocyclohexyl)methyl]{[9-(2,5-dichlorobenzyl)-9H-β-carbolin-3-yl]methyl}amino)-2-oxoethyl acetate. This compound appears as a mixture of rotamers about the tertiary amide bond. $^1$H NMR (DMSO-$d_6$) δ8.92, 8.87 (s, 1H), 8.31 (m, overlap, 1H), 8.09, 7.96 (s, 1H), 7.60 (m, overlap, 3H), 7.38 (dd,J= 8.7, 2.6 Hz, 1H), 7.30 (m,1H), 6.52, 6.50 (d,J=2.3 Hz, 1H), 5.82, 5.80 (s, 2H), 4.93, 4.73 (s, 2H), 3.44, 3.27 (d, J=7.2, 6.8 Hz, 2H), 2.58 (m, 1H), 1.95 (m, 2H), 1.72–1.56 (m, 2H), 1.48–0.55 (m, overlap, 10H); LRMS calcd for $C_{31}H_{30}Cl_2N_4O$: 544.2, MH+ (observed) 545.2.

Example 63

Preparation of 7-(2,5-Dichlorobenzyl)-3-(2-hydroxyethyl)-3,7-dihydro-4H-pyridazino[4',5':5,6]pyrido[3,4-b]indol-4-one

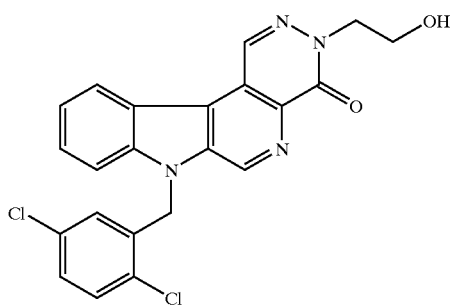

This ring system was prepared by a modification of a reported procedure (Mylari et al., *J. Org. Chem.*, 1991, 56:2587). A solution of 6-(2,5-dichlorobenzyl)-1-hydroxy-1,6-dihydro-3H-furo[3',3':5,6]pyrido[3,4-b]indol-3-one and 1 equivalent of 2-hydroxyethylhydrazine in ethanol (0.033M) was refluxed for 15 hours. The solvent was evaporated, and the product purified by preparative HPLC. $^1$H NMR (300 MHz, DMSO-$d_6$) δ9.48 (s, 1H), 9.29 (s, 1H), 8.78 (d,J=8 Hz, 1H), 7.68 (m, 2H), 7.57 (d,J=8.5 Hz, 1H), 7.48 (m, 1H), 7.37 (dd,J=8.5, 2.5 Hz, 1H), 6.55 (d,J=2.5 Hz, 1H), 6.01 (s, 2H), 4.82 (br s, 1H), 4.28 (t,J=6 Hz, 2H), 3.78 (t,J=6 Hz, 2H); for $C_{22}H_{16}Cl_2N_4$: 438.1, (M+H) found 439.1.

Testing of Compounds for Biochemical Activity

The following assays were conducted to determine the GLP-1 activity when cells are pretreated with the compounds of the present invention:

Assay 1: GLP-1 Binding Assay

Receptor binding was assayed using the cloned human GLP-1 receptor expressed in a baby hamster kidney cell line (BHK). Clones were selected in the presence of 0.5 mg/ml G-418 and were shown to be stable for more than 40 passages.

Plasma membranes were prepared by growing cells to confluence, detaching them from the surface and resuspending the cells in cold buffer (10 mM Tris/HCl), pH 7.4 containing 30 mM NaCl, 1 mM dithiothreitol, 5 mg/L leupeptin, 5 mg/L pepstatin, 100 mg/L bacitracin and 15 mg/L recombinant aprotinin. The cells were homogenized by two 10-second bursts using a Polytron PT 10–35 homogenizer (Kinematica) and centrifuged. The precipitate containing the plasma membranes was suspended in buffer and stored at −80° C. until required.

Binding assays were carried out in duplicate in polypropylene tubes or 96-well plates. The buffer used in this assay was 25 mM HEPES pH 7.4 containing 0.1% bovine serum albumin (Sigma) and 0.01% bacitracin. Typically, 100 μL of sample (GLP-1 or test compound) was added to each tube. Tracer (radio-iodinated GLP-1; 20,000 cpm) was diluted in buffer and 100 μL was added to each tube. Freshly thawed plasma membrane protein (0.5 pg) diluted in buffer was then added in 100 μL aliquots to each tube. The tubes were incubated at 37° C. for 1 hour. Non-specific binding was determined in the presence of 100 nM GLP-1. Bound and unbound tracer were then separated by vacuum filtration. The tubes were washed twice with 3 mL buffer per tube. The filters were counted in a gamma-scintillation counter. Because the radioiodinated GLP-1 is available in high activity, the assays could be carried out under conditions such that the radioiodinated GLP-1 used in the assays represented only 5–10% of the dissociation constant of GLP-1 for the GLP-1 receptor, and hence the measured $IC_{50}$ values of the antagonists closely approximated their $K_i$ values.

Assay 2: GLP-1 Functional Assay

The functional assay determined the ability of the compounds to either right-shift the GLP-1 dose-response curve in a whole-cell cAMP assay or their ability to stimulate cAMP accumulation in these cells. The assay was carried out in borosilicate glass 12×75 tubes. The buffer concentrations in the assay were 10 mM HEPES, 1 mM EGTA, 1.4 mM $MgCl_2$, 0.1 mM IBMX, 30 mM NaCl, 4.7 mM KCl, 2.5 mM $NaH_2PO_4$, 3 mM glucose and 0.2% BSA. The pH was adjusted to 7.4.

In assessing the ability of the compounds to antagonize the GLP-1-mediated cAMP accumulation, cells (typically 0.5 ml, $10^6$/ml) were pretreated with various concentrations of compounds for 10 minutes at 37° C., then challenged with increasing concentrations of GLP-1 for 20 minutes. In determining the ability of the compounds to behave as agonists, cells were treated with various concentrations of the compounds alone. The reactions were terminated by centrifugation, followed by cell lysis with the addition of 500 μL 0.1% HCl. Cellular debris was pelleted and the supernatant containing cAMP evaporated to dryness. cAMP was measured by the use of an RIA kit (New England Nuclear).

Preferred compounds of the invention exhibited $IC_{50}$ binding affinities of less than 1 μM in the GLP-1 binding assay described above, and more preferred compounds had $IC_{50}$ binding affinities less than 100 nM. Because the concentration of iodinated GLP-1 used in the assays represented only 5–10% of the dissociation constant of GLP-1 for the GLP-1 receptor, the $IC_{50}$ values of the antagonists closely approximated their $K_i$ values. None of the compounds tested displayed agonist activity in the GLP-1 functional assay.

PHARMACEUTICAL COMPOSITIONS

The pharmaceutical compositions comprising compounds of the present invention may be manufactured in a manner using known techniques, e.g., by means of conventional mixing, dissolving, granulating, dragee-making, levigating, emulsifying, encapsulating, entrapping or lyophilizing processes. Pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention are formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds are formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use are obtained as a solid excipient, optionally grinding a resulting mixture, adding suitable auxiliaries, if desired, and processing the mixture of granules to obtain tablets or dragee cores. Suitable excipients include fillers such as sugars, including lactose, sucrose, mannitol, or sorbitol, and cellulose preparations, such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents are added, such as cross-linked polyvinyl pyrrolidone, agar, or alginic acid or a salt thereof such as sodium alginate.

Dragee cores are provided with suitable coatings. For this purpose, concentrated sugar solutions are used, which may optionally contain gum arabic, polyvinylpyrrolidone, Carbopol gel, polyethylene glycol, and/or titanium dioxide, lacquer solutions, and suitable organic solvents or solvent mixtures. Dyestuffs or pigments are optionally added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules contain the active ingredients in optional admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In addition, stabilizers are optionally added. All formulations for oral administration are in dosages suitable for such administration. For buccal administration, the compositions take the form of tablets or lozenges formulated in conventional manner.

For administration by inhalation, the compounds for use according to the present invention are conveniently delivered in the form of an aerosol spray presentation from pressurized packs or a nebuliser with the use of a suitable propellant, e.g., dichlorodifluoromethane, trichlorofluoromethane, dichlorotetrafluoroethane, carbon dioxide or other suitable gas. In the case of a pressurized aerosol the dosage unit is determined by providing a valve to deliver a metered amount. Capsules and cartridges of gelatin, for example, for use in an inhaler or insufflator are formulated containing a powder mix of the compound and a suitable powder base such as lactose or starch.

The compounds are formulated for parenteral administration by injection, e.g., by bolus injection or continuous infusion. Formulations for injection are presented in unit dosage form, e.g., in ampoules or in multi-dose containers, with an added preservative. The compositions take such forms as suspensions, solutions or emulsions in oily or aqueous vehicles, and optionally contain formulatory agents such as suspending, stabilizing and/or dispersing agents.

Pharmaceutical formulations for parenteral administration include aqueous solutions of the active compounds in water-soluble form. Additionally, suspensions of the active compounds are prepared as appropriate oily injection suspensions. Suitable lipophilic solvents or vehicles include fatty oils such as sesame oil, or synthetic fatty acid esters, such as ethyl oleate, triglycerides, or liposomes. Aqueous injection suspensions optionally contain substances which increase the viscosity of the suspension, such as sodium carboxymethyl cellulose, sorbitol, or dextran. Optionally, the suspension also contains suitable stabilizers or agents which increase the solubility of the compounds to allow for the preparation of highly concentrated solutions.

Alternatively, the active ingredient is provided in powder form for constitution with a suitable vehicle, e.g., sterile pyrogen-free water, before use. The compounds are also formulated in rectal compositions such as suppositories or retention enemas, e.g., containing conventional suppository bases such as cocoa butter or other glycerides.

In addition to the formulations described previously, the compounds are also formulated as a depot preparation. Such long-acting formulations are administered by implantation (for example, subcutaneously or intramuscularly) or by intramuscular injection. Thus, for example, the compounds are formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system is desirably the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. The proportions of a desirable co-solvent system are varied considerably without destroying its solubility and toxicity characteristics. Furthermore, the identity of the co-solvent components may be varied. For example, other low-toxicity nonpolar surfactants may be used instead of polysorbate 80; the fraction size of polyethylene glycol may be varied; other biocompatible polymers may replace polyethylene glycol, e.g. polyvinylpyrrolidone; and other sugars or polysaccharides may substitute for dextrose.

Alternatively, other delivery systems for hydrophobic pharmaceutical compounds are employed. Liposomes and emulsions are well known examples of delivery vehicles or carriers for hydrophobic drugs. Certain organic solvents such as dimethylsulfoxide also are employed, although usually at the cost of greater toxicity. Additionally, the compounds are delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a period of from a few weeks to up to over 100 days.

The pharmaceutical compositions also comprise suitable solid or gel phase carriers or excipients. Examples of such carriers or excipients include (but are not limited to) calcium carbonate, calcium phosphate, various sugars, starches, cellulose derivatives, gelatin, and polymers such as polyethylene glycols.

Some of the compounds of the invention are provided as salts with pharmaceutically compatible counterions. Pharmaceutically compatible salts may be formed with many acids, including, but not limited to, hydrochloric, sulfuric, acetic, lactic, tartaric, malic, succinic, etc. Salts tend to be more soluble in aqueous or other protonic solvents than are the corresponding free-base forms.

Pharmaceutical compositions suitable for use of the compounds provided by the present invention include compositions wherein the active ingredients are contained in an amount effective to achieve its intended purpose, i.e., to prevent development of or to alleviate the existing symptoms of the subject being treated. Determination of the optimum amount for effecting desired biological, chemical or other effects is well within the capability of those skilled in the art.

For example, a parenteral pharmaceutical composition suitable for administration by injection may include 10 mg of a water-soluble salt of a compound of Formula (I) mixed with 10 mL of 0.9% sterile saline, which is subsequently incorporated into a dosage unit form suitable for administration by injection.

In addition, an oral pharmaceutical composition suitable for administration may include 10 mg of a compound of Formula (I) mixed with 750 mg of lactose, which is subsequently incorporated into a dosage unit form, such as a hard gelatin capsule, for oral administration.

While the invention has been illustrated in reference to specific examples and preferred embodiments, it will be apparent to those skilled in the art that various modifications and variations can be made without departing from the spirit of the invention. Thus, the invention is intended not to be limited by the foregoing description, but to be defined by the following claims and their equivalents.

What is claimed is:
1. A compound of formula:

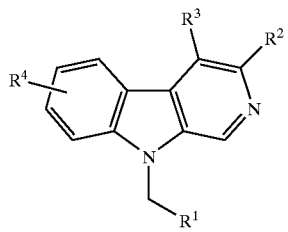

wherein:
$R^1$ is a phenyl or pyridyl group optionally substituted with one or more substituents independently selected from the group consisting of halogen, hydroxyl, nitro, trifluoromethyl, cyano, $C_1$–$C_6$ alkyl, $C_2$–$C_6$ alkenyl, and $C_1$–$C_6$ alkoxy groups;

$R^2$ is:

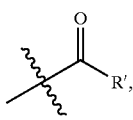

where R' is: hydrogen; a hydroxy group; —$OR^5$, where $R^5$ is a $C_1$–$C_6$ alkyl or $C_2$–$C_6$ alkenyl group optionally substituted with a hydroxy group or an amino, $C_1$–$C_6$ alkoxy, cycloalkyl, thioether, heterocycloalkyl, aryl, or heteroaryl group optionally substituted with one or more substituents independently selected from the group consisting of alkyl, hydroxyalkyl, carboxyl, $C_1$–$C_6$ alkoxycarbonyl, oxygen, halogen, and trifluoromethyl groups; or —$NR^6R^7$, where $R^6$ and $R^7$ are each independently hydrogen or a $C_1$–$C_6$ alkyl, $C_2$–$C_6$ alkenyl, amino, or imino group optionally substituted with a hydroxy group, a $C_1$–$C_6$ alkoxy group, or an amino, thioether, heterocycloalkyl, aryl, or heteroaryl group optionally substituted with one or more substituents independently selected from the group consisting of oxygen, halogen, trifluoromethyl, and carboxyl groups, or where —$NR^6R^7$ forms a 5- or 6-membered heterocyclic ring optionally containing, in addition to the nitrogen heteroatom, a heteroatom selected from the group consisting of O, N, and S;
—$(CH_2)_n$—O—R''', where n is 1 or 2, and R'' is hydrogen, a $C_5$–$C_7$ heteroaryl group, or

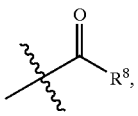

where $R^8$ is hydrogen, a $C_1$–$C_6$ alkyl group, a $C_3$–$C_6$ cycloalkyl group, or a 5- or 6-membered heteroaryl group optionally substituted with one or more substituents independently selected from the group consisting of halogens, methyl, and trifluoromethyl;
—$(CH_2)_p$—N(R'')(R'''), where p is 1 or 2, R'' is as defined above, and R''' is hydrogen or an alkyl or alkoxy group optionally substituted with a $C_3$–$C_6$ cycloalkyl group optionally substituted with cyano;
—CH=N—R'''', where R'''' is hydrogen, a hydroxy group, or —$OR^9$, where $R^9$ is an alkyl, cycloalkyl, aryl, or heteroaryl group; or a 5- or 6-membered heterocyclic ring containing one to three heteroatoms independently selected from the group consisting of O, N, and S, the ring being optionally substituted with one or two substituents independently selected from the group consisting of methyl, methoxymethyl, oxygen, and $C_1$–$C_6$ alkoxy groups;

$R^3$ is hydrogen or a $C_1$–$C_6$ alkyl, $C_2$–$C_6$ alkenyl, or ($C_1$–$C_3$ alkoxy)$C_1$–$C_3$ alkyl group;

or $R^2$ and $R^3$ together with the atoms to which they are bound form a 5- or 6-membered ring containing one or two heteroatoms selected from the group consisting of O, N, and S, the ring being optionally substituted with oxygen, hydroxyl, or a $C_1$–$C_6$ alkyl group optionally substituted with a 5- or 6-membered heterocycloalkyl containing one or two heteroatoms independently selected from the group consisting of O, N, and S; and $R^4$ is hydrogen or an amino, halogen, hydroxyl, nitro, trifluoromethyl, cyano, $C_1$–$C_6$ alkyl, or $C_2$–$C_6$ alkenyl group:

where when $R^1$ is an unsubstituted phenyl, $R^2$ is

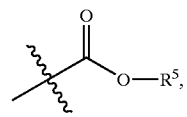

$R^3$ is H, and $R^4$ is H, $R^5$ is not an ethyl group;
pharmaceutically acceptable salt or pharmaceutically acceptable solvate of said compound.

2. A compound, pharmaceutically acceptable salt, or pharmaceutically acceptable solvate according to claim 1, wherein:

$R^1$ is a phenyl group optionally substituted with one or more substituents selected from the group consisting of halogen, hydroxyl, nitro, trifluoromethyl, and cyano groups;

$R^2$ is

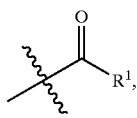

where R' is as defined above and wherein a hydrogen-bond acceptor substituent is positioned 3–5 Å from the carbonyl group; and $R^3$ is hydrogen or methoxymethyl.

3. A compound, pharmaceutically acceptable salt, or pharmaceutically acceptable solvate according to claim 1, wherein $R^1$ is 2,5-dichlorophenyl or 3,5-dinitrophenyl.

4. A compound, pharmaceutically acceptable salt, or pharmaceutically acceptable solvate according to claim 1, wherein $R^2$ and $R^3$ together with the atoms to which they are bound form a 5- or 6-membered ring that is a lactone or lactam.

5. A compound, pharmaceutically acceptable salt or pharmaceutically acceptable solvate according to claim 1, wherein $R^2$ is selected from the group consisting of:

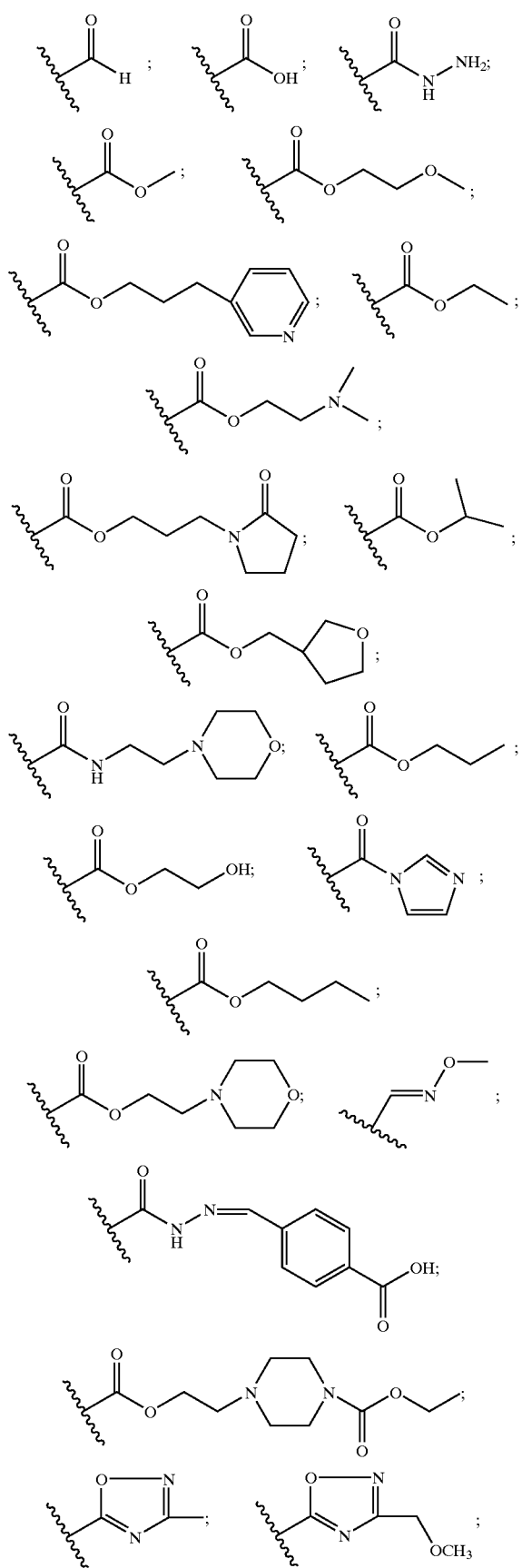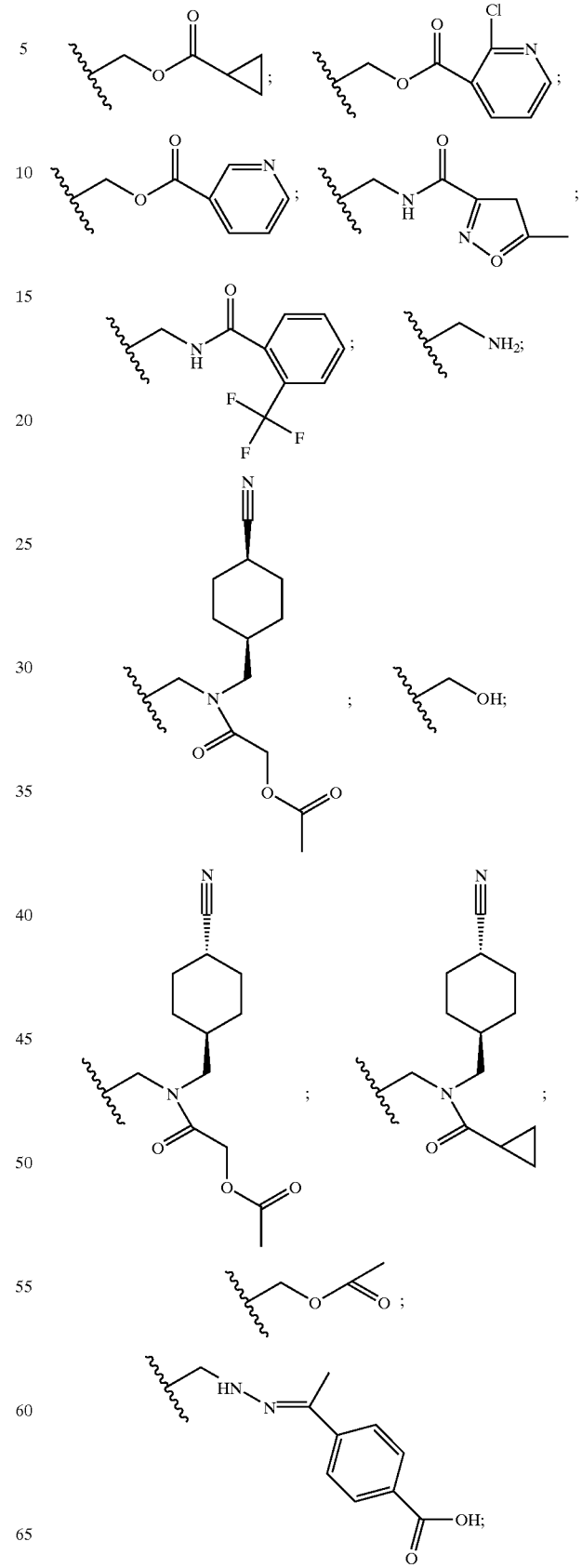

-continued

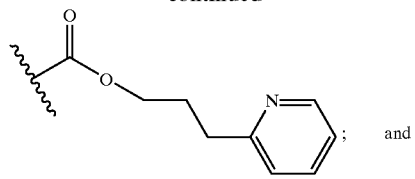

; and

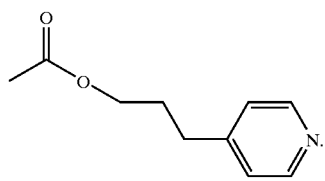

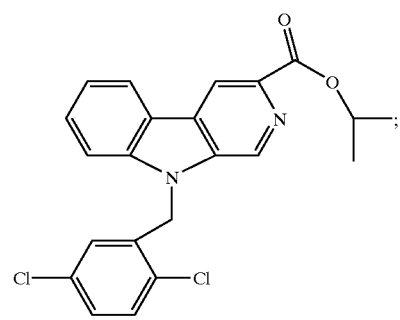

6. A compound pharmaceutically acceptable salt, or pharmaceutically acceptable solvate according to claim 1, wherein $R^2$ and $R^3$ and the atoms to which they are bound together form a 5- to 6-membered ring selected from the group consisting of:

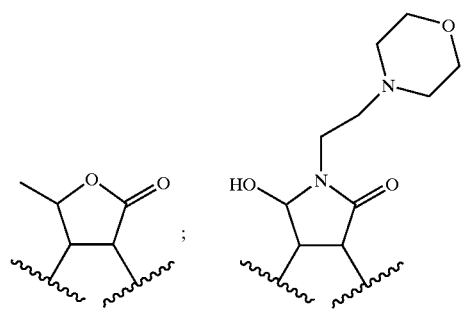

; and

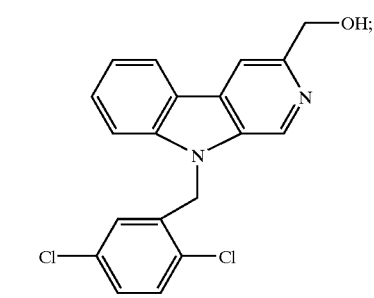

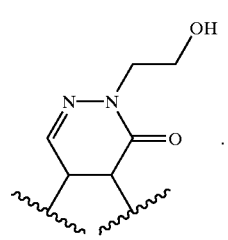

.

7. A compound, pharmaceutically acceptable salt, or pharmaceutically acceptable solvate according to claim 1, wherein the compound is of the formula:

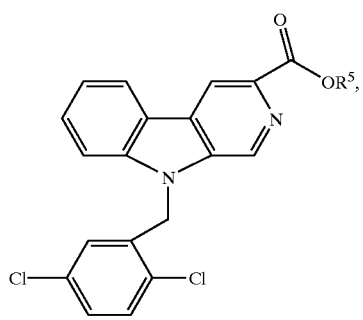

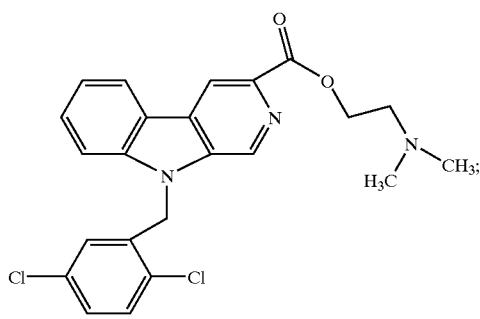

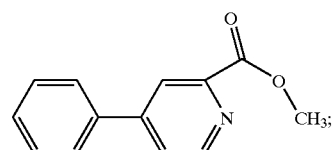

where $R^5$ is as defined above.

8. A compound, pharmaceutically acceptable salt, or pharmaceutically acceptable solvate according to claim 1, wherein the compound is selected from the group consisting of:

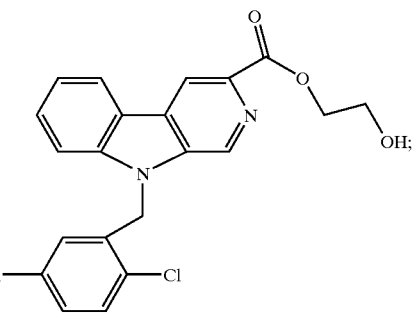

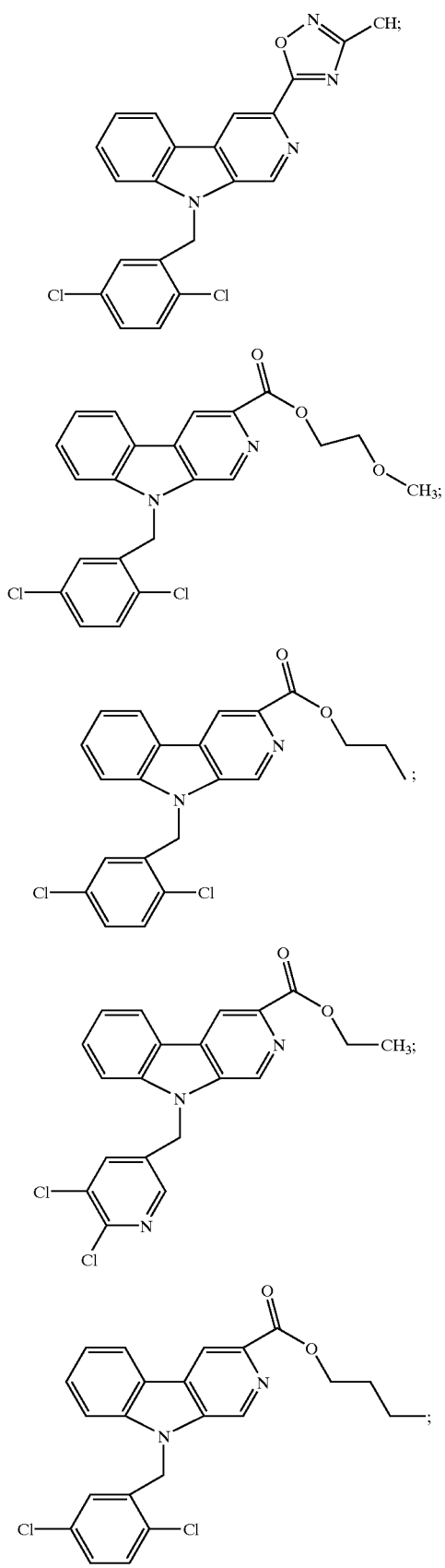
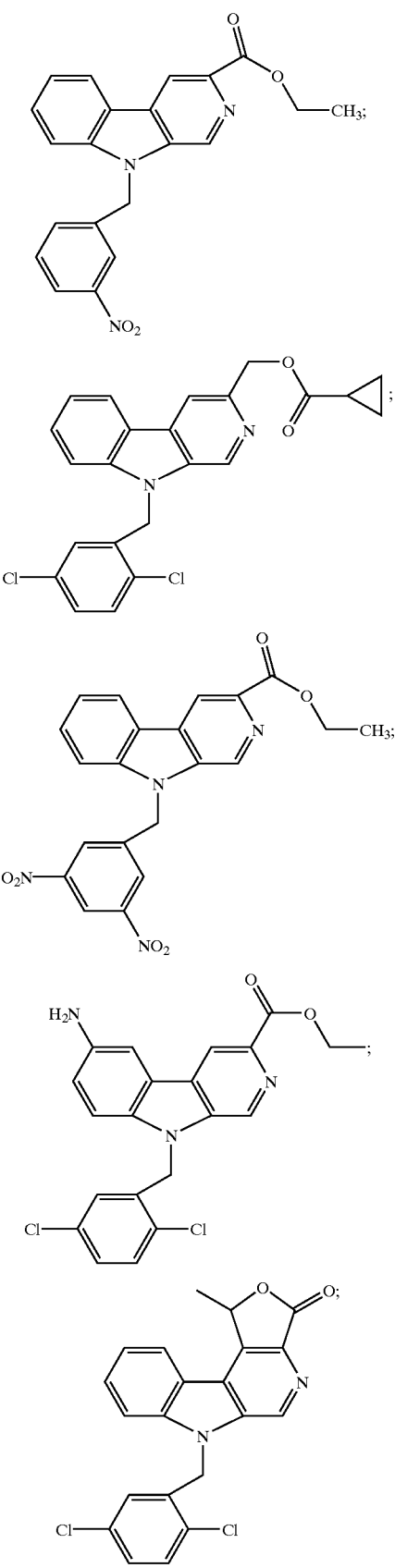

79
-continued
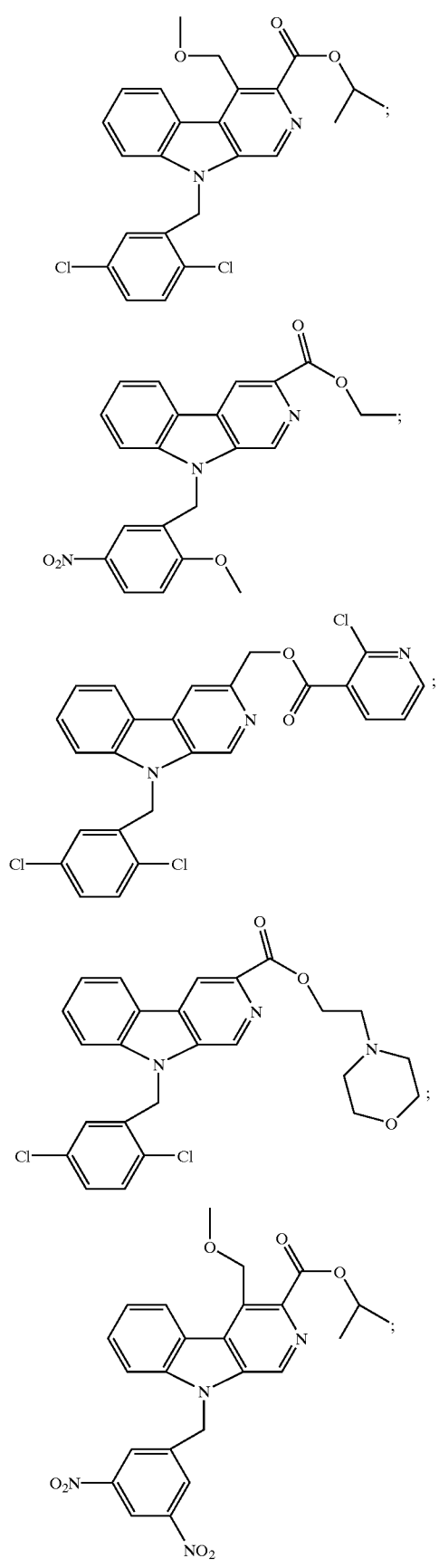
80
-continued
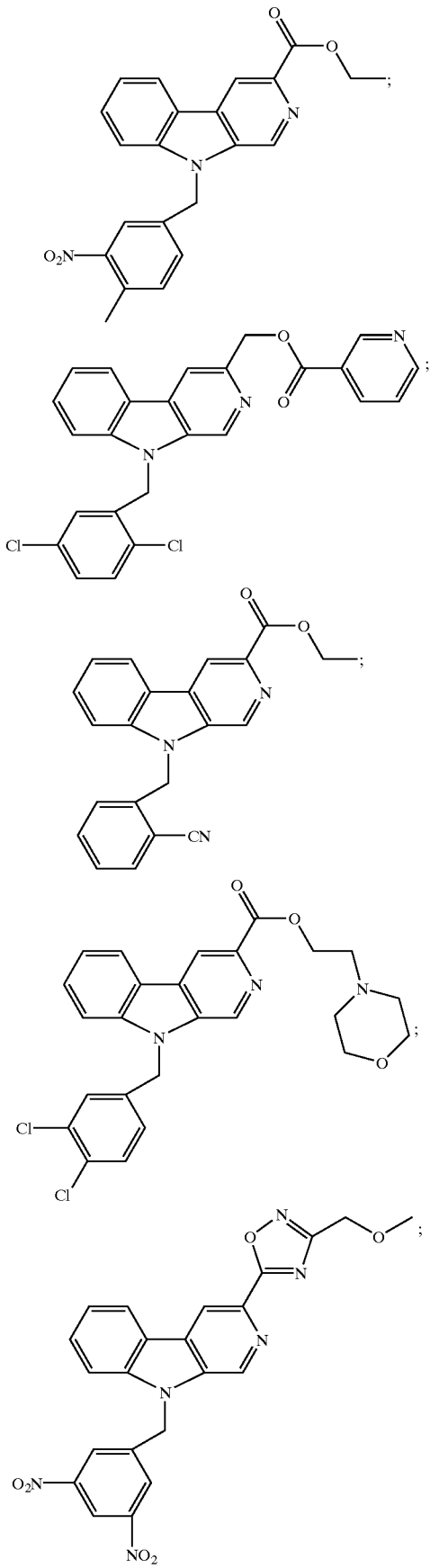

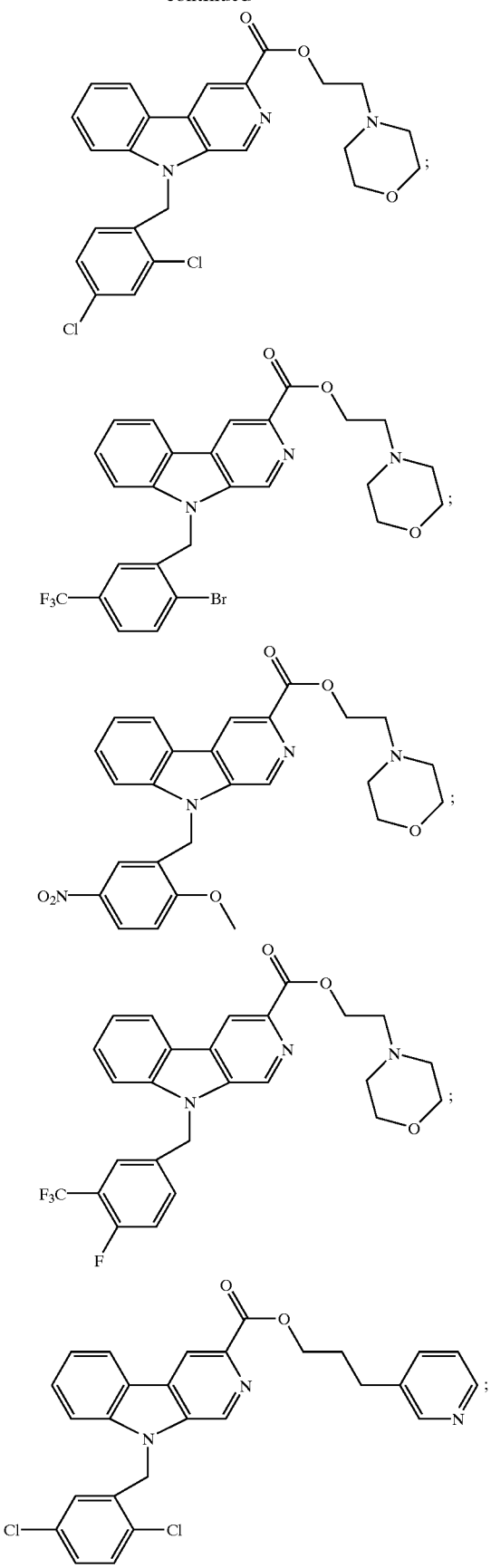
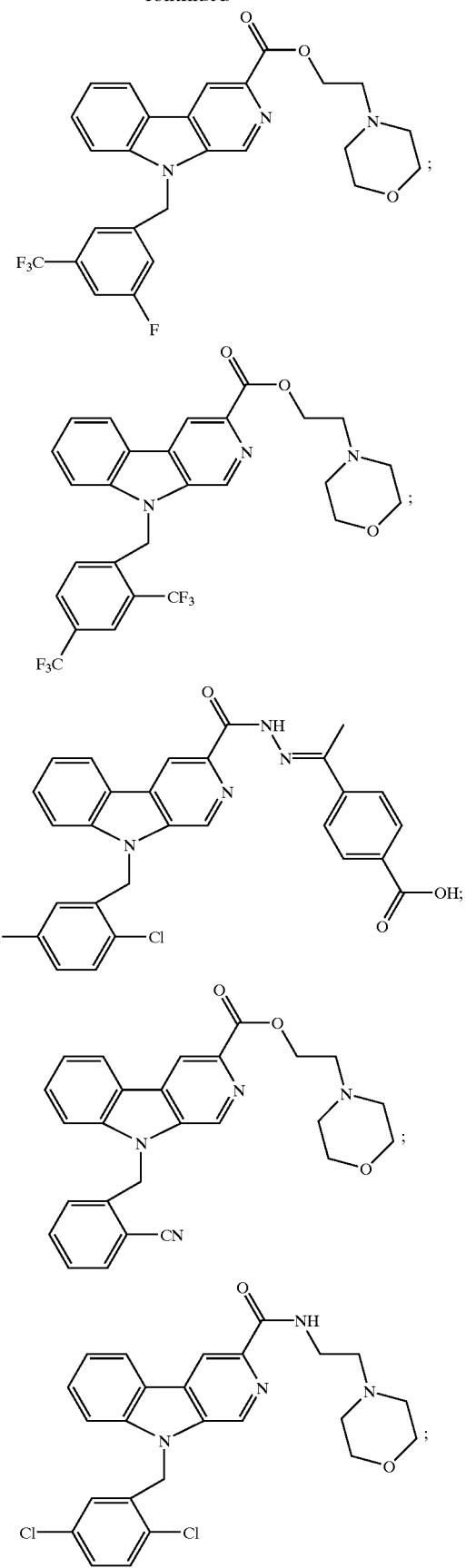

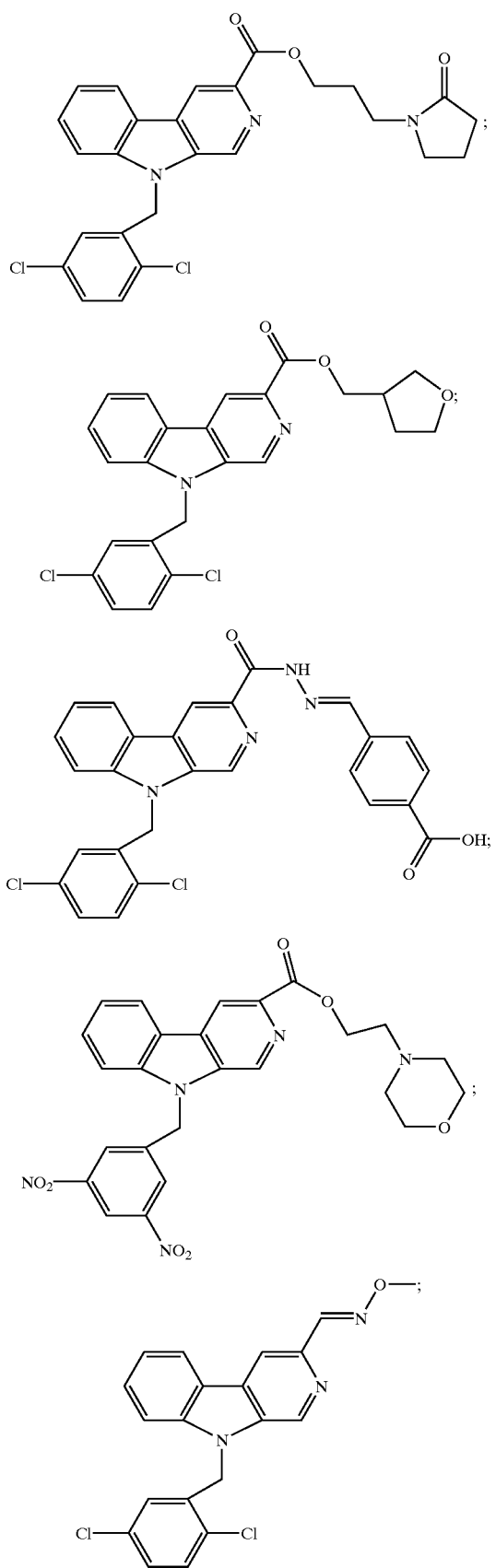
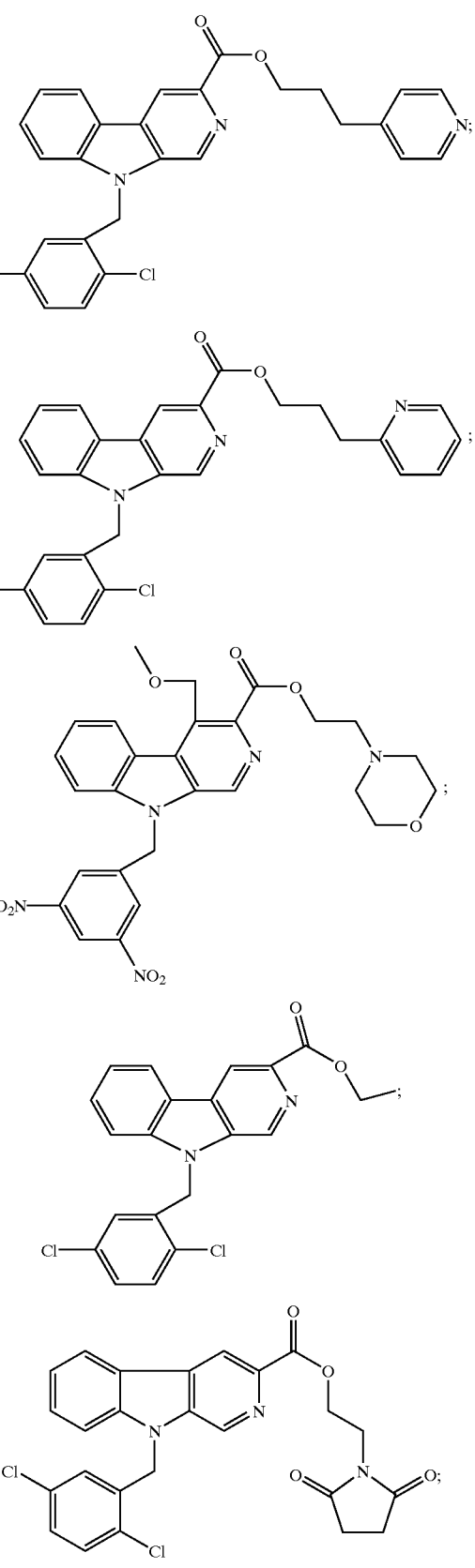

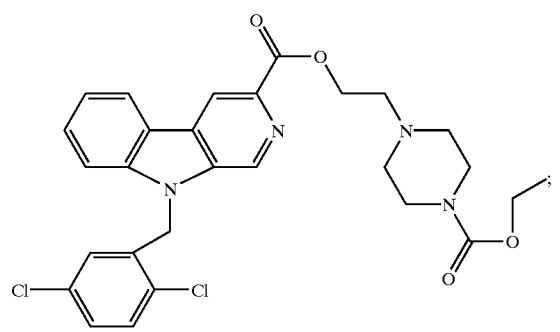
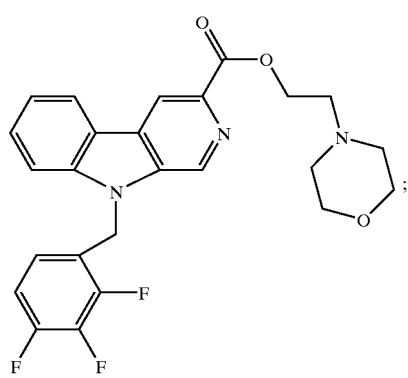
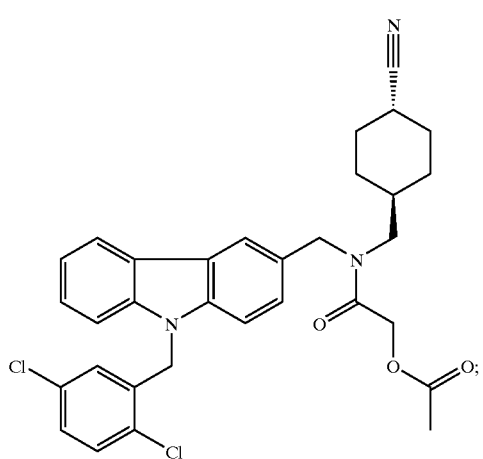
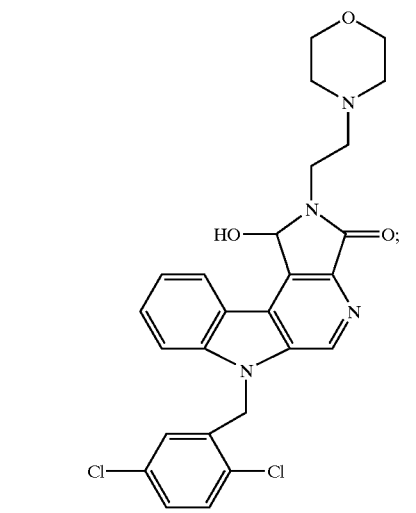
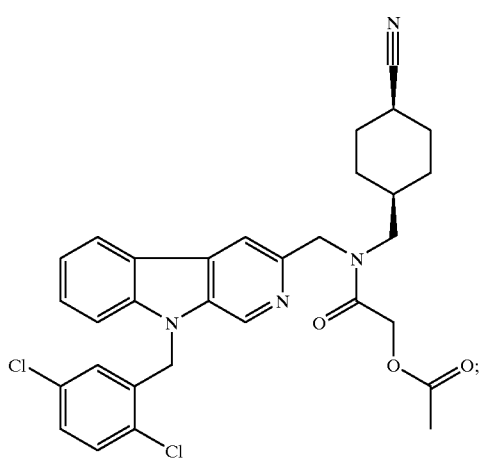
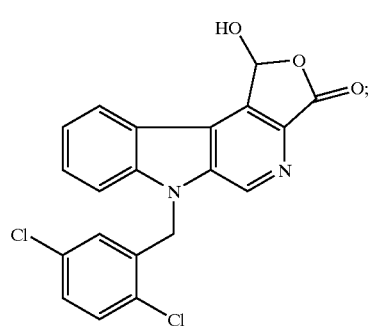
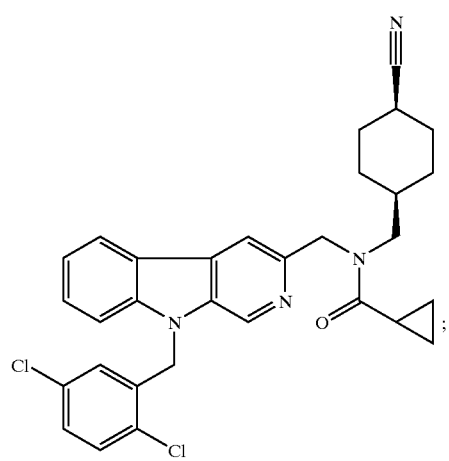
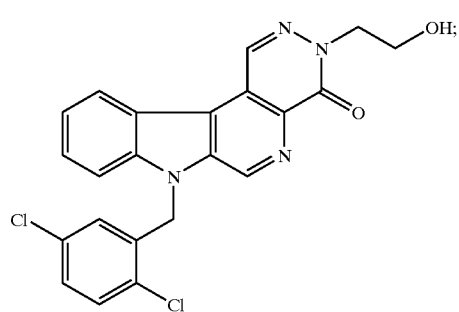

-continued

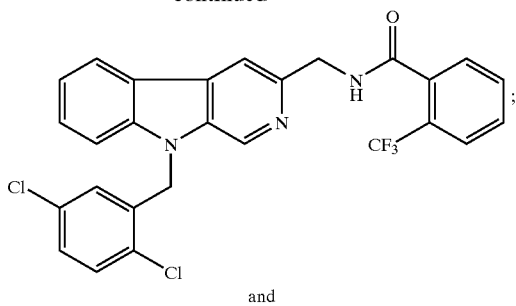

and

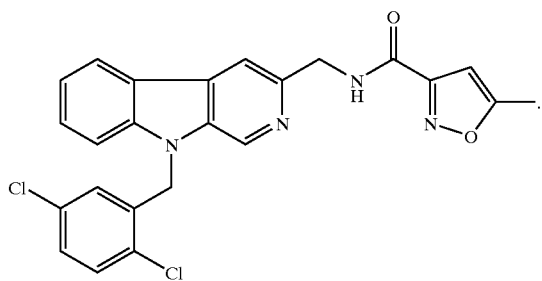

9. A pharmaceutical composition comprising an effective amount of a compound, pharmaceutically acceptable salt, or pharmaceutically acceptable solvate according to claim 1, and a pharmaceutically acceptable carrier.

10. A method for regulating the secretion of insulin in mammals comprising administering to a mammal an effective amount of a compound of formula:

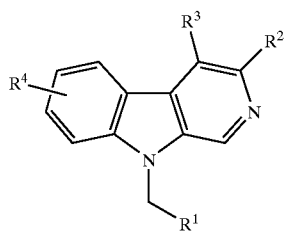

wherein:

1e;.5q$R^1$ is a phenyl or pyridyl group optionally substituted with one or more substituents independently selected from the group consisting of halogen, hydroxyl, nitro, trifluoromethyl, cyano, $C_1$–$C_6$ alkyl, $C_2$–$C_6$ alkenyl, and $C_1$–$C_6$ alkoxy groups;

$R^2$ is:

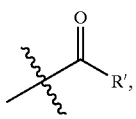

where R' is: hydrogen; a hydroxy group; —$OR^5$, where $R^5$ is a $C_1$–$C_6$ alkyl or $C_2$–$C_6$ alkenyl group optionally substituted with a hydroxy group or an amino, $C_1$–$C_6$ alkoxy, cycloalkyl, thioether, heterocycloalkyl, aryl, or heteroaryl group optionally substituted with one or more substituents independently selected from the group consisting of alkyl, hydroxyalkyl, carboxyl, $C_1$–$C_6$ alkoxycarbonyl, oxygen, halogen, and trifluoromethyl groups; or —$NR^6R^7$, where $R^6$ and $R^7$ are each independently hydrogen or a $C_1$–$C_6$ alkyl, $C_2$–$C_6$ alkenyl, amino, or imino group optionally substituted with a hydroxy group, a $C_1$–$C_6$ alkoxy group, or an amino, thioether, heterocycloalkyl, aryl or heteroaryl group optionally substituted with one or more substituents independently selected from the group consisting of oxygen, halogen, trifluoromethyl, and carboxyl groups, or where —$NR^6R^7$ forms a 5- or 6-membered heterocyclic ring optionally containing, in addition to the nitrogen heteroatom, a heteroatom selected from the group consisting of O, N, and S;

—$(CH_2)_n$—O—R", where n is 1 or 2, and R" is hydrogen, a $C_5$–$C_7$ heteroaryl group, or

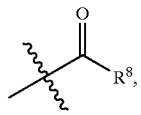

where $R^8$ is hydrogen, a $C_1$–$C_6$ alkyl group, a $C_3$–$C_6$ cycloalkyl group, or a 5- or 6-membered heteroaryl group optionally substituted with one or more substituents independently selected from the group consisting of halogens, methyl, and trifluoromethyl;

—$(CH_2)_p$—N(R")(R'"), where p is 1 or 2, R" is as defined above, and R'" is hydrogen or an alkyl or alkoxy group optionally substituted with a $C_3$–$C_6$ cycloalkyl group optionally substituted with cyano;

—CH=N—R"", where R"" is hydrogen, a hydroxy group, or —$OR^9$, where $R^9$ is an alkyl, cycloalkyl, aryl, or heteroaryl group; or a 5- or 6-membered heterocyclic ring containing one to three heteroatoms independently selected from the group consisting of O, N, and S, the ring being optionally substituted with one or two substituents independently selected from the group consisting of methyl, methoxymethyl, oxygen, and $C_1$–$C_6$ alkoxy groups;

$R^3$ is hydrogen or a $C_1$–$C_6$ alkyl, $C_2$–$C_6$ alkenyl, or ($C_1$–$C_3$ alkoxy)$C_1$–$C_3$ alkyl group;

or $R^2$ and $R^3$ together with the atoms to which they are bound form a 5- or 6-membered ring containing one or two heteroatoms selected from the group consisting of O, N, and S, the ring being optionally substituted with oxygen, hydroxyl, or a $C_1$–$C_6$ alkyl group optionally substituted with a 5- or 6-membered heterocycloalkyl containing one or two heteroatoms independently selected from the group consisting of O, N, and S; and $R^4$ is hydrogen or an amino, halogen, hydroxyl, nitro, trifluoromethyl, cyano, $C_1$–$C_6$ alkyl, or $C_2$–$C_6$ alkenyl group;

pharmaceutically acceptable salt, or pharmaceutically acceptable solvate of said compound.

11. A method for inhibiting GLP-1 activity comprising administering to a patient an effective amount of a compound of formula:

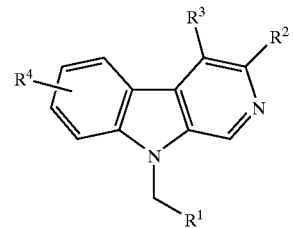

wherein:

$R^1$ is a phenyl or pyridyl group optionally substituted with one or more substituents independently selected from the group consisting of halogen, hydroxyl, nitro, trifluoromethyl, cyano, $C_1$–$C_6$ alkyl, $C_2$–$C_6$ alkenyl, and $C_1$–$C_6$ alkoxy groups;

89

R² is:

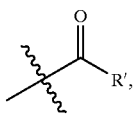

where R' is: hydrogen; a hydroxy group; —OR⁵, where R⁵ is a $C_1$–$C_6$ alkyl or $C_2$–$C_6$ alkenyl group optionally substituted with a hydroxy group or an amino, $C_1$–$C_6$ alkoxy, cycloalkyl, thioether, heterocycloalkyl, aryl, or heteroaryl group optionally substituted with one or more substituents independently selected from the group consisting of alkyl, hydroxyalkyl, carboxyl, $C_1$–$C_6$ alkoxycarbonyl, oxygen, halogen, and trifluoromethyl groups; or –NR⁶R⁷, where R⁶ and R⁷ are each independently hydrogen or a $C_1$–$C_6$ alkyl, $C_2$–$C_6$ alkenyl, amino, or imino group optionally substituted with a hydroxy group, a $C_1$–$C_6$ alkoxy group, or an amino, thioether, heterocycloalkyl, aryl, or heteroaryl group optionally substituted with one or more substituents independently selected from the group consisting of oxygen, halogen, trifluoromethyl, and carboxyl groups, or where —NR⁶R⁷ forms a 5- or 6-membered heterocyclic ring optionally containing, in addition to the nitrogen heteroatom, a heteroatom selected from the group consisting of O, N, and S;

—(CH₂)—O—R", where n is 1 or 2, and R" is hydrogen, a $C_5$–$C_7$heteroaryl group, or

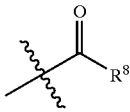

where R⁸ is hydrogen, a $C_1$–$C_6$ alkyl group, a $C_3$–$C_6$ cycloalkyl group, or a 5- or 6-membered heteroaryl group optionally substituted with one or more substituents independently selected from the group consisting of halogens, methyl, and trifluoromethyl;

—(CH₂)$_p$—N(R")(R'''), where p is 1 or 2, R" is as defined above, and R''' is hydrogen or an alkyl or alkoxy group optionally substituted with a $C_3$–$C_6$ cycloalkyl group optionally substituted with cyano;

—CH=N—R"", where R"" is hydrogen, a hydroxy group, or —OR⁹, where R⁹ is an alkyl, cycloalkyl, aryl, or heteroaryl group; or a 5- or 6-membered heterocyclic ring containing one to three heteroatoms independently selected from the group consisting of O, N, and S, the ring being optionally substituted with one or two substituents independently selected from the group consisting of methyl, methoxymethyl, oxygen, and $C_1$–$C_6$ alkoxy groups;

R³ is hydrogen or a $C_1$–$C_6$ alkyl, $C_2$–$C_6$ alkenyl, or ($C_1$–$C_3$ alkoxy)$C_1$–$C_3$ alkyl group;

or R² and R³ together with the atoms to which they are bound form a 5- or 6-membered ring containing one or two heteroatoms selected from the group consisting of O, N, and S, the ring being optionally substituted with oxygen, hydroxyl, or a $C_1$–$C_6$ alkyl group optionally substituted with a 5- or 6-membered heterocycloalkyl containing one or two heteroatoms independently selected from the group consisting of O, N, and S; and R⁴ is hydrogen or an amino, halogen, hydroxyl, nitro, trifluoromethyl, cyano, $C_1$–$C_6$ alkyl, or $C_2$–$C_6$ alkenyl group;

90 pharmaceutically acceptable salt or pharmaceutically acceptable solvate of said compound.

12. A method of inhibiting the binding of GLP-1 to the GLP-1 receptor comprising administering to a patient an effective amount of a compound of formula:

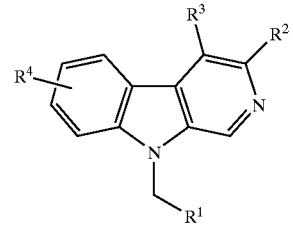

wherein:

R¹ is a phenyl or pyridyl group optionally substituted with one or more substituents independently selected from the group consisting of halogen, hydroxyl, nitro, trifluoromethyl, cyano, $C_1$–$C_6$ alkyl, $C_2$–$C_6$ alkenyl, and $C_1$–$C_6$ alkoxy groups;

R² is:

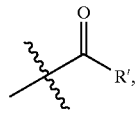

where R' is: hydrogen; a hydroxy group; —OR⁵, where R⁵ is a $C_1$–$C_6$ alkyl or $C_2$–$C_6$ alkenyl group optionally substituted with a hydroxy group or an amino, $C_1$–$C_6$ alkoxy, cycloalkyl, thioether, heterocycloalkyl, aryl, or heteroaryl group optionally substituted with one or more substituents independently selected from the group consisting of alkyl, hydroxyalkyl, carboxyl, $C_1$–$C_6$ alkoxycarbonyl, oxygen, halogen, and trifluoromethyl groups; or —NR⁶R⁷, where R⁶ and R⁷ are each independently hydrogen or a $C_1$–$C_6$ alkyl, $C_2$–$C_6$ alkenyl, amino, or imino group optionally substituted with a hydroxy group, a $C_1$–$C_6$ alkoxy group, or an amino, thioether, heterocycloalkyl, aryl, or heteroaryl group optionally substituted with one or more substituents independently selected from the group consisting of oxygen, halogen, trifluoromethyl, and carboxyl groups, or where —NR⁶R⁷ forms a 5- or 6-membered heterocyclic ring optionally containing, in addition to the nitrogen heteroatom, a heteroatom selected from the group consisting of O, N, and S;

—(CH₂)$_n$—O—R", where n is 1 or 2, and R" is hydrogen, a $C_5$–$C_7$heteroaryl group, or

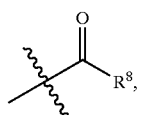

where R₈ is hydrogen, a $C_1$–$C_6$ alkyl group, a $C_3$–$C_6$ cycloalkyl group, or a 5- or 6-membered heteroaryl group optionally substituted with one or more substituents independently selected from the group consisting of halogens, methyl, and trifluoromethyl;

—(CH₂)$_p$—N(R")(R'''), where p is 1 or 2, R" is as defined above and R''' is hydrogen or an alkyl or alkoxy group optionally substituted with a $C_3$–$C_6$ cycloalkyl group optionally substituted with cyano;

—CH=N—R"", where R"" is hydrogen, a hydroxy group, or —OR$^9$, where R$^9$ is an alkyl, cycloalkyl, aryl, or heteroaryl group; or a 5- or 6-membered heterocyclic ring containing one to three heteroatoms independently selected from the group consisting of O, N, and S, the ring being optionally substituted with one or two substituents independently selected from the group consisting of methyl, methoxymethyl, oxygen, and C$_1$–C$_6$ alkoxy groups;

R$^3$ is hydrogen or a C$_1$–C$_6$ alkyl, C$_2$–C$_6$ alkenyl, or (C$_3$–C$_3$ alkoxy)C$_{1-C3}$ alkyl group;

or R$^2$ and R$^3$ together with the atoms to which they are bound form a 5- or 6-membered ring containing one or two heteroatoms selected from the group consisting of O, N, and S, the ring being optionally substituted with oxygen, hydroxyl, or a C$_1$–C$_6$ alkyl group optionally substituted with a 5- or 6-membered heterocycloalkyl containing one or two heteroatoms independently selected from the group consisting of O, N, and S; and R$^4$ is hydrogen or an amino, halogen, hydroxyl, nitro, trifluoromethyl, cyano, C$_1$–C$_6$ alkyl, or C$_2$–C$_6$ alkenyl group;

pharmaceutically acceptable salt, or pharmaceutically acceptable solvate or active metabolite of said compound.

13. A method of inhibiting activation of the GLP-1 receptor comprising administering to a patient an effective amount of a compound of formula:

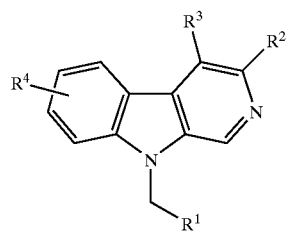

wherein:
R$^1$ is a phenyl or pyridyl group optionally substituted with one or more substituents independently selected from the group consisting of halogen, hydroxyl, nitro, trifluoromethyl, cyano, C$_1$–C$_6$ alkyl, C$_2$–C$_6$ alkenyl, and C$_1$–C$_6$ alkoxy groups;

R$^2$ is:

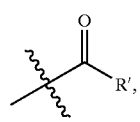

where R' is: hydrogen; a hydroxy group; —OR$^5$, where R$^5$ is a C$_1$–C$_6$ alkyl or C$_2$–C$_6$ alkenyl group optionally substituted with a hydroxy group or an amino, C$_1$–C$_6$ alkoxy, cycloalkyl, thioether, heterocycloalkyl, aryl, or heteroaryl group optionally substituted with one or more substituents independently selected from the group consisting of alkyl, hydroxyalkyl, carboxyl, C$_1$–C$_6$ alkoxycarbonyl, oxygen, halogen, and trifluoromethyl groups; or —NR$^6$R$^7$, where R$^6$ and R$^7$ are each independently hydrogen or a C$_1$–C$_6$ alkyl, C$_2$–C$_6$ alkenyl, amino, or imino group optionally substituted with a hydroxy group, a C$_1$–C$_6$ alkoxy group, or an amino, thioether, heterocycloalkyl, aryl, or heteroaryl group optionally substituted with one or more substituents independently selected from the group consisting of oxygen, halogen, trifluoromethyl, and carboxyl groups, or where —NR$^6$R$^7$ forms a 5- or 6-membered heterocyclic ring optionally containing, in addition to the nitrogen heteroatom, a heteroatom selected from the group consisting of O, N, and S;

—(CH$_2$)$_n$—O—R", where n is 1 or 2, and R" is hydrogen, a C$_5$–C$_7$ heteroaryl group, or

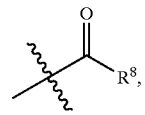

or where R$^8$ is hydrogen, a C$_1$–C$_6$ alkyl group, a C$_3$–C$_6$ cycloalkyl group, or a 5- or 6-membered heteroaryl group optionally substituted with one or more substituents independently selected from the group consisting of halogens, methyl, and trifluoromethyl;

—(CH$_2$)$_p$—N(R")(R'''), where p is 1 or 2, R" is as defined above, and R''' is hydrogen or an alkyl or alkoxy group optionally substituted with a C$_3$–C$_6$ cycloalkyl group optionally substituted with cyano;

—CH=N—R"", where R"" is hydrogen, a hydroxy group, or —OR$^9$, where R$^9$ is an alkyl, cycloalkyl, aryl, or heteroaryl group; or a 5- or 6-membered heterocyclic ring containing one to three heteroatoms independently selected from the group consisting of O, N, and S, the ring being optionally substituted with one or two substituents independently selected from the group consisting of methyl, methoxymethyl, oxygen, and C$_1$–C$_6$ alkoxy groups;

R$^3$ is hydrogen or a C$_1$–C$_6$ alkyl, C$_2$–C$_6$ alkenyl, or (C$_1$–C$_3$ alkoxy)C$_1$–C$_3$ alkyl group;

or R$^2$ and R$^3$ together with the atoms to which they are bound form a 5- or 6-membered ring containing one or two heteroatoms selected from the group consisting of O, N, and S, the ring being optionally substituted with oxygen, hydroxyl, or a C$_1$–C$_6$ alkyl group optionally substituted with a 5- or 6-membered heterocycloalkyl containing one or two heteroatoms independently selected from the group consisting of O, N, and S; and R$^4$ is hydrogen or an amino, halogen, hydroxyl, nitro, trifluoromethyl, cyano, C$_1$–C$_6$ alkyl, or C$_2$–C$_6$ alkenyl group;

pharmaceutically acceptable salt, or pharmaceutically acceptable solvate of said compound.

14. A method for regulating the secretion of insulin in mammals comprising administering to a mammal an effective amount of a compound of formula:

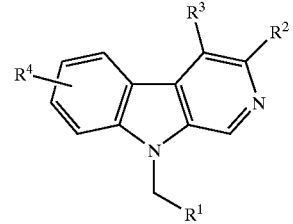

wherein:
R$^1$ is a phenyl or pyridyl group optionally substituted with one or more substituents independently selected from the group consisting of halogen, hydroxyl, nitro, trifluoromethyl, cyano, $C_1$–$C_6$ alkyl, $C_2$–$C_6$ alkenyl, and $C_1$–$C_6$ alkoxy groups;

$R^2$ is:

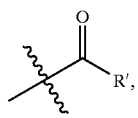

where R' is: hydrogen; a hydroxy group; —$OR^5$, where $R^5$ is a $C_1$–$C_6$ alkyl or $C_2$–$C_6$ alkenyl group optionally substituted with a hydroxy group or an amino, $C_1$–$C_6$ alkoxy, cycloalkyl, thioether, heterocycloalkyl, aryl, or heteroaryl group optionally substituted with one or more substituents independently selected from the group consisting of alkyl, hydroxyalkyl, carboxyl, $C_1$–$C_6$ alkoxycarbonyl, oxygen, halogen, and trifluoromethyl groups; or —$NR^6R^7$, where $R^6$ and $R^7$ are each independently hydrogen or a $C_1$–$C_6$ alkyl, $C_2$–$C_6$ alkenyl, amino, or imino group optionally substituted with a hydroxy group, a $C_1$–$C_6$ alkoxy group, or an amino, thioether, heterocycloalkyl, aryl, or heteroaryl group optionally substituted with one or more substituents independently selected from the group consisting of oxygen, halogen, trifluoromethyl, and carboxyl groups, or where —$NR^6R^7$ forms a 5- or 6-membered heterocyclic ring optionally containing, in addition to the nitrogen heteroatom, a heteroatom selected from the group consisting of O, N, and S;

—$(CH_2)_n$—O—R'', where n is 1 or 2, and R'' is hydrogen, a $C_5$–$C_7$ heteroaryl group, or

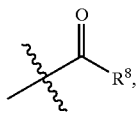

where $R^8$ is hydrogen, a $C_1$–$C_6$ alkyl group, a $C_3$–$C_6$ cycloalkyl group, or a 5- or 6-membered heteroaryl group optionally substituted with one or more substituents independently selected from the group consisting of halogens, methyl, and trifluoromethyl;

—$(CH_2)_p$—N(R'')(R'''), where p is 1 or 2, R' is as defined above, and R''' is hydrogen or an alkyl or alkoxy group optionally substituted with a $C_3$–$C_6$ cycloalkyl group optionally substituted with cyano;

—CH=N—R'''', where R'''' is hydrogen, a hydroxy group, or —$OR^9$, where $R^9$ is an alkyl, cycloalkyl, aryl, or heteroaryl group; or a 5- or 6-membered heterocyclic ring containing one to three heteroatoms independently selected from the group consisting of O, N, and S, the ring being optionally substituted with one or two substituents independently selected from the group consisting of methyl, methoxymethyl, oxygen, and $C_1$–$C_6$ alkoxy groups;

$R^3$ is hydrogen or a $C_1$–$C_6$ alkyl, $C_2$–$C_6$ alkenyl, or ($C_1$–$C_3$ alkoxy)$C_1$–$C_3$ alkyl group;

or $R^2$ and $R^3$ together with the atoms to which they are bound form a 5- or 6-membered ring containing one or two heteroatoms selected from the group consisting of O, N, and S, the ring being optionally substituted with oxygen, hydroxyl, or a $C_1$–$C_6$ alkyl group optionally substituted with a 5- or 6-membered heterocycloalkyl containing one or two heteroatoms independently selected from the group consisting of O, N, and S; and $R^4$ is hydrogen or an amino, halogen, hydroxyl, nitro, trifluoromethyl, cyano, $C_1$–$C_6$ alkyl, or $C_2$–$C_6$ alkenyl group;

pharmaceutically acceptable salt, or pharmaceutically acceptable solvate of said compound.

15. A compound of formula:

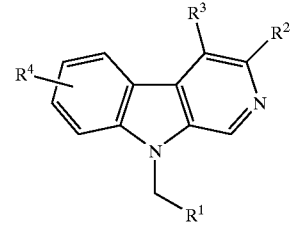

wherein:

$R^1$ is a phenyl or pyridyl group optionally substituted with one or more substituents independently selected from the group consisting of halogen, hydroxyl, nitro, trifluoromethyl, cyano, $C_1$–$C_6$ alkyl, $C_2$–$C_6$ alkenyl, and $C_1$–$C_6$ alkoxy groups;

$R^2$ is:

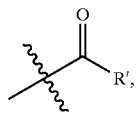

where R' is: hydrogen; a hydroxy group; —$OR^5$, where $R^5$ is a $C_1$–$C_6$ alkyl or $C_2$–$C_6$ alkenyl group optionally substituted with a hydroxy group or an amino, $C_1$–$C_6$ alkoxy, cycloalkyl, thioether, heterocycloalkyl, aryl, or heteroaryl group optionally substituted with one or more substituents independently selected from the group consisting of alkyl, hydroxyalkyl, carboxyl, $C_1$–$C_6$ alkoxycarbonyl, oxygen, halogen, and trifluoromethyl groups; or —$NR^6R^7$, where $R^6$ and $R^7$ are each independently hydrogen or a $C_1$–$C_6$ alkyl, $C_2$–$C_6$ alkenyl, amino, or imino group optionally substituted with a hydroxy group, a $C_1$–$C_6$ alkoxy group, or an amino, thioether, heterocycloalkyl, aryl, or heteroaryl group optionally substituted with one or more substituents independently selected from the group consisting of oxygen, halogen, trifluoromethyl, and carboxyl groups, or where —$NR^6R^7$ forms a 5- or 6-membered heterocyclic ring optionally containing, in addition to the nitrogen heteroatom, a heteroatom selected from the group consisting of O, N, and S;

—$(CH_2)_n$—O—R'', where n is 1 or 2, and R'' is hydrogen, a $C_5$–$C_7$ heteroaryl group, or

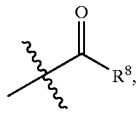

where $R^8$ is hydrogen, a $C_1$–$C_6$ alkyl group, a $C_3$–$C_6$ cycloalkyl group, or a 5- or 6-membered heteroaryl group optionally substituted with one or more substituents independently selected from the group consisting of halogens, methyl, and trifluoromethyl;

$(CH_2)_p$—N(R'')(R'''), where p is 1 or 2, R'' is as defined above, and R''' is hydrogen or an alkyl or alkoxy group optionally substituted with a $C_3$–$C_6$ cycloalkyl group optionally substituted with cyano;

—CH=N—R"", where R"" is hydrogen, a hydroxy group, or —OR⁹, where R⁹ is an alkyl, cycloalkyl, aryl, or heteroaryl group; or a 5- or 6-membered heterocyclic ring containing one to three heteroatoms independently selected from the group consisting of O, N, and S, the ring being optionally substituted with one or two substituents independently selected from the group consisting of methyl, methoxymethyl, oxygen, and $C_1$–$C_6$ alkoxy groups;

$R^3$ is hydrogen or a $C_1$–$C_6$ alkyl, $C_2$–$C_6$ alkenyl, or ($C_1$–$C_3$ alkoxy)$C_1$–$C_3$ alkyl group;

or $R^2$ and $R^3$ together with the atoms to which they are bound form a 5- or 6-membered ring containing one or two heteroatoms selected from the group consisting of O, N, and S, the ring being optionally substituted with oxygen, hydroxyl, or a $C_1$–$C_6$ alkyl group optionally substituted with a 5- or 6-membered heterocycloalkyl containing one or two heteroatoms independently selected from the group consisting of O, N, and S; and $R^4$ is hydrogen or an amino, halogen, hydroxyl, nitro, trifluoromethyl, cyano, $C_1$–$C_6$ alkyl, or $C_2$–$C_6$ alkenyl group;

pharmaceutically acceptable salt, or pharmaceutically acceptable solvate of said compound;

wherein said compound, pharmaceutically acceptable salt or pharmaceutically acceptable solvate is a GLP-1 receptor antagonist having an $IC_{50}$ binding affinity of less than 1 μM.

16. A pharmaceutical composition comprising an effective amount of a GLP-1 receptor antagonist according to claim 15 and a pharmaceutically acceptable carrier.

17. A method of inhibiting activation of the GLP-1 receptor comprising administering to a patient an effective amount of a GLP-1 receptor antagonist according to claim 15.

18. A compound selected from the group consisting of:

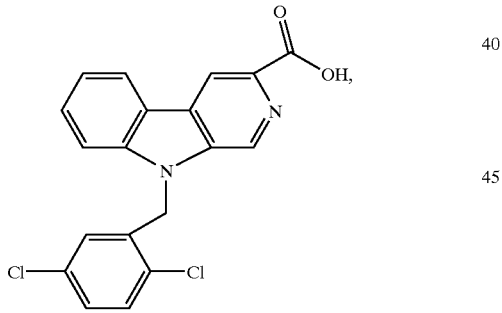

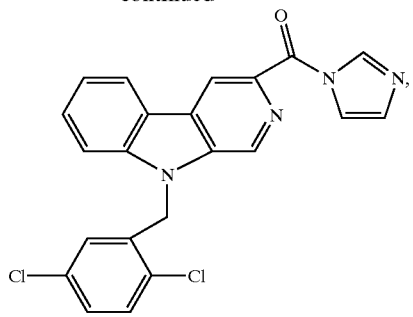

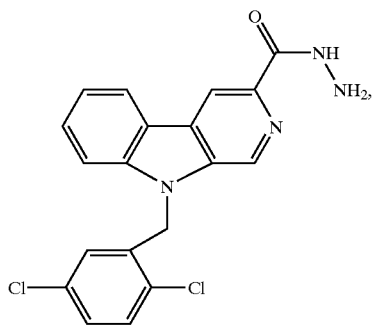

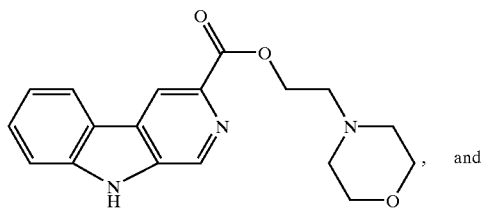

and

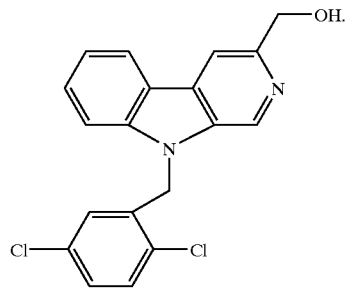

* * * * *